(12) United States Patent
Rentschler et al.

(10) Patent No.: US 11,730,928 B2
(45) Date of Patent: Aug. 22, 2023

(54) SPLIT OVERTUBE ASSEMBLY

(71) Applicants: The Regents of the University of Colorado, a Body Corporate, Denver, CO (US); Aspero Medical, Inc., Boulder, CO (US)

(72) Inventors: Mark E. Rentschler, Boulder, CO (US); Steven Edmundowicz, Centennial, CO (US); William Laybourn, Madison, WI (US); Randall N. Allard, Golden, CO (US); Jason Morton, Golden, CO (US)

(73) Assignees: ASPERO MEDICAL, INC., Boulder, CO (US); THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 270 days.

(21) Appl. No.: 16/875,793

(22) Filed: May 15, 2020

(65) Prior Publication Data
US 2020/0276417 A1    Sep. 3, 2020

Related U.S. Application Data

(63) Continuation-in-part of application No. 16/805,303, filed on Feb. 28, 2020, now Pat. No. 11,577,056,
(Continued)

(51) Int. Cl.
*A61M 25/06* (2006.01)
*A61M 25/10* (2013.01)
(Continued)

(52) U.S. Cl.
CPC ..... *A61M 25/0668* (2013.01); *A61B 1/00082* (2013.01); *A61B 1/00135* (2013.01);
(Continued)

(58) Field of Classification Search
CPC .......... A61M 25/0668; A61M 25/1002; A61M 25/1011; A61M 2025/1015;
(Continued)

(56) References Cited

U.S. PATENT DOCUMENTS 4,364,392 A    12/1982   Strother et al.
5,320,634 A     6/1994   Vigil et al.
(Continued)

FOREIGN PATENT DOCUMENTS

JP       3799612 B2    7/2006
JP    2012-81130 A     4/2012
(Continued)

OTHER PUBLICATIONS

Extended European Search Report, EP16871700.7, dated Jul. 5, 2019.
(Continued)

*Primary Examiner* — James D Ponton
*Assistant Examiner* — Neeraja Gollamudi
(74) *Attorney, Agent, or Firm* — Polsinelli PC

(57) ABSTRACT

An overtube assembly for use with an elongate medical tool includes an overtube including a flexible tubular body having a proximal end and distal end. The flexible tubular body includes a split extending from the proximal end to the distal end. The overtube assembly further includes an inflatable balloon coupled to a distal portion of the flexible tubular body. The flexible tubular body is disposable over a section of the elongate medical tool by inserting the elongate medical tool through the split.

18 Claims, 67 Drawing Sheets

Related U.S. Application Data which is a continuation-in-part of application No. 16/249,550, filed on Jan. 16, 2019, now Pat. No. 1,108,994.

(60) Provisional application No. 62/849,592, filed on May 17, 2019, provisional application No. 62/617,868, filed on Jan. 16, 2018.

(51) Int. Cl.
*A61B 1/00* (2006.01)
*A61B 1/012* (2006.01)

(52) U.S. Cl.
CPC .......... *A61B 1/012* (2013.01); *A61M 25/1002* (2013.01); *A61M 25/1011* (2013.01); *A61M 25/1029* (2013.01); *A61M 2025/109* (2013.01); *A61M 2025/1015* (2013.01); *A61M 2025/1086* (2013.01)

(58) Field of Classification Search
CPC ...... A61M 2025/1086; A61M 25/0013; A61B 1/00135
See application file for complete search history.

(56) References Cited

U.S. PATENT DOCUMENTS

| | | | |
|---|---|---|---|
| 5,423,745 A | 6/1995 | Todd | |
| 5,749,889 A | 5/1998 | Bacich et al. | |
| 6,120,516 A | 9/2000 | Selmon et al. | |
| 6,258,099 B1 | 7/2001 | Mareiro | |
| 6,478,807 B1 | 11/2002 | Foreman et al. | |
| 6,562,049 B1* | 5/2003 | Norlander | A61M 25/0075 606/108 |
| 6,676,667 B2 | 1/2004 | Mareiro et al. | |
| 6,835,189 B2 | 12/2004 | Musbach et al. | |
| 6,841,213 B2 | 1/2005 | Parsonage et al. | |
| 7,306,616 B2 | 12/2007 | Eidenschink et al. | |
| 7,354,419 B2 | 4/2008 | Davies, Jr. et al. | |
| 7,459,192 B2 | 12/2008 | Parsonage et al. | |
| 7,776,078 B2 | 8/2010 | Burgmeier et al. | |
| 7,927,362 B2 | 4/2011 | Shippy, III et al. | |
| 7,963,942 B2 | 6/2011 | Chen | |
| 7,985,063 B2 | 7/2011 | Schewe et al. | |
| 8,048,028 B2 | 11/2011 | Horn et al. | |
| 8,048,093 B2 | 11/2011 | Mapes et al. | |
| 8,096,942 B2 | 1/2012 | Yoshida et al. | |
| 8,202,245 B2 | 6/2012 | Weber et al. | |
| 8,216,267 B2 | 7/2012 | Pallazza | |
| 8,353,868 B2 | 1/2013 | Davies, Jr. et al. | |
| 8,550,985 B2 | 10/2013 | Weber et al. | |
| 8,597,239 B2 | 12/2013 | Gerrans et al. | |
| 8,690,824 B2 | 4/2014 | Holman et al. | |
| 8,771,332 B2 | 7/2014 | Johnson et al. | |
| 8,852,146 B2 | 10/2014 | Horn et al. | |
| 8,876,763 B2 | 11/2014 | Noddin | |
| 8,945,047 B2 | 2/2015 | McAuley et al. | |
| 8,945,168 B2 | 2/2015 | Davies, Jr. et al. | |
| 9,067,045 B2 | 6/2015 | Burton et al. | |
| 9,295,808 B2 | 3/2016 | De Kock et al. | |
| 9,339,169 B2 | 5/2016 | Rentschler et al. | |
| 9,409,001 B2 | 8/2016 | Aggerholm et al. | |
| 9,415,193 B2 | 8/2016 | Campbell et al. | |
| 9,492,297 B2 | 11/2016 | Pallazza | |
| 9,521,945 B2 | 12/2016 | Farhadi | |
| 9,592,119 B2 | 3/2017 | Tilson et al. | |
| 9,717,615 B2 | 8/2017 | Grandt | |
| 9,730,726 B2 | 8/2017 | Bacino et al. | |
| 9,867,529 B2 | 1/2018 | Farhadi | |
| 9,901,715 B2 | 2/2018 | Cully et al. | |
| 9,993,626 B2 | 6/2018 | Lysgaard | |
| 10,166,374 B2 | 1/2019 | Giasolli et al. | |
| 10,173,038 B2 | 1/2019 | Campbell et al. | |
| 10,201,683 B2 | 2/2019 | Schneider et al. | |
| 10,335,581 B2 | 7/2019 | Schneider et al. | |
| 10,376,679 B2 | 8/2019 | Cox et al. | |
| 10,456,564 B2 | 10/2019 | Terliuc et al. | |
| 10,617,853 B2 | 4/2020 | Campbell et al. | |
| 2003/0028097 A1* | 2/2003 | D'Amico | A61B 10/0241 600/427 |
| 2004/0044351 A1 | 3/2004 | Searle | |
| 2004/0092870 A1 | 5/2004 | Squire | |
| 2004/0167496 A1* | 8/2004 | Poole | A61M 25/0013 604/529 |
| 2004/0254422 A1 | 12/2004 | Singh | |
| 2005/0137615 A1 | 6/2005 | Mapes et al. | |
| 2006/0235457 A1 | 10/2006 | Belson | |
| 2006/0287574 A1 | 12/2006 | Chin | |
| 2007/0106216 A1 | 5/2007 | Noddin | |
| 2007/0112250 A1 | 5/2007 | Kura | |
| 2008/0228139 A1 | 9/2008 | Melsheimer | |
| 2008/0269559 A1 | 10/2008 | Miyamoto et al. | |
| 2010/0022832 A1 | 1/2010 | Makiyama | |
| 2010/0030204 A1 | 2/2010 | Stein et al. | |
| 2010/0240955 A1 | 9/2010 | Sinai et al. | |
| 2010/0318094 A1 | 12/2010 | Oishi et al. | |
| 2011/0105840 A1* | 5/2011 | Terliuc | A61B 1/00131 600/104 |
| 2012/0259217 A1* | 10/2012 | Gerrans | A61M 25/10181 604/514 |
| 2012/0289772 A1 | 11/2012 | O'Connell et al. | |
| 2014/0012281 A1 | 1/2014 | Wang et al. | |
| 2014/0276407 A1 | 9/2014 | Devries et al. | |
| 2015/0057657 A1 | 2/2015 | Squire et al. | |
| 2015/0088246 A1 | 3/2015 | Astarci et al. | |
| 2015/0105621 A1 | 4/2015 | Farhadi | |
| 2016/0058982 A1 | 3/2016 | Aggerholm et al. | |
| 2017/0035277 A1 | 2/2017 | Kucharski et al. | |
| 2017/0065155 A1* | 3/2017 | Farhadi | A61B 1/015 |
| 2017/0333075 A1 | 11/2017 | Bacino et al. | |
| 2017/0333686 A1 | 11/2017 | Schneider et al. | |
| 2018/0140804 A1 | 5/2018 | Tsukamoto et al. | |
| 2018/0256863 A1 | 9/2018 | Lysgaard | |
| 2018/0280666 A1 | 10/2018 | Yamazaki | |
| 2018/0304052 A1 | 10/2018 | Schneider et al. | |
| 2018/0368665 A1 | 12/2018 | Rentschler et al. | |
| 2019/0216297 A1 | 7/2019 | Rentschler et al. | |
| 2020/0215310 A1 | 7/2020 | Rentschler et al. | |
| 2021/0307589 A1 | 6/2021 | Rentschler et al. | |

FOREIGN PATENT DOCUMENTS

| | | | |
|---|---|---|---|
| WO | WO 2008/127224 A1 | 10/2008 | |
| WO | WO 2010/011843 A1 | 1/2010 | |
| WO | WO-2014190026 A1 * | 11/2014 | ......... A61B 1/00082 |
| WO | WO 2015/065163 A1 | 5/2015 | |
| WO | WO 2016/158294 A1 | 10/2016 | |
| WO | WO 2018/143254 A1 | 8/2018 | |

OTHER PUBLICATIONS

International Search Report and Written Opinion, PCT/US2016/064915, dated Apr. 13, 2017.

International Search Report and Written Opinion, PCT/US2019/013832, dated Apr. 10, 2019.

Non-Final Office Action, U.S. Appl. No. 16/249,550, dated Jun. 26, 2020.

Extended European Search Report, EP19741681.1, dated Sep. 7, 2021.

Final Office Action, U.S. Appl. No. 16/249,550, dated Dec. 22, 2020.

International Search Report and Written Opinion, PCT/US2020/033258, dated Aug. 19, 2020.

Non-Final Office Action, U.S. Appl. No. 15/780,493, dated Sep. 1, 2020.

Non-Final Office Action, U.S. Appl. No. 16/805,303, dated Oct. 22, 2021.

Notice of Allowance, U.S. Appl. No. 16/249,550, dated Apr. 21, 2021.

Notice of Reasons for Rejection, JP2020-560119 dated Sep. 6, 2021.

(56) References Cited

OTHER PUBLICATIONS

Response to Non-Final Office Action, U.S. Appl. No. 16/805,303, dated Jan. 14, 2022.
International Search Report and Written Opinion, PCT/US2022/024893, dated Jul. 5, 2022.

* cited by examiner

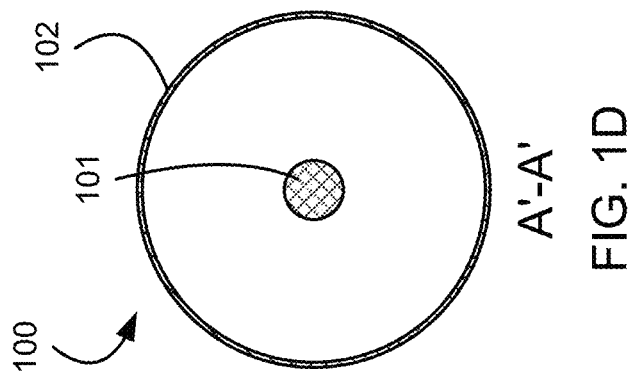
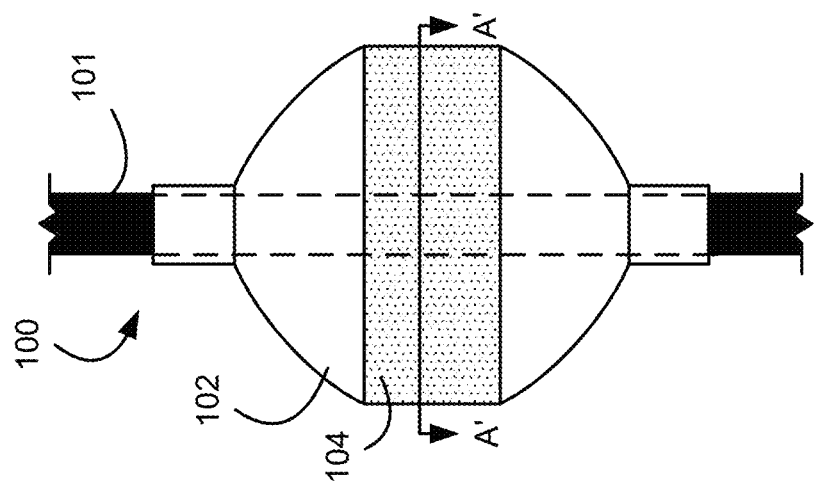
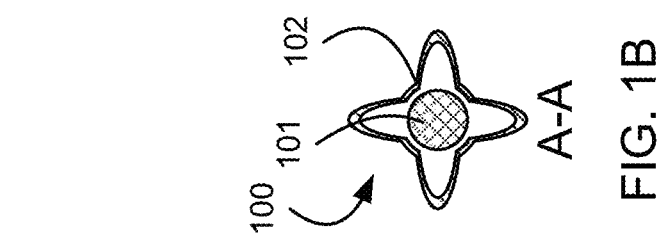
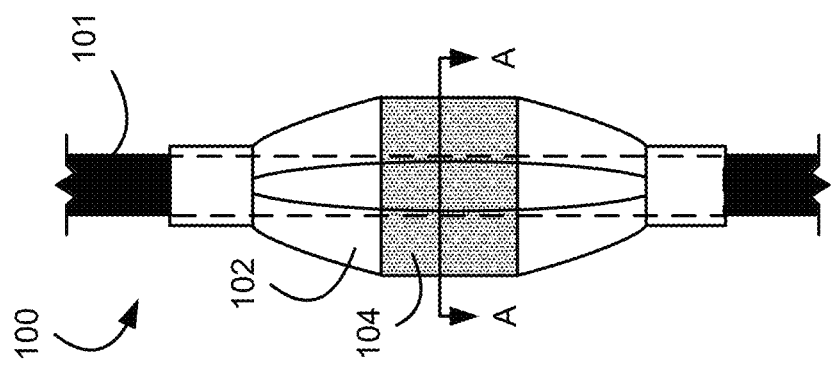

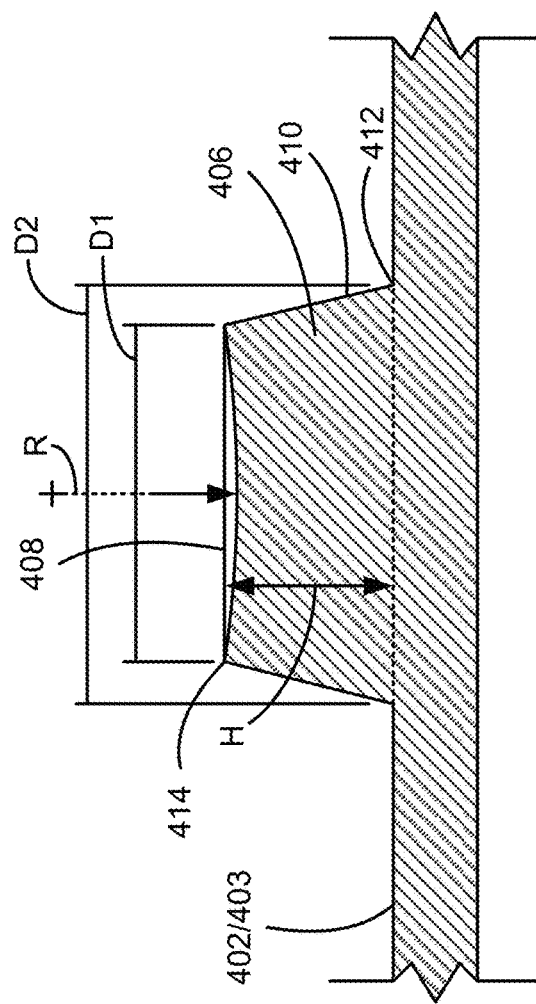
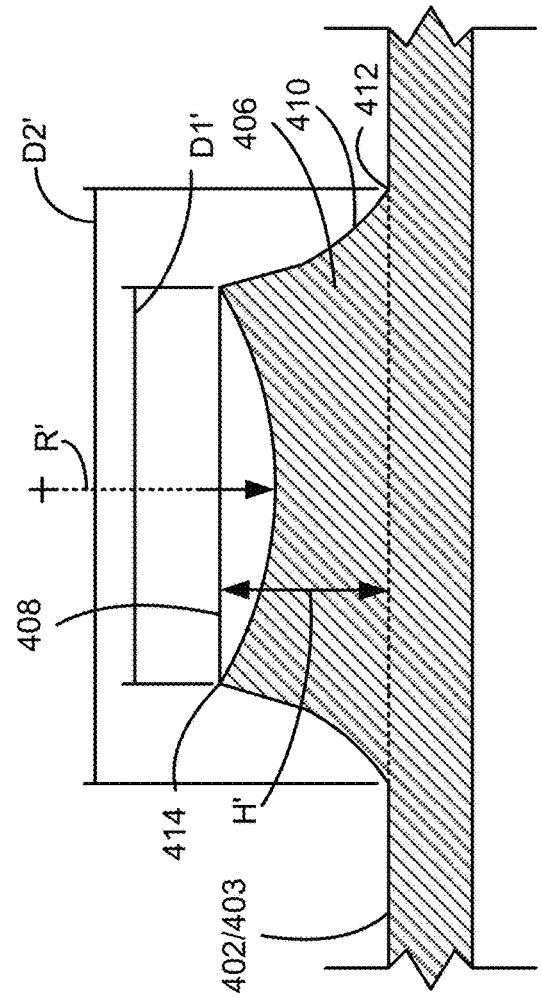

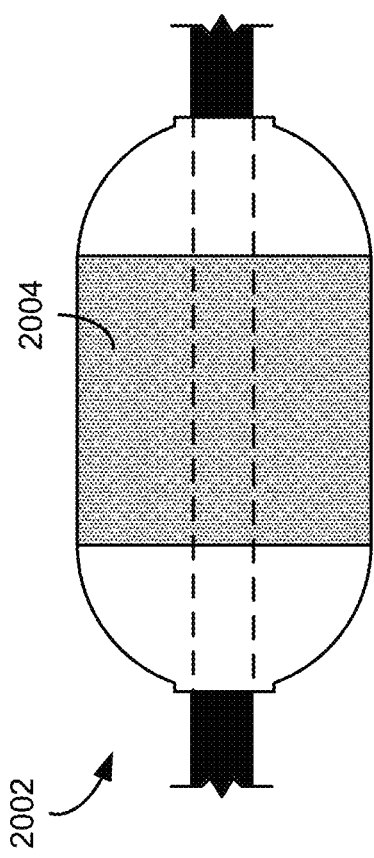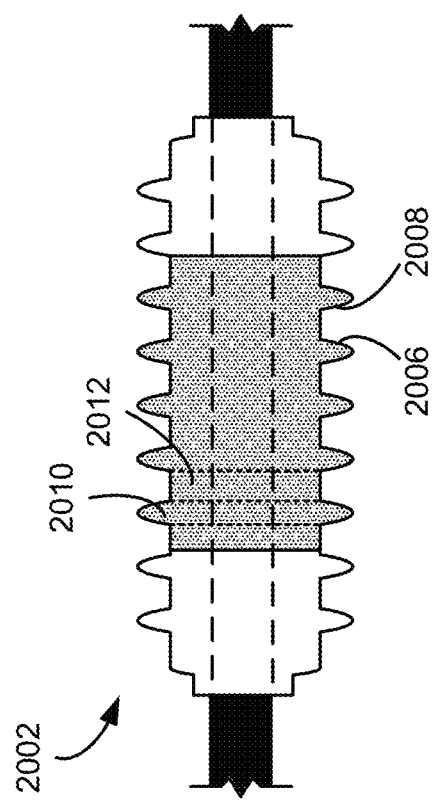
FIG. 20A
FIG. 20B

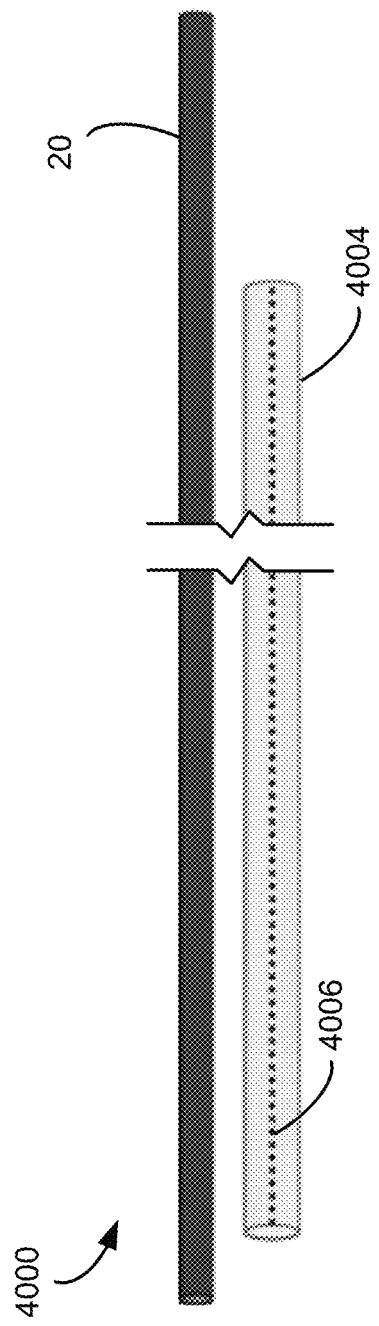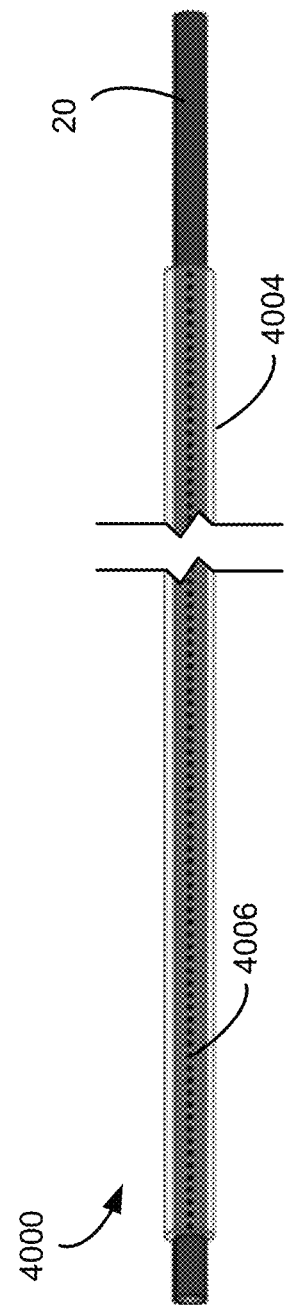
FIG. 40A
FIG. 40B

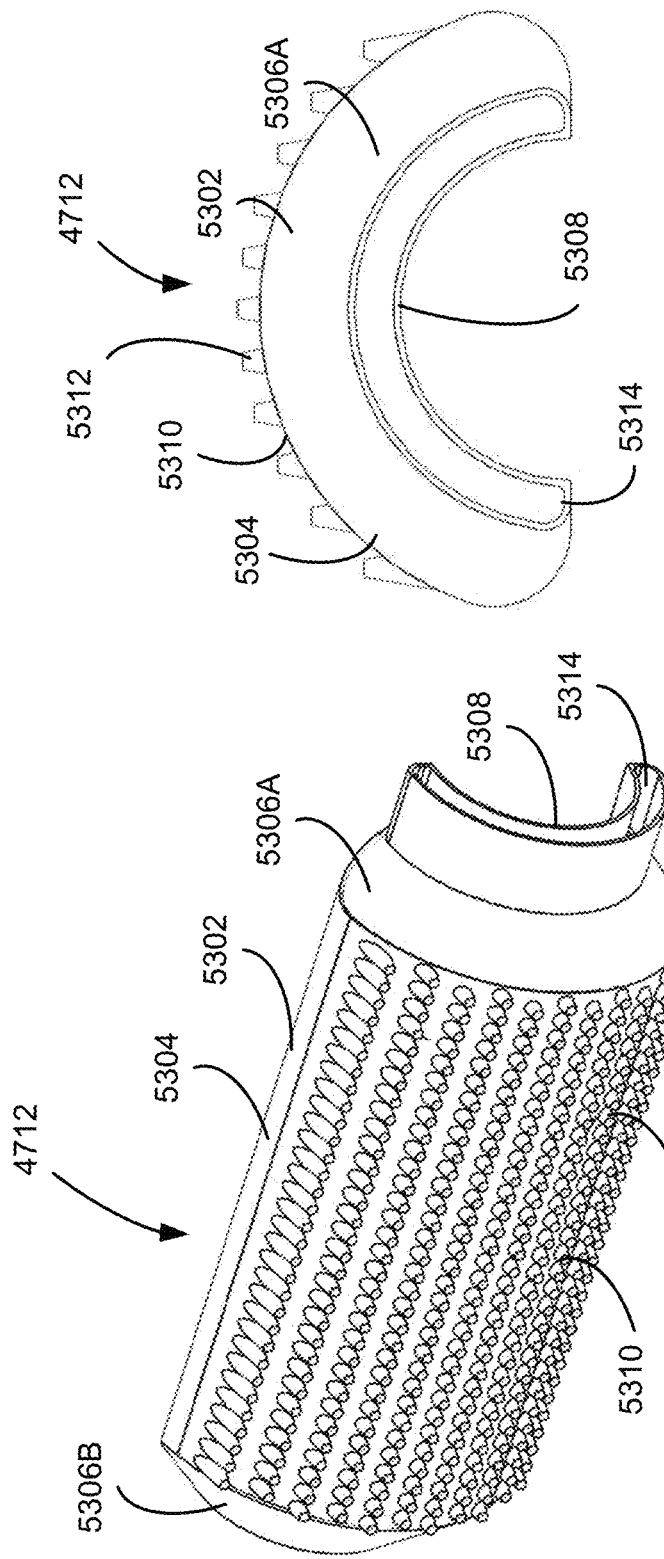

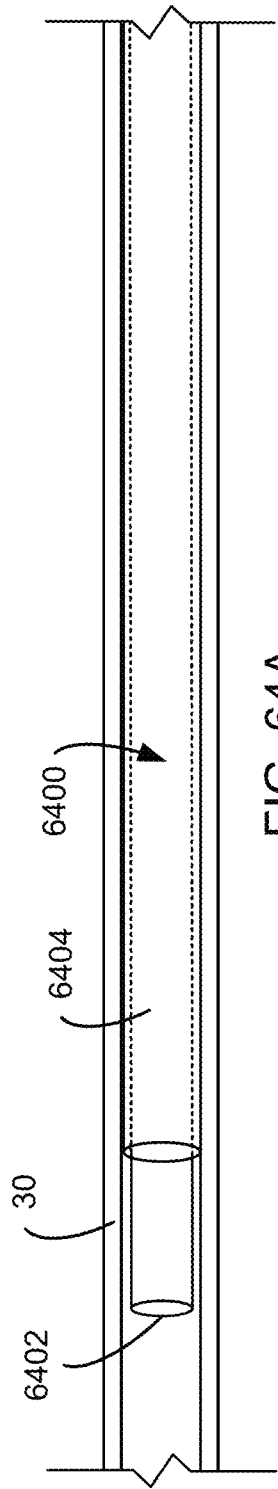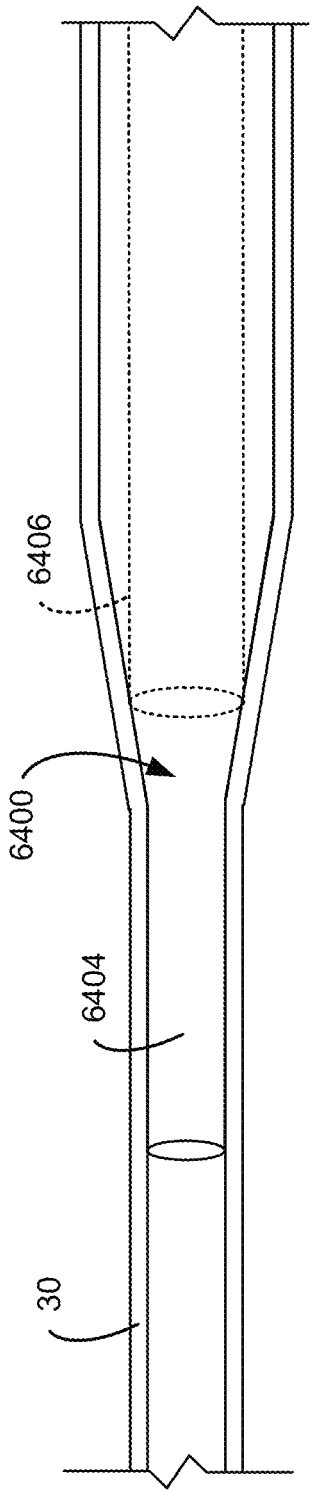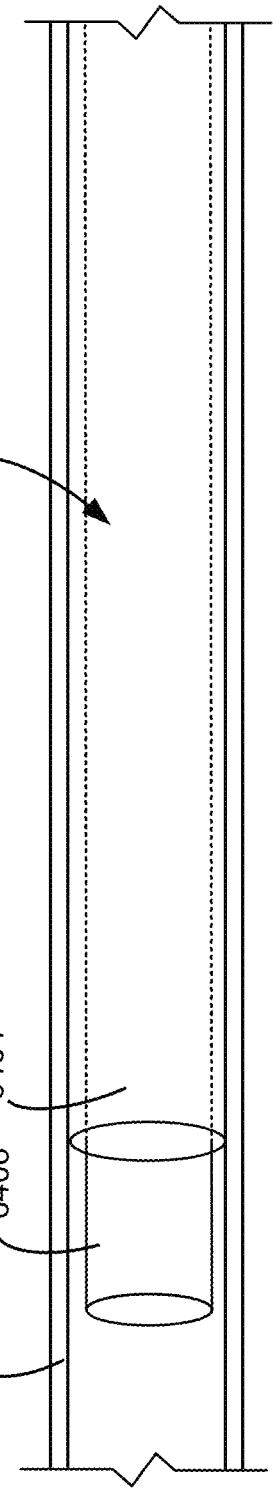

SPLIT OVERTUBE ASSEMBLY

CROSS-REFERENCE TO RELATED APPLICATION

This non-provisional utility application is a continuation-in-part of U.S. patent application Ser. No. 16/805,303 filed Feb. 28, 2020, and titled "MEDICAL DEVICES INCLUDING TEXTURED INFLATABLE BALLOONS," which application is a continuation-in-part of U.S. application Ser. No. 16/249,550, filed Jan. 16, 2019, and titled "MEDICAL DEVICES INCLUDING TEXTURED INFLATABLE BALLOONS," which claims priority under 35 U.S.C. § 119(e) from U.S. Patent Application No. 62/617,868, filed Jan. 16, 2018. This application is also related to and claims priority under 35 U.S.C. § 119(e) from U.S. Provisional Application No. 62/849,592, filed May 17, 2019, entitled "MEDICAL DEVICES INCLUDING TEXTURED SURFACES." The entire contents of each of the foregoing applications are incorporated herein by reference for all purposes.

STATEMENT REGARDING FEDERALLY SPONSORED RESEARCH OR DEVELOPMENT

This invention was made with government support under grant number 1636203 and 1827787 awarded by the National Science Foundation. The government has certain rights in the invention.

TECHNICAL FIELD

Aspects of the present disclosure are directed to overtube assemblies for use in medical procedures and, in particular, to overtube assemblies including textured balloons configured to selectively engage with a physiological lumen to facilitate transport of medical devices within the physiological lumen.

BACKGROUND

Endoscopy is a procedure wherein a highly trained physician pushes a long flexible endoscope through a physiological lumen of a patient, such as, but not limited to the colon or small bowel. Conventional endoscopes often struggle to complete procedures that involve irregular anatomy or small bowel examination. These factors can lead to missed diagnoses of early state conditions, such as colorectal cancer, which is the third most deadly cancer in America, but which has a 93% survival rate when detected in its initial stages.

To complete many of these examinations, double balloon enteroscopy (DBE) is often used. The double balloon system includes two balloons, one attached the front of the scope and one attached to a scope overtube. These balloons serve as anchoring points for the endoscope and provide extra support for the long flexible scope to be directed. When these anchoring balloons are inflated and deflated in succession, they aid in the advancement of the scope. When inflated, the balloons push against the wall of the colon, small bowel, or other physiological lumen, and grip the wall forming an anchor point, reducing movement while the scope pushes against the anchor point. DBE has been shown to be a very successful procedure for irregular anatomy patients and small bowel endoscopy.

Balloons commonly used in the art for DBE procedures are conventionally made of smooth latex-like materials. These materials have a low coefficient of friction, especially with the soft, mucous covered wall of the small bowel, colon, and other portions of the gastrointestinal (GI) tract. The low coefficient of friction can cause the balloon to slip prematurely, thus not allowing the scope to properly advance. Over-inflation of the balloons can increase friction with the wall of the small bowel or colon, but at the same time can also cause damage to the patient's GI tract.

Certain enteroscopy devices include the balloons in an overtube that is disposed over the enteroscope. Notably, due to their tubular shape, conventional overtubes require the enteroscope to be inserted through the overtube before insertion of the enteroscope into the patient. As a result, if a physician begins an enteroscopy procedure without an overtube and subsequently determines that an overtube is required, the enteroscope must be fully removed from the patient before attaching the overtube, effectively restarting the enteroscopy procedure.

There is thus a need in the art for novel devices that can be used to perform gastroenterology and other medical procedures. Such devices should increase the amount of successful completions of such procedures, and provide a more comfortable experience for the patient. By allowing for more colonoscopies to be completed fully, more cases of colorectal cancer would be found in early enough stages for successful treatment.

With these thoughts in mind among others, aspects of the devices and methods disclosed herein were conceived.

SUMMARY

In one aspect of the present disclosure, an overtube assembly for use with an elongate medical tool is provided. The overtube assembly includes an overtube including a flexible tubular body having a proximal end and distal end and a split extending from the proximal end to the distal end. The overtube assembly further includes an inflatable balloon coupled to a distal portion of the flexible tubular body. The flexible tubular body is disposable over a section of the elongate medical tool by inserting the elongate medical tool through the split.

In certain implementations, the flexible tubular body defines an air supply lumen extending from the distal end, the air supply lumen in communication with an internal volume of the inflatable balloon. In such implementations, the flexible tubular body may define an overtube port in communication with the air supply lumen, the inflatable balloon may define a balloon port in communication with the internal volume of the inflatable balloon, and the inflatable balloon may be disposed on the flexible tubular body such that the overtube port is in communication with the balloon port. A conduit may also extend between the overtube port and the balloon port.

In other implementations, the inflatable balloon is one of a plurality of inflatable balloons coupled to the distal portion of the flexible tubular body and the flexible tubular body defines a plurality of air supply lumens, each air supply lumen of the plurality of air supply lumens being in communication with an internal volume of a respective inflatable balloon of the plurality of inflatable balloons. In such implementations, the plurality of inflatable balloons may consist of two balloons disposed on opposite sides of the flexible tubular body. Also, in such implementations, each of the air supply lumens may have a diameter of about 0.8 mm and a wall thickness of about 0.33 mm.

In still other implementations, the inflatable balloon includes a textured exterior surface. In such implementations, the textured exterior surface includes a plurality of outwardly extending protrusions.

In other implementations, the split includes a proximal split portion having a first width and a distal split portion having a second width, the second width being greater than the first width.

In still other implementations, the flexible tubular body is formed from at least one of Nylon, PFA, PET, PTFE, FEP, HDPE, TPPE, and Hytrel Thermoplastic Polyester Elastomer with Everglide.

In other implementations, the flexible tubular body has a thickness from and including about 0.25 mm to and including about 1.0 mm.

In still other implementations, the flexible tubular body includes a first exterior surface portion adapted to provide greater friction with a wall of a physiological lumen than a second exterior surface portion of the flexible tubular body. In such implementations, the first exterior surface portion may include at least one of texturing or a coating.

In other implementations, the flexible tubular body includes a first interior surface portion adapted to provide greater friction with an exterior surface of the elongate medical tool than a second interior surface portion of the flexible tubular body. In such implementations, the first exterior surface portion may include at least one of texturing or a coating.

In still other implementations, the flexible tubular body includes a first overlapping portion and a second overlapping portion. The first overlapping portion and the second overlapping portion are configured to overlap when the flexible tubular body is disposed over the section of the elongate medical tool and the split is disposed between the first overlapping portion and the second overlapping portion. In such implementations, when overlapping, an interface is formed between an inner surface of the first overlapping portion and an outer surface of the second overlapping portion and at least one of the inner surface of the first overlapping portion and the outer surface of the second overlapping portion includes at least one of texturing or coating. In another of such implementations, when overlapping, an interface is formed between an inner surface of the first overlapping portion and an outer surface of the second overlapping portion. The inner surface of the first overlapping portion includes a first surface structure, the outer surface of the second overlapping portion includes a second surface structure, and the first surface structure is configured to engage the second surface structure when the first overlapping portion overlaps the second overlapping portion.

In other implementations, the flexible tubular body includes one or more reinforcement structures extending around the flexible tubular body.

In still other implementations the flexible tubular body includes one or more low flexibility regions disposed along the tubular body. In such implementations, the one or more low flexibility regions may include a hole through the tubular body or a local thinning of the tubular body.

In other implementations the overtube assembly further includes a zipper closure extending along the split.

In still other implementations, the tubular body includes a solid strip extending opposite the split and one or more bands extending circumferentially from the strip toward the split. In such implementations, the tubular body may include a rod adjacent the split and extending along the split and the one or more bands are coupled to the rod.

In another aspect of the present disclosure, an overtube for use with an elongate medical tool is provided. The overtube includes a flexible tubular body having a proximal end and distal end, the flexible tubular body including a split extending from the proximal end to the distal end. The flexible tubular body is disposable over a section of the elongate medical tool by inserting the elongate medical tool through the split.

In certain implementations, the split includes a proximal split portion having a first width and a distal split portion having a second width, the second width being greater than the first width.

In still other implementations, the flexible tubular body is formed from at least one of Nylon, PFA, PET, PTFE, FEP, HDPE, TPPE, and Hytrel Thermoplastic Polyester Elastomer with Everglide.

In other implementations, the flexible tubular body has a thickness from and including about 0.25 mm to and including about 1.0 mm.

In still other implementations, the flexible tubular body includes a first exterior surface portion adapted to provide greater friction with a wall of a physiological lumen than a second exterior surface portion of the flexible tubular body. In such implementations, the first exterior surface portion may include at least one of texturing or a coating.

In still other implementations, the flexible tubular body includes a first interior surface portion adapted to provide greater friction with an exterior surface of the elongate medical tool than a second interior surface portion of the flexible tubular body. In such implementations, the first interior surface portion may include at least one of texturing or a coating.

In other implementations, the flexible tubular body includes a first overlapping portion and a second overlapping portion. The first overlapping portion and the second overlapping portion are configured to overlap when the flexible tubular body is disposed over the section of the elongate medical tool and the split is disposed between the first overlapping portion and the second overlapping portion. In such implementations, when overlapping, an interface may be formed between an inner surface of the first overlapping portion and an outer surface of the second overlapping portion and at least one of the inner surface of the first overlapping portion and the outer surface of the second overlapping portion includes at least one of texturing or coating. In an alternative implementation, when overlapping, an interface may be formed between an inner surface of the first overlapping portion and an outer surface of the second overlapping portion. The inner surface of the first overlapping portion includes a first surface structure, the outer surface of the second overlapping portion includes a second surface structure, and the first surface structure is configured to engage the second surface structure when the first overlapping portion overlaps the second overlapping portion.

In still other implementations, the flexible tubular body includes one or more reinforcement structures extending around the flexible tubular body.

In other implementations, the flexible tubular body defines one or more voids disposed along the tubular body.

In still other implementations, the flexible tubular body includes one or more low flexibility regions disposed along the tubular body. In such implementations, the low flexibility regions may include a hole through the tubular body or a local thinning of the tubular body.

In other implementations, the overtube further includes a zipper closure extending along the split.

In still other implementations, the tubular body includes a solid strip extending opposite the split and one or more bands extending circumferentially from the strip toward the split. In such implementations, the tubular body may include a rod adjacent the split and extending along the split, the one or more bands being coupled to the rod.

In yet another aspect of the present disclosure, an overtube assembly for use with an elongate medical device is provided. The overtube assembly includes an overtube including a flexible tubular body. The flexible tubular body has a proximal end and distal end and includes a split extending from the proximal end to the distal end. The flexible tubular body further defines a first air supply lumen extending from the proximal end to a first overtube port and a second air supply lumen extending from the proximal end to a second air supply port. The overtube assembly further includes a first inflatable balloon coupled to a distal portion of the flexible tubular body. The first inflatable balloon includes a first internal volume and defines a first balloon port, the first balloon port in communication with the first overtube port. The overtube assembly further includes a second inflatable balloon coupled to the distal portion of the flexible tubular body. The second inflatable balloon has a second internal volume and defines a second balloon port, the second balloon port in communication with the second overtube port. The flexible tubular body is disposable over a section of the elongate medical tool by inserting the elongate medical tool through the split.

In certain implementations, the first inflatable balloon includes a first textured exterior surface and the second inflatable balloon includes a second textured exterior surface. Each of the first textured exterior surface and the second textured exterior surface further includes a plurality of outwardly extending protrusions.

In other implementations, the split includes a proximal split portion having a first width and a distal split portion having a second width, the second width being greater than the first width.

In another aspect of the present disclosure, a method of manufacturing an overtube assembly is provided, the overtube assembly including an overtube. The method includes coupling an inflatable balloon to an elongate tubular body of the overtube. The elongate tubular body includes a split extending from a proximal end of the elongate tubular body to a distal end of the elongate tube body and the elongate tubular body defines an air supply lumen and an overtube port in communication with the air supply lumen. The inflatable balloon has an internal volume and a balloon port in communication with the internal volume and coupling the inflatable balloon to the elongate tubular body includes coupling the elongate tubular body to the inflatable balloon such that the overtube port is in communication with the balloon port.

In certain implementations, the method further includes forming the elongate tubular body. In such implementations, the elongate tubular body may be formed without the split and forming the elongate tubular body includes forming the split in the elongate tubular body. Further in such implementations the elongate tubular body is extruded with a seam extending from the proximal end to the distal end and forming the split in the elongate tubular body includes splitting the elongate tubular body along the seam.

In other implementations, forming the elongate tubular body includes extruding the elongate tubular body.

In still other implementations, the method further includes after forming the split in the elongate tubular body, coupling a zipper closure to each side of the split.

In other implementations, the method further includes, after forming the elongate tubular body, modifying the flexibility of the tubular body at a location along the tubular body. In such implementation, modifying the flexibility of the tubular body may include at least one of thinning a portion of the tubular body at the location or forming a hole at the location.

In still other implementation, the method further includes forming the air supply port and forming the balloon port. In such implementations, forming the air supply port and the balloon port may include puncturing each of the elongate tubular body and the inflatable balloon with a hollow conduit such that the hollow conduit extends between the internal volume of the balloon and the air supply lumen.

In other implementations, when coupled to the elongate tubular body, the balloon has an open proximal end, the method further including sealing the open proximal end.

In still other implementations, the split includes a proximal split portion having a first width and a distal split portion having a second width, the second width being greater than the first width, the method further includes forming the distal split portion.

BRIEF DESCRIPTION OF THE DRAWINGS

Example implementations of the present disclosure are illustrated in referenced figures of the drawings. It is intended that the implementations and corresponding figures disclosed herein are to be considered illustrative rather than limiting.

FIG. 1A is a side elevation view of a first medical device according to the present disclosure including a balloon in a deflated state.

FIG. 1B is a cross-sectional view of the medical device of FIG. 1A.

FIG. 1C is a side elevation view of the medical device of FIG. 1A in which the balloon is in an at least partially inflated state.

FIG. 1D is a cross-sectional view of the medical device of FIG. 1C.

FIGS. 6A-6B are more detailed illustrations of the cross-sectional views of FIGS. 4B and 5B.

FIGS. 20A-20B are schematic illustrations of another example balloon in accordance with the present disclosure in each of an at least partially inflated state and a collapsed state, respectively.

FIGS. 40A-40B are schematic illustrations of an endoscope and split overtube according to the present disclosure in each of a decoupled and coupled arrangement, respectively.

FIGS. 53 and 54 are an isometric view and an end view of an inflatable balloon of the overtube assembly of FIG. 47.

FIGS. 64A-64C illustrate insertion of an endoscope into a physiological lumen using an expandable overtube in accordance with the present disclosure.

DETAILED DESCRIPTION

Figure 1E:
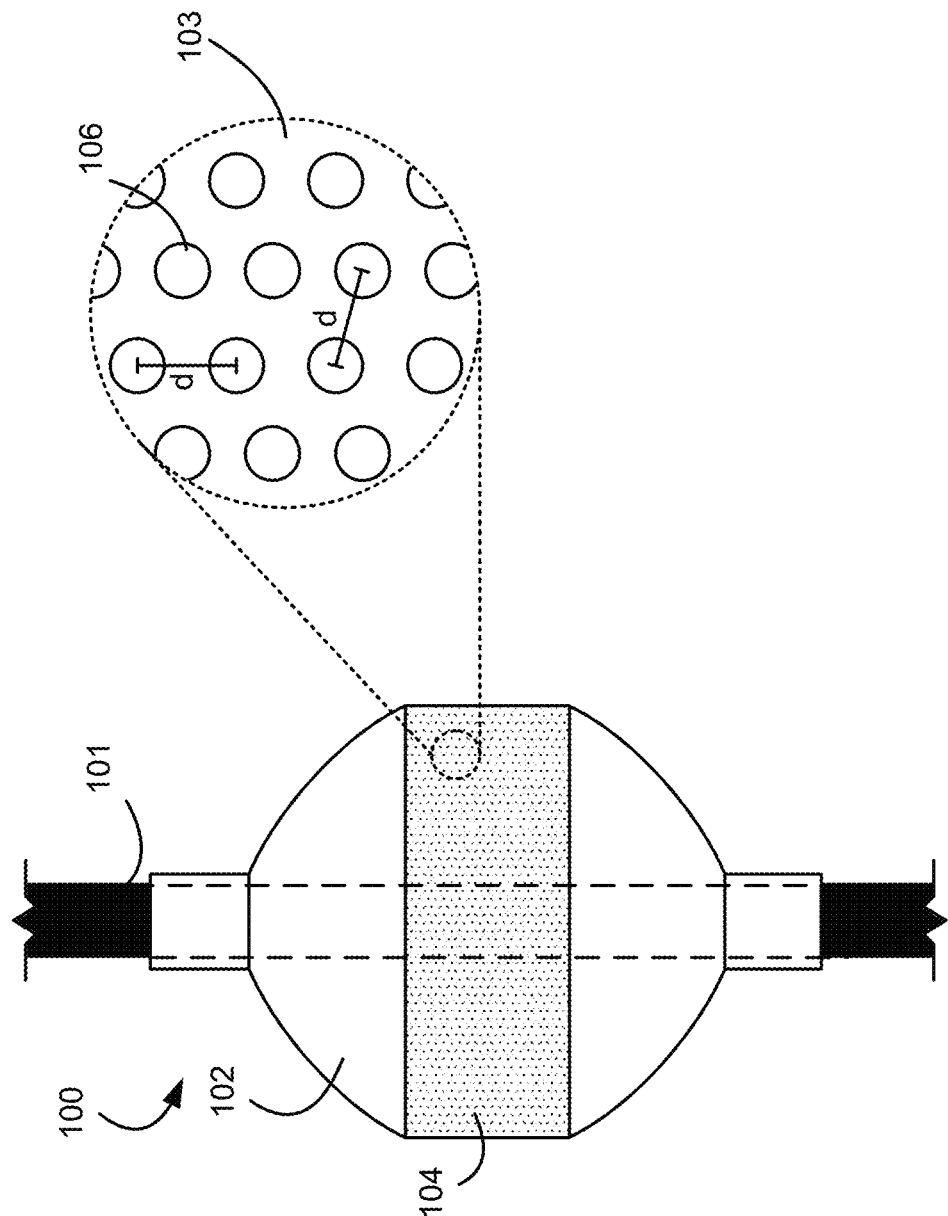
FIG. 1E is a side elevation view of the medical device of FIG. 1A in the at least partially inflated state and further including a detail view illustrating protrusions disposed on the balloon.

The current disclosure relates in part to balloon designs that can be incorporated into medical devices, such as endoscopes. The current disclosure further relates to overtubes incorporating such balloons that may be coupled to medical devices, such as endoscopes. More particularly, the current disclosure relates to balloons having exterior surfaces that are at least partially textured. Texturing of the balloons is achieved by the inclusion of multiple pillar-like protrusions extending from the surface of the balloon. In at least one application of the current disclosure, a medical device including the balloon is disposed within a physiological lumen with the balloon in a substantially deflated state. The physiological lumen may be a portion of a patient's GI tract, but more generally may be any vessel, airway, duct, tract, stricture, sphincter, biliary stricture, or similar physiological structure. Once positioned within the physiological lumen, the balloon may be inflated such that the protrusions contact the lumen wall, thereby engaging the balloon and medical device with the lumen wall. The balloon may be subsequently deflated to facilitate disengagement of the protrusions from the wall of the lumen, thereby permitting movement of the medical device. Accordingly, the balloons (or similar structures) disclosed herein include textured/patterned surfaces that provide increased friction and adhesion with biological tissue as compared to conventional smooth balloons. As a result of such increased friction and adhesion, balloons in accordance with the present disclosure more reliably engage biological tissue as compared to conventional balloon designs.

As described below in further detail, the shape and distribution of the protrusions may vary in applications of the present disclosure to provide varying degrees of traction between the balloon and the biological tissue with which the balloon is in traction. In certain implementations, the protrusions may also be configured to deform in response to a strain applied to the balloon. Such deformation alters the adhesive and frictional properties of the protrusions. As a result, a physician may control the relative traction of the balloon to the biological tissue by selectively inflating or deflating the balloon. For example, a physician may apply a first strain to the balloon (e.g., by inflating the balloon to a first extent) resulting in a first degree of deformation of the protrusions and a corresponding first engagement level of the balloon (e.g., a first level of engagement based on the adhesive and frictional properties of the protrusions when in a first shape). Subsequently, the physician may apply a second strain (e.g., by modifying the degree to which the balloon is inflated) resulting in a second degree of deformation of the protrusions and a corresponding second engagement level of the balloon.

In certain implementations of the present disclosure, the foregoing balloons may be incorporated into an overtube assembly that may be coupled to an endoscope (or similar elongate medical device) to facilitate transit of the endoscope within a physiological lumen of a patient. In at least some implementations, the overtube assembly includes a split overtube that facilitates coupling of the overtube assembly without removing the endoscope from a patient.

Although discussed herein primarily in the context of endoscopic balloons for use in the GI tract, the present disclosure may be used in a variety of medical and non-medical applications. Accordingly, to the extent that any particular applications of the present disclosure are discussed herein, such applications should not be viewed as limiting the scope of the present disclosure. Nevertheless example implementations of the present disclosure are discussed below to provide additional details regarding aspects of the present disclosure.

Figure 10:
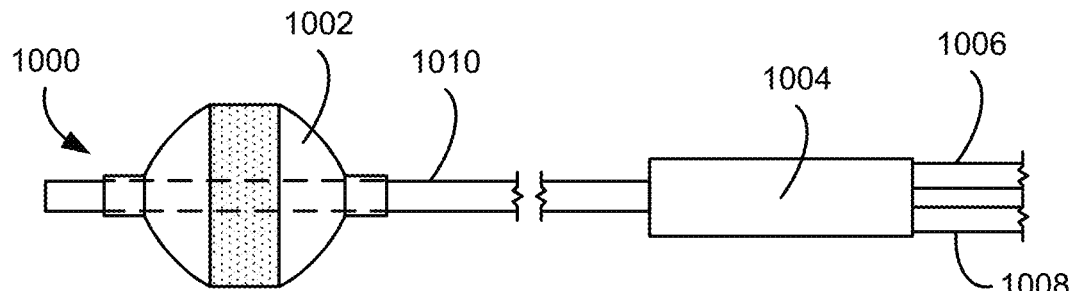
FIG. 10 is a schematic illustration of a medical device in the form of a catheter delivery tool in accordance with the present disclosure.

FIGS. 1A-1E are various views of an example medical device 100 including an inflatable balloon 102 in accordance with the present disclosure. More specifically, FIG. 1A is a side elevation view of the medical device 100 with the balloon 102 in deflated or collapsed state, FIG. 1B is a cross-sectional view along cross-section A-A of the balloon 102 of FIG. 1A, FIG. 10 is a side elevation view of the medical device 100 in an at least partially inflated state, FIG. 1D is a cross-sectional view along cross-section A'-A' of the balloon 102 of FIG. 10, and FIG. 1E is a side elevation view of the medical device 100 including an inlay illustrating a textured portion 104 of the balloon 102.

For purposes of the present disclosure, balloons disclosed herein are described as being in various states corresponding to various stages of inflation and deflation. An "unstrained state", for example, refers to a state in which in which the corresponding balloon may be partially inflated but not yet subject to strain and, as a result, generally corresponds to the "as-molded" shape of the balloon. A "strained state" generally refers to a state in which a balloon is inflated beyond the extent necessary to achieve the unstrained state. A "collapsed state", in contrast, generally refers to a state of the balloon in which at least a portion of the balloon constricts or is otherwise reduced as compared to the unstrained state. In certain implementations, balloons in accordance with the present disclosure may be biased into a collapsed state. Alternatively, balloons in accordance with the present disclosure may transition into the collapsed state in response to air (or other gas) being removed from the balloon or in response to the balloon being otherwise deflated from the unstrained state. Balloons herein may also be described as being "at least partially inflated", which generally refers to a state of the balloon including the unstrained state and any degree of inflation beyond the unstrained state. Similarly, the "collapsed" state may generally refer to balloons that are in any degree of collapse up to but excluding the unstrained state.

During use, the medical device 100 may be inserted into and located within a physiological lumen of a patient. Such insertion may generally be performed while the balloon 102 is in the deflated state illustrated in FIG. 1A. Once properly located, air or a similar fluid medium may be provided to the balloon 102 to inflate the balloon, as shown in FIG. 1B. When such inflation is performed with the balloon 102 within the physical lumen, at least a part of the textured portion 104 may be made to abut an inner wall of the physiological lumen, thereby causing frictional and adhesive engagement between the textured portion 104 and the physiological lumen and mucosal lining.

Various arrangements for the balloon 102 on the medical device 100 are feasible. In the specific example of FIGS. 1A-1E, the balloon 102 has a cylindrical body capped by hemispherical ends. In another non-limiting example, the balloon 102 is disposed around an endoscope 101 or similar tubular body of the medical device 100 such that the balloon 102 forms a toroidal or spherical shape having a central lumen. In another non-limiting example, the balloon 102 is disposed around the endoscope 101 forming a cylindrical shape having hemispherical rounded ends, wherein the endoscope 101 runs along the major axis of the cylinder. In other implementations, the balloon 102 may be ellipsoid in shape or "pill" shaped. Regardless of the foregoing, balloons in accordance with the present disclosure may be substantially any shape as desired.

The balloon 102 may be made of at least one non-rigid material. For example, in one example implementation the balloon material may include one or more of low-density polyethylene (LDPE), latex, polyether block amide (e.g., PEBAX®), silicone, polyethylene terephthalate (PET/PETE), nylon, polyurethane, and any other thermoplastic elastomer, siloxane, or other similar non-rigid materials. In certain implementations, the balloon 102 may be formed from one material; however, in other implementations the balloon 102 may be formed from multiple materials. For example, the balloon 102 may include a body formed from a first material but may also include reinforcing or structural members formed from a second material.

Material selection for the balloon 102 may also be based, in part, on material hardness. Although material hardness may vary based on application, in at least one specific implementation, the balloon 102 may be formed from a material having a predetermined hardness of Shore 30A such as, but not limited to, Dow Corning Class VI Elastomer C6-530, which is a liquid silicone rubber elastomer.

In general, the balloon 102 has a first diameter or shape when in a collapsed or unstrained state and a second diameter when inflated into an unstrained state, the second diameter being larger than the first diameter. In certain implementations, the balloon 102 may be further inflatable beyond the unstrained state into a strained state. For example, in at least one implementation the balloon 102 can be strained up to about 1,000% relative to its uninflated state, although other maximum strain levels are possible. In other implementations, the balloon 102 does not have a set lower inflation limit. The balloon 102 may also be configured to be inflated to a first turgid state having a defined shape and then be further inflated up to a maximum strain while retaining the defined shape.

The balloon 102 may be structured such that, when deflated or due to biasing, the balloon 102 collapses into a particular shape. For example, as illustrated in FIGS. 1A and 1B, the balloon 102 may be configured to collapse into a star or similar shape. Such controlled collapse of the balloon 102 may achieved in various ways including, without limitation, selectively reinforcing portions of the balloon 102 with additional material and including semi-rigid structural elements coupled to or embedded within the balloon 102. In other implementations, the balloon 102 may form a pill, ovoid, or similar elongated shape when deflated, including a shape that substantially corresponds to the inflated shape of the balloon 102.

As illustrated FIG. 1C, the balloon 102 includes at least one textured portion 104. In general and as illustrated in the inlay of FIG. 1C, the textured portion 104 includes multiple protrusions, such as protrusion 106, extending from a surface 103 of the balloon 102. The protrusions 106 of the textured portion 104 may have any pattern. For example and without limitation, the textured portion 104 may include evenly spaced protrusions arranged in a regular geometric pattern, such as a grid. The balloon 102 illustrated in FIG. 1C, for example, includes protrusions arranged in a triangular grid pattern. In other implementations, other grid patterns may be used including, without limitation, square, rectangular, hexagonal, and octagonal grid patterns or any other suitable grid pattern based on a tessellation of geometric shapes. In certain implementations, the textured portion 104 may include multiple areas of protrusions, with each area having a different protrusion density or protrusion pattern. In still other implementations, the protrusions may be arranged in a random or semi-random pattern across the textured portion 104. More generally, textured portions in accordance with implementations of the present disclosure may include any suitable arrangement of protrusions.

In certain implementations, the protrusions 106 may be evenly spaced such that the center-to-center dimension between adjacent protrusions is constant in a given state of the balloon 102 (e.g., the unstrained state). For example, in one implementation the center-to-center spacing between protrusions (as indicated in the inlay of FIG. 1E by dimension "d") may be about 20 μm to about 1,000 μm in the unstrained state. In other implementations, the protrusions may be evenly spaced with a center-to-center spacing from and including about 50 μm to and including about 750 μm apart from one another. In yet another implementation, the protrusions may be evenly spaced with a center-to-center spacing from and including about 100 μm to and including about 600 μm apart from one another. In still other implementations, the center-to-center spacing between protrusions may be greater than 1000 μm.

The inset of FIG. 1E illustrates the protrusions 106 arranged in longitudinally extending rows with adjacent rows being offset but equally spaced. It should be appreciated, however, that in other implementations of the present disclosure, aspects of the arrangement of the protrusions 106 may vary. For example, in certain implementations, protrusions of adjacent longitudinal rows may be aligned with each other. Similarly, all rows may be spaced uniformly (e.g., all rows may be spaced 1000 μm apart). Alternatively, spacing between all rows may vary or may only be uniform for a subset of adjacent rows. As yet another example, rows of the protrusions may extend along varying lengths of the textured portion 104. Moreover, in at least certain implementations, the protrusions 106 may not be arranged in longitudinal rows. Rather, the protrusions may be arranged in any suitable pattern including, without limitation, circumferential rows, biased rows (e.g., rows extending both longitudinally and circumferentially), or in a random or pseudo-random pattern.

The protrusions 106 may be formed in various ways. For example and without limitation, the protrusions may be integrally formed with the balloon 102 (e.g., by simultaneously molding the balloon 102 and the protrusions), may be separately formed from and subsequently attached to the balloon 102 (e.g., by first extruding the balloon and then adhering the protrusions to the balloon 102), or may be formed directly onto the balloon 102 (e.g., by a co- or over-molding process in which the balloon 102 is first molded and then the protrusions are molded onto the balloon 102).

As previously discussed, balloons according to the present disclosure may be configured to inflate or deflate in a particular manner. For example, as illustrated in FIG. 1A, the balloon 102 is configured to collapse into a star- or clover-shape when deflated. More specifically, the balloon 102 is configured such that certain longitudinal sections of the balloon 102 are collapsed to a greater degree than others when air is removed from the balloon 102. Such selective collapse may be achieved, for example, by increasing the thickness of the balloon 102 in the longitudinal portions that are to remain protruding when the balloon 102 is deflated.

A similar design is illustrated in FIGS. 20A-20B. More specifically, FIG. 20A illustrates a balloon 2002 in an at least partially inflated state while FIG. 20B illustrates the balloon 2002 in a collapsed state. Similar to the balloon 102 of FIGS. 1A-1B, the balloon 2002 is configured to selectively collapse when deflated. More specifically, and as illustrated in FIG. 20B, the balloon 2002 is generally divided into alternating axial bands configured to have different diameters when collapsed. For example, a first band 2010 is configured to collapse to a lesser degree than a second band 2012. As previously noted, such selective collapse may be achieved by increasing the thickness of the first band 2010 or by otherwise reinforcing the first band 2010. In other implementations, the shape of at least some of the bands when in the deflated state may be dictated by a mandrel or similar body disposed within the balloon 2002 and about which the balloon 2002 collapses when deflated.

Varying the degree to which the balloon collapses, as illustrated in the examples of FIGS. 1A-1B and 20A-20B, facilitates insertion and transportation of the balloon when in the deflated state. In particular, by reducing the proportion of protrusions that are outwardly/radially facing or otherwise disposed at a maximum diameter, the overall adhesion and friction provided by the balloon is reduced. As a result, the likelihood and amount of contact between the balloon and a wall of a physiological lumen is significantly reduced. Referring to FIGS. 20A-20B, for example, the balloon 2002 includes a textured portion 2004 having protrusions according to the present disclosure. When in the at least partially inflated state (as shown in FIG. 20A), each of the protrusions is directed substantially outwardly/radially and, as a result, is able to readily contact and engage the wall of the physiological lumen. However, when in the collapsed state (as shown in FIG. 20B), sections of the textured portion 2004 of the balloon 2002 (such as faces 2006 and 2008) and their respective protrusions are directed at least partially in a longitudinal direction and, as a result, are less likely to directly engage the wall of the physiological lumen. Similarly, sections of the textured portion 2004 (such as the second band 2012) may be recessed when the balloon 2002 is in the deflated state relative to other sections of the textured portion 2004 (such as the first band 2010). As a result the recessed sections are less likely to contact and engage the wall of the physiological lumen.

Figure 21A:
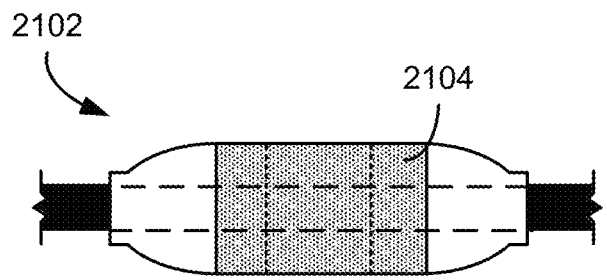
FIGS. 21A-21O are schematic illustrations of yet another example balloon in accordance with the present disclosure in each of a collapsed state, a partially inflated state, and an inflated state, respectively.
Figure 21B:
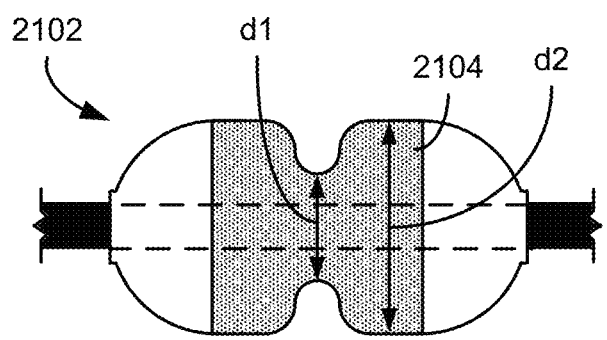
Figure 21C:
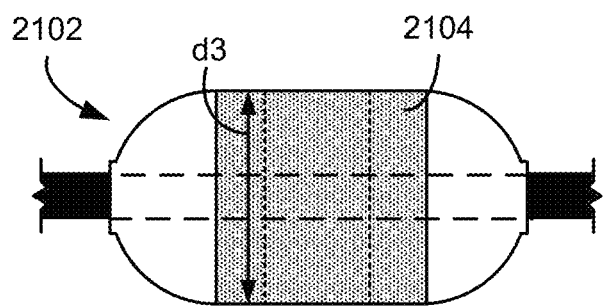

FIGS. 21A-21C illustrates another example balloon 2102 exhibiting non-uniform inflation/deflation. FIG. 21A illustrates the balloon 2102 in a collapsed or unstrained state and in which the balloon 2102 assumes a pill-shaped configuration. As shown in FIG. 21B, the balloon 2102 may be inflated to a first inflation level in which the balloon 2102 assumes an hourglass (or similar shape) in which at least a portion of the balloon 2102 expands to a diameter (d1) that is less than a diameter (d2) of other portions of the balloon 2102. At a second inflation level, the balloon 2102 may expand such that the diameter of the balloon is substantially uniform (d3).

In certain implementations, the controlled inflation of the balloon 2102 may be used to vary the adhesive and frictional force between the balloon 2102 and a wall of a physiological lumen within which the balloon 2102 is disposed. For example, the balloon 2102 includes a textured portion 2104 having protrusions according to the present disclosure. When in the partially inflated state (as illustrated in FIG. 21B), the diameter of the textured portion 2104 varies such that only a limited proportion of the protrusions are each of disposed at the maximum diameter of the balloon 2102 and oriented in an outward/radial direction. As a result, the adhesion and friction between the balloon 2102 and wall of the physiological lumen is reduced as compared to when the balloon 2102 is further inflated (as illustrated in FIG. 21C) such that substantially all of the textured portion 2104 is at the same diameter. Accordingly, a user of the balloon 2102 may inflate the balloon 2102 to the first inflation level to achieve a first degree of engagement and to the second inflation level to achieve a second, greater degree of engagement.

Figure 22A:
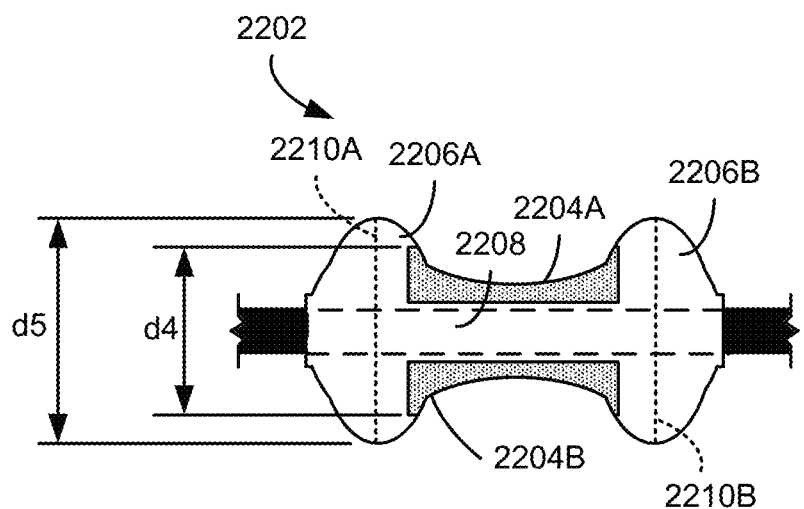
FIGS. 22A and 22B are schematic illustrations of another example balloon in accordance with the present disclosure in each of a collapsed state and an at least partially inflated state, respectively, illustrating controlled collapse of the balloon.
Figure 22B:
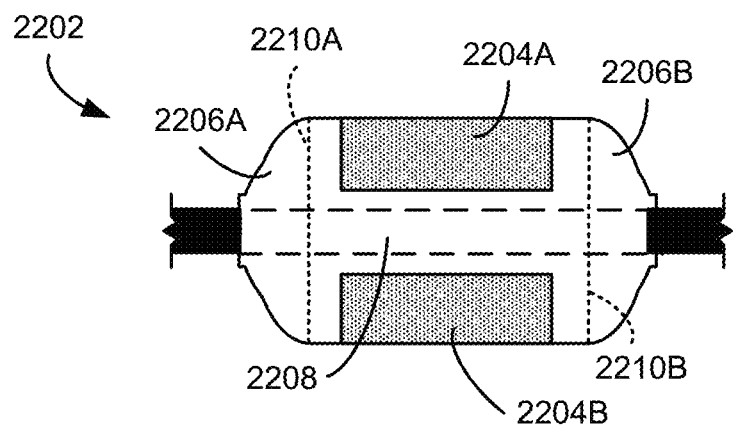

FIGS. 22A and 22B illustrate another example balloon 2202. FIG. 22A illustrates the balloon 2202 in a collapsed state while FIG. 22B illustrates the balloon 2202 in an at least partially inflated state. As shown, the balloon 2202 generally includes textured portions 2204A, 2204B disposed between two untextured ends 2206A, 2206B. The balloon 2202 also includes an untextured portion 2208 disposed between the textured portions 2204A, 2204B.

The textured portions 2204A, 2204B and the untextured ends 2206A, 2206B are structured such that, when in the collapsed state illustrated in FIG. 22A, the textured portions 2204A, 2204B have a maximum diameter (d4) that is less than a maximum diameter (d5) of the untextured ends 2206A, 2206B. In such an arrangement, the outermost surface of the balloon 2202 is provided by the untextured ends 2206A, 2206B while the textured portions 2204A, 2204B are disposed radially inward of the outermost surface. In other words, when in the collapsed state, the textured portions 2204A, 2204B may become concave. As a result, when in the collapsed state illustrated in FIG. 22A, contact between the balloon 2202 and an inner surface of a physiological lumen within which the balloon 2202 may be disposed is primarily between the inner surface of the physiological lumen and the untextured ends 2206A, 2206B.

As the balloon 2202 is inflated, the diameter of the textured portions 2204A, 2204B may expand to at least equal that of the untextured ends 2206A, 2206B, as illustrated in FIG. 22B. As a result, the textured portions 2204A, 2204B may come into contact with the inner surface of the physiological lumen, thereby increasing friction between the balloon 2202 and the inner surface of the physiological lumen.

In light of the arrangement illustrated in FIGS. 22A and 22B, the balloon 2202 may be inserted into and moved along the physiological lumen in the deflated/low-friction state illustrated in FIG. 22A. When the balloon 2202 is at an intended location, the balloon 2202 may then be inflated to expose the textured portions 2204A, 2204B and to cause the textured portions 2204A, 2204B to come into contact with the inner surface of the physiological lumen. Doing so increases friction between the balloon 2202 and the inner surface of the physiological lumen and may be used to anchor or otherwise reduce movement of the balloon 2202 within the physiological lumen.

As illustrated in FIGS. 22A and 22B, in at least some implementations of the present disclosure, an untextured portion 2208 may be disposed between textured portions of the balloon 2202. For example, one or more untextured portions 2208 may extend longitudinally between textured portions of the balloon 2202, such as the textured portions 2204A, 2204B. When in the collapsed state illustrated in FIG. 22A, the untextured portion 2208 may have a diameter similar to that of the untextured ends 2206A, 2206B, thereby providing another low-friction surface that contacts the inner surface of the physiological lumen during insertion and transportation. In such cases, when in the deflated configuration, the textured portions 2204A, 2204B may generally be concave about an axis extending perpendicular to a longitudinal axis of the balloon 2202. Alternatively, the untextured portion 2208 may deflate similar to the textured portions 2204A, 2204B. In such implementations, the untextured portion 2208 may similarly become concave when deflated, giving the balloon 2202 an "hourglass" or similar shape that tapers radially inward from the untextured ends 2206A, 2206B when in the deflated state.

Figure 23A:
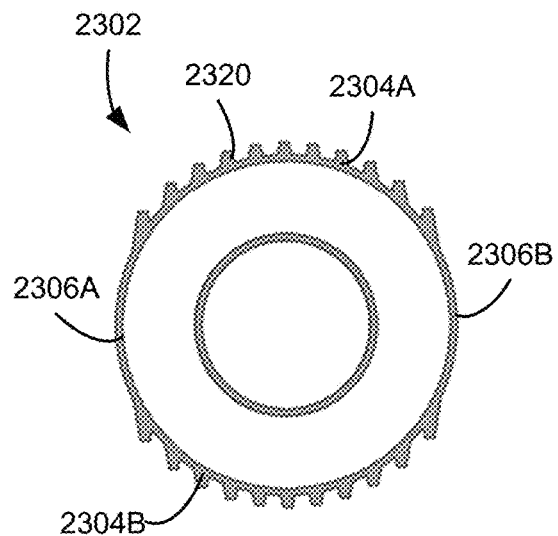
FIGS. 23A-23C are schematic illustrations of still another example balloon in accordance with the present disclosure in each of an unstrained state, a collapsed state, and an inflated/strained state, respectively, illustrating an alternative approach to controlled collapse of the balloon.
Figure 23B:
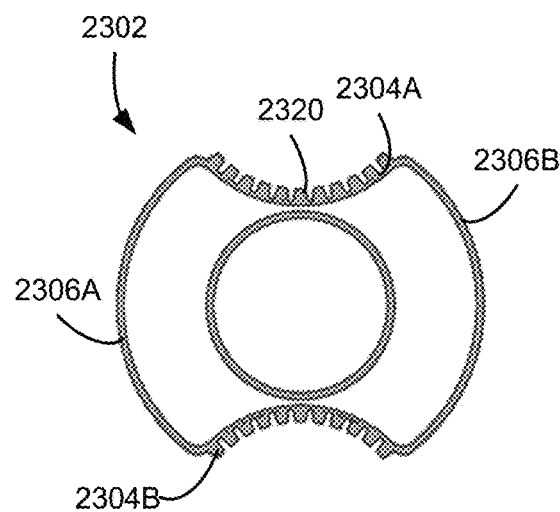
Figure 23C:
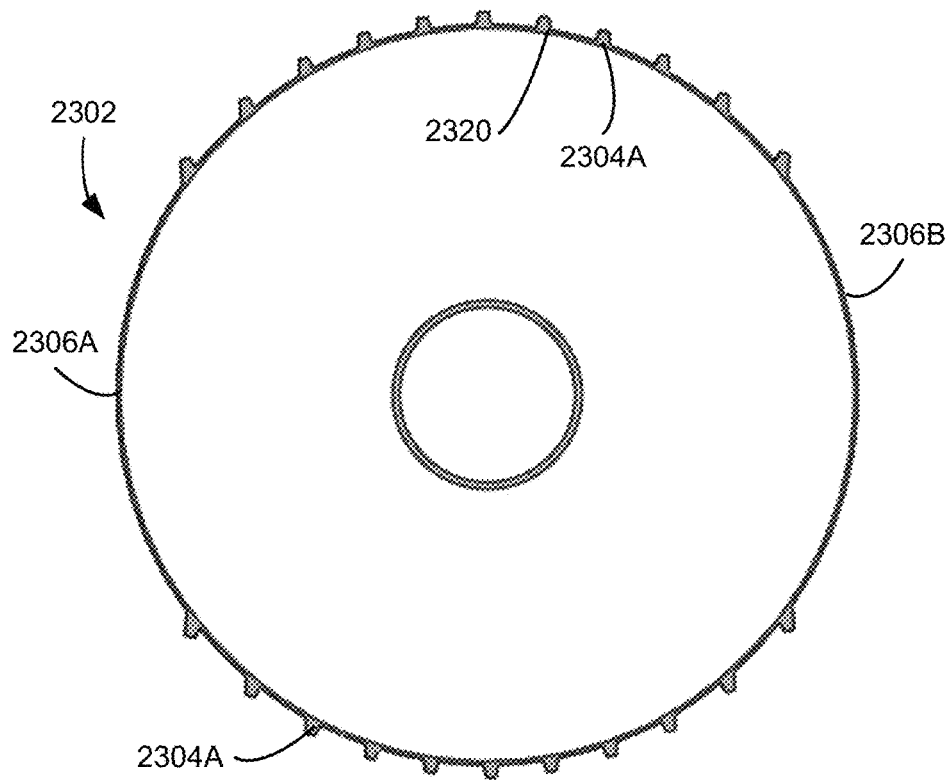

FIGS. 23A-23C are cross-sectional views of a third balloon 2302 including features to selectively collapse portions of the balloon 2302 when in the deflated state. More specifically, FIG. 23A illustrates the balloon 2302 in an unstrained state, FIG. 23B illustrates the balloon 2302 in a collapsed state, and FIG. 23C illustrates the balloon 2302 in a strained inflated state in which the balloon is inflated to a greater extent than as illustrated in FIG. 23A. As shown, the balloon 2302 generally includes textured portions 2304A, 2304B and untextured portions 2306A, 2306B extending circumferentially between the textured portions 2304A, 2304B. In at least certain implementations, the balloon 2302 may also include untextured proximal and distal ends, as included in other implementations of the present disclosure. As illustrated in each of FIGS. 23A-23C, each of the textured portions 2304A, 2304B generally includes a plurality of protrusions, such as protrusions 2320.

In contrast to textured portions 2204A, 2204B of the balloon 2202 of FIGS. 22A and 22B, in which the textured portions 2204A, 2204B becomes concave about an axis perpendicular to a longitudinal axis of the balloon 2202, the balloon 2302 is configured such that the textured portions 2304A, 2304B become concave about an axis parallel to the longitudinal axis of the balloon 2302. As illustrated in FIG. 23B, when in the collapsed state, the concavity of the textured portions is such that the protrusions 2320 are disposed within a maximum radius defined by the untextured portions 2306A, 2306B. As a result, when in the deflated state, the balloon 2302 may be inserted into and/or transported through a physiological lumen with reduced interaction between the textured portions 2304A, 2304B and an inner surface of the physiological lumen. When in an intended position, the balloon 2302 may then be inflated such that the textured portions 2304A, 2304B expand from the concave configuration, thereby causing contact between the protrusions 2320 the inner surface of the physiological lumen. Doing so increases frictional engagement between the balloon 2302 and the inner surface, up to and including frictional engagement sufficient to anchor the balloon 2302 in place within the physiological lumen.

Controlled collapsing/concavity of balloons in accordance with the present disclosure may be achieved in various ways. For example and without limitation, portions of the balloon intended to collapse or become concave (e.g., the textured portions 2204A, 2204B) may have a smaller wall thickness than other portions intended to substantially retain their shape (e.g., the untextured ends 2206A, 2206B). In other implementations, portions of the balloon intended to retain their shape may be selectively reinforced. For example, the balloon 2202 illustrated in each of FIGS. 22A and 22B includes internal ridges 2210A, 2210B disposed within the untextured ends 2206A, 2206B. During inflation and deflation, the internal ridges reinforce the untextured ends 2206A, 2206B such that the untextured ends 2206A, 2206B maintain a more consistent shape as compared to unreinforced portions of the balloon 2202, such as the textured portion 2204A, 2204B.

Figure 24:
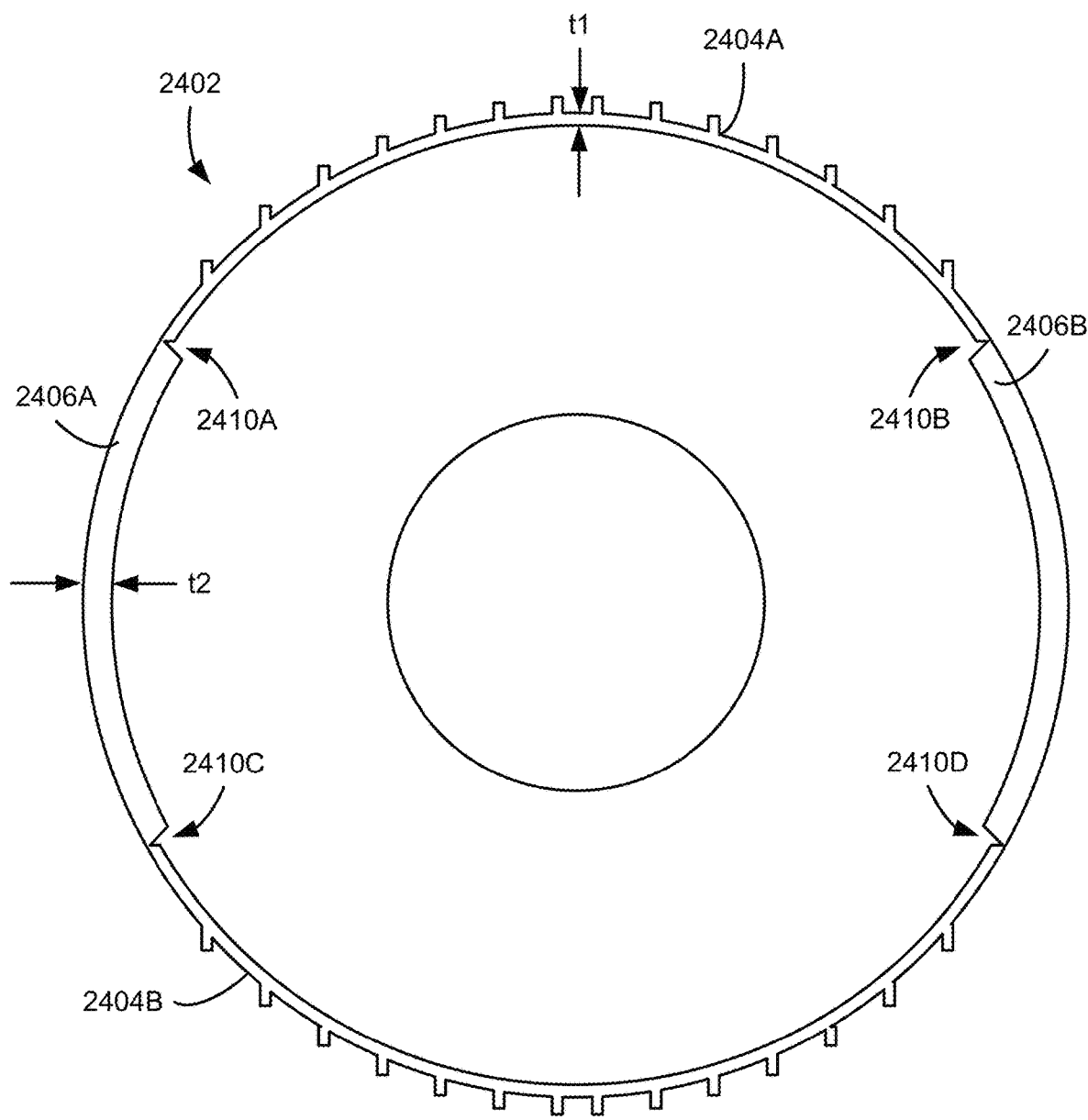
FIG. 24 is a cross-sectional view of an example balloon having varying wall thickness to facilitate controlled collapse of the balloon.

FIG. 24 illustrates an alternative structure for controlling collapse of an example balloon 2402 during deflation. The balloon 2402 includes a pair of textured portions 2404A, 2404B between which are disposed untextured portions 2406A, 2406B. As illustrated, each of the textured portions 2404A, 2404B has a first wall thickness (t1) and each of the untextured portions 2406A, 2406B has a second wall thickness (t2) that is greater than the wall thickness of the textured portions 2404A, 2404B. In one example implementation, the first wall thickness may be from and including about 100 μm to and including about 2000 μm while the second wall thickness may be from and including about 150 μm to and including about 3000 μm.

As a result, as the balloon 2402 collapses, the textured portions 2404A, 2404B will collapse and become concave prior to and to a greater extent than the untextured portions 2406A, 2406B. In certain implementations, the wall thickness of the untextured portions 2406A, 2406B may also be sufficient to prevent or substantially reduce collapse of the untextured portions 2406A, 2406B during deflation. As further illustrated in FIG. 24, controlled collapse of the balloon may also be facilitated by the use of notches 2410A-2410D or similar features that provide localized reduction of the wall thickness of the balloon 2402. For example, the notches 2410A-2410D of the balloon 2402 are formed at the transition between the textured portions 2404A, 2404B and the untextured portions 2406A, 2406B to facilitate collapse of the untextured portions 2406A, 2406B.

The specific ways in which balloons may be inflated/collapsed described above are provided merely as examples. More generally, balloons in accordance with the present disclosure may be configured to collapse and/or inflate in a non-uniform way. By doing so, different states of deflation/inflation may be used to disposed different proportions of the balloon protrusions at a maximum diameter of the balloon and/or to position different proportions of the protrusions in a substantially outwardly/radially extending direction.

Figure 2A:
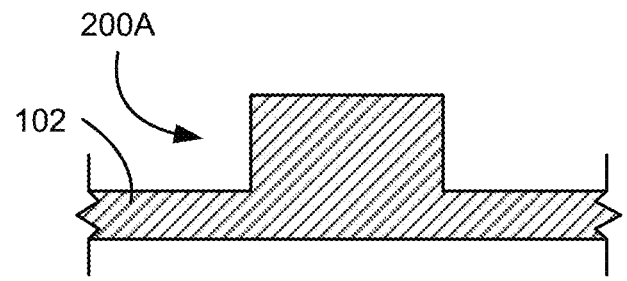
FIGS. 2A-2AD are various views of example protrusions according to the present disclosure.

FIGS. 2A-2AD are various views of example protrusions in accordance with the present disclosure. These example protrusions are shown with the corresponding balloon in an unstrained state. Accordingly, inflation of the corresponding balloons into a strained state will generally alter the shapes of the example protrusions.

Figure 2B:
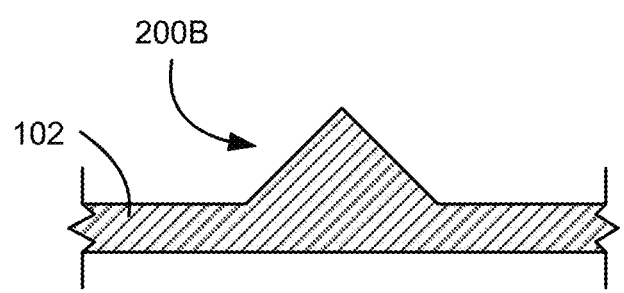
Figure 2C:
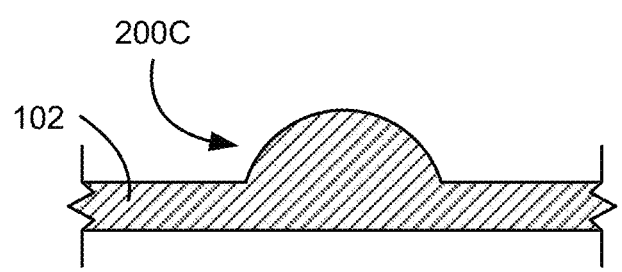
Figure 2D:
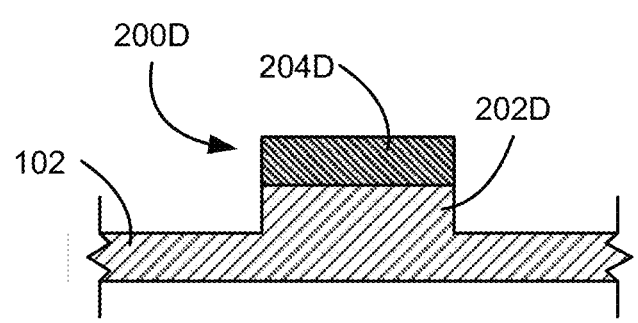

FIG. 2A illustrates a first protrusion 200A extending from the balloon 102 and having a cylindrical or rectangular shape, FIG. 2B illustrates a second protrusion 200B having a triangular or pyramidal shape, and FIG. 2C illustrates a third protrusion 200C having a rounded or hemispherical shape. FIG. 2D is a cross-sectional view of a fourth protrusion 200D composed of multiple materials.

The protrusion shapes illustrated in FIGS. 2A-2D are intended merely as examples and other protrusion shapes are possible. For example and without limitation, other implementations of the current disclosure may include protrusions having any shape, including but not limited to rectangular, square, triangular, pentagonal, heptagonal, hexagonal, pyramidal, mushroom, or spherical shape. These protrusions are solid in one example, while in other embodiments the protrusions may be hollow. The ends of the protrusions distal to the surface of the balloon 102 may also be formed in various shapes. For example and without limitation, the distal ends of the protrusions may be flat, rounded (including either of convex or concave), pointed, or mushroomed. The width/diameter of the protrusions may also vary. For example, the distal end of the protrusions may be larger in diameter than the proximal end, so as to resemble a mushroom. In other implementations, the proximal end of the protrusions may be larger in diameter than the distal end, such that the protrusions distally taper.

As noted above, FIG. 2D illustrates a protrusion 200D formed from multiple materials. More specifically, the protrusion 200D includes a first portion 202D proximal the balloon 102 and a second portion 204D distal the balloon 102. As illustrated, the first portion 202D is integrally formed with the balloon 102. The second portion 204D, on the other hand, forms a cap or tip of the protrusion 200D that may be coupled to or formed onto the first portion 202D after formation of the first portion 202D. In other implementations, each of the first and second portions 202D, 204D may be formed from different materials than the balloon 102.

The specific arrangement illustrated in FIG. 2D is intended merely as an example of a multi-material protrusion and other arrangements are possible. For example and without limitation, multi-material protrusions may be formed by embedding or implanting structural elements of a first within protrusions formed of a second material or at least partially encompassing protrusions formed from a first material with a cap, sheath, or similar element formed from a second material. It should also be appreciated that while FIG. 2D illustrates a two-material protrusion 200D, any suitable number of materials may be used to form protrusions in accordance with the present disclosure.

Figure 2E:
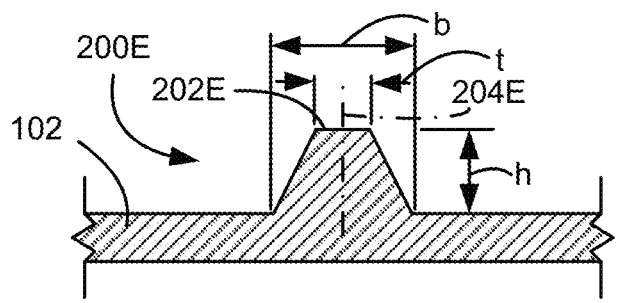
Figure 2F:
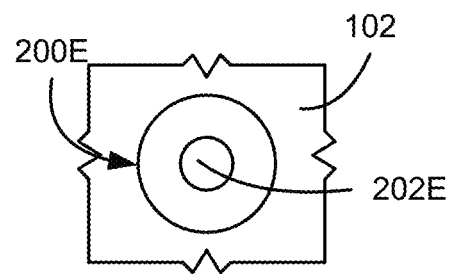

FIGS. 2E-2AD illustrate additional example protrusions that may be implemented in embodiments of the present disclosure. FIGS. 2E and 2F, for example, are a cross-sectional view and a plan view, respectively, of a protrusion 200E extending from the balloon 102 and having a frusto-conical shape. As illustrated in FIG. 2E, the shape of the protrusion 200E may be defined by a base diameter b, a height h, and a top diameter t of the protrusion 200E. Although any suitable dimension for b and h may be used, in at least certain implementations, b may be from and including about 50 μm to and including about 3000 μm, h may be from and including about 25 μm to and including about 3000 μm, and t may be from and including about 25 μm to and including about 2500 μm. Moreover, while the protrusion 200E of FIGS. 2E and 2F is illustrated as having a top 202E extending substantially perpendicular to an axis 204E of the protrusion 200E, in other implementations, the top 202E may instead be biased relative to the axis 204E. The performance characteristics of the protrusion 200E may be modified by altering various aspects of the protrusion 200E. For example and without limitation, any of the base diameter, top diameter, or height of the protrusion 200E may be varied to modify the stiffness of the protrusion 200E.

Figure 2G:
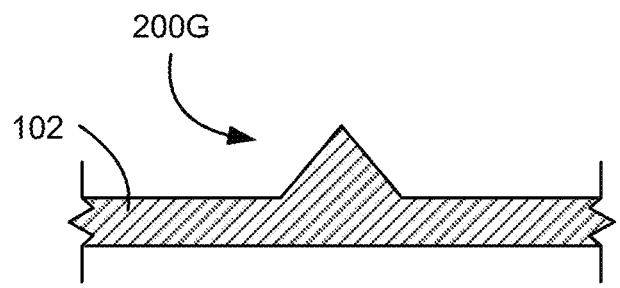
Figure 2H:
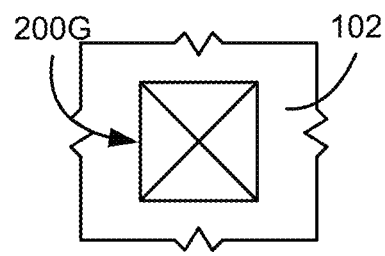
Figure 2I:
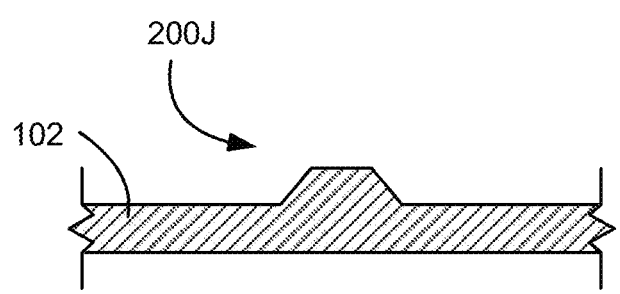
Figure 2J:
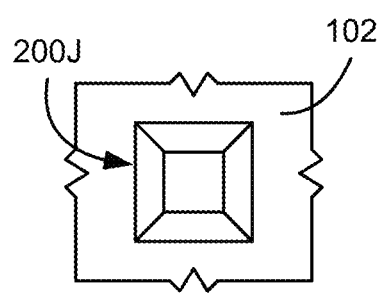
Figure 2K:
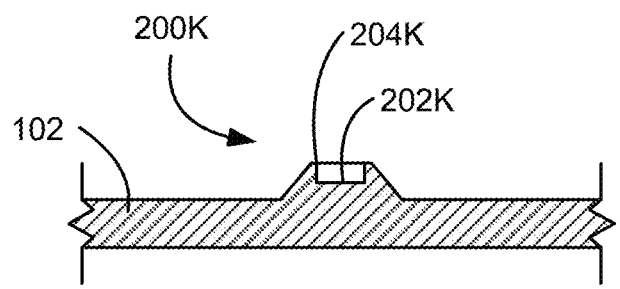
Figure 2L:
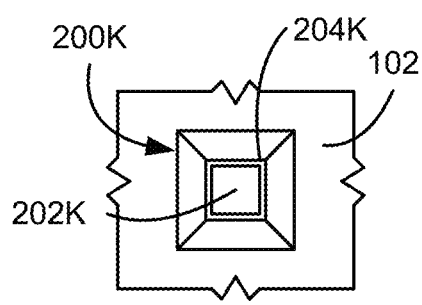
Figure 2M:
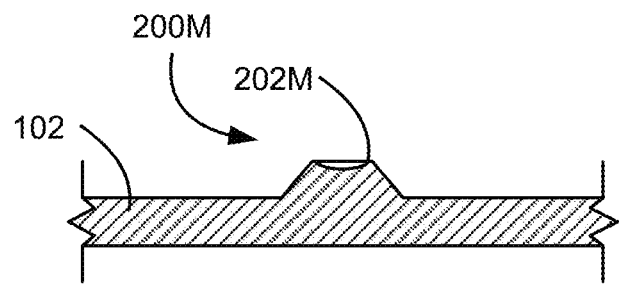
Figure 2N:
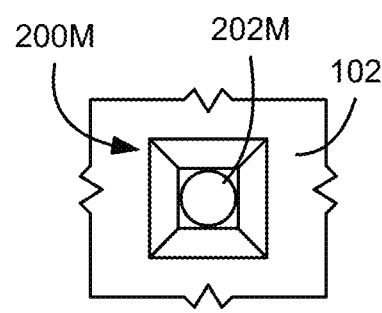

FIGS. 2G-2N illustrate various implementations of pyramidal protrusions. Specifically, FIGS. 2G and 2H are a cross-sectional view and a plan view, respectively, of a protrusion 200G extending from the balloon 102 and having a pointed, square-based pyramid shape. FIGS. 2I and 2J are a cross-sectional view and a plan view, respectively, of a protrusion 200J extending from the balloon 102 and having a truncated, square-based pyramid shape. FIGS. 2K and 2L are a cross-sectional view and a plan view, respectively, of a protrusion 200K extending from the balloon 102 and having a truncated, square-based pyramid shape including a square recess 202K extending into the protrusion 200K from a top surface 204K of the protrusion 200K. Similarly, FIGS. 2M and 2N are a cross-sectional view and a plan view, respectively, of a protrusion 200M extending from the balloon 102 and having a truncated, square-based pyramid shape including a concave top surface 202M.

Figure 2O:
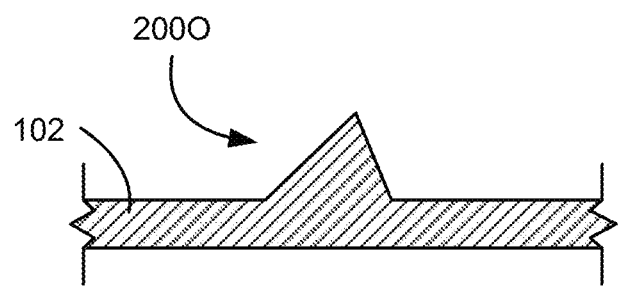
Figure 2P:
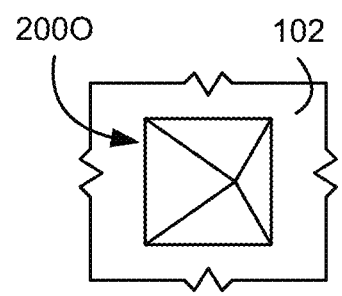
Figure 2Q:
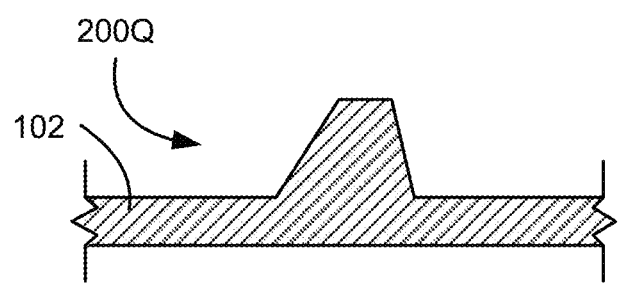
Figure 2R:
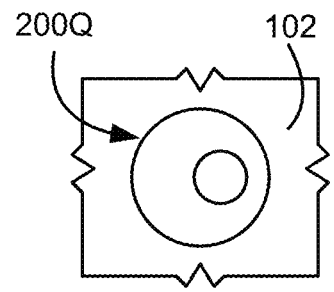

FIGS. 2O-2R illustrated example protrusions having an asymmetrical or "swept" configuration. More specifically, FIGS. 2O and 2P are a cross-sectional view and a plan view of another example protrusion 200O, the protrusion Q having a swept square-based pyramidal shape. Similarly, FIGS. 2Q and 2R are a cross-sectional view and a plan view of yet another example protrusion 200Q, the protrusion 200Q having a swept truncated conical shape. In certain implementations, such swept shapes may be the result of molding process limitations. For example, a mold for producing balloons in accordance with the present disclosure may be formed using electrical discharge machining (EDM). In such cases, a machining electrode is plunged into a mold half to form the protrusions. In applications in which the plunging path is linear and the mold half is curved, the resulting feature will inherently have a shadowed or swept shape. Nevertheless, in other implementations the swept shapes may be specifically controlled to provide improved traction, to otherwise bias the protrusions in a particular direction, to provide reinforcement in a specific direction, and the like.

Figure 2S:
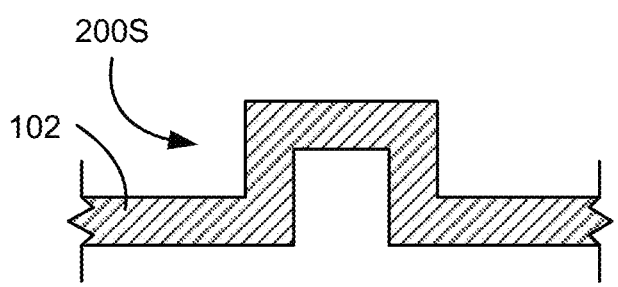

FIG. 2S is a cross-sectional view of still another example protrusion 200S. The protrusion 200S is provided to illustrate that protrusions in accordance with the present disclosure may be hollow. While illustrated in FIG. 2S as being substantially rectangular or cylindrical in shape, it should be understood that any protrusion design discussed herein may be at least partially hollow and such hollow protrusions are not limited to any specific shape or dimensions.

Figure 2T:
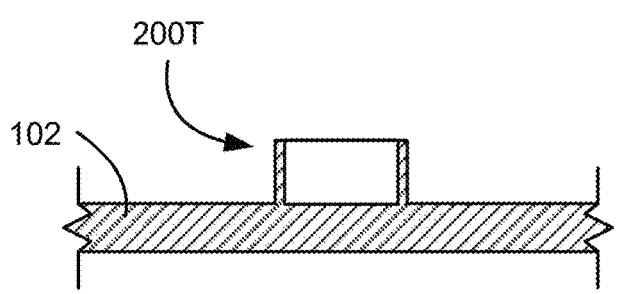
Figure 2U:
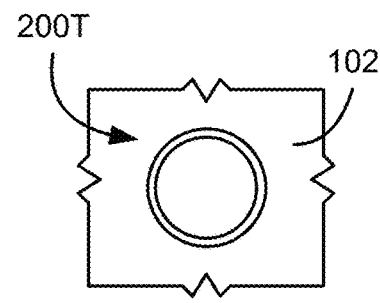

FIGS. 2T and 2U are a cross-sectional view and a plan view of another example protrusion 200T. More specifically, the protrusion 200T has a tubular cylindrical shape and is intended to illustrate an implementation of a protrusion having a tubular or thin-walled construction. Although illustrated as having a cylindrical shape, it should be understood that thin-walled/tubular protrusions similar to that illustrated in FIGS. 2T and 2U are not limited to cylindrical shapes. Rather, thin-walled or tubular protrusions may have any suitable shape.

Figure 2V:
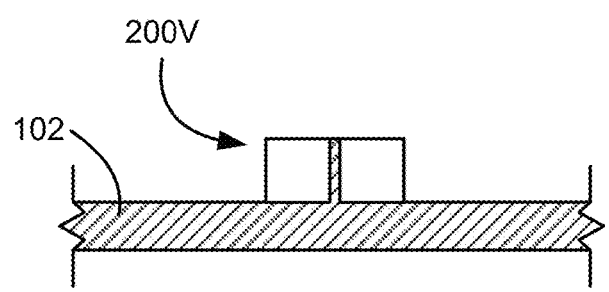
Figure 2W:
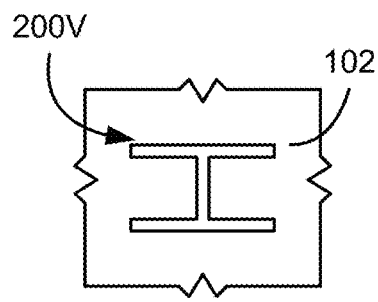

FIGS. 2V and 2W are a cross-sectional view and a plan view of still another example protrusion 200V. More specifically, the protrusion 200V has a barbell-type shape and is intended to illustrate an implementation of a protrusion formed from a series of interconnected ribs, walls, or similar structures extending from the surface of the balloon 102.

Figure 2X:
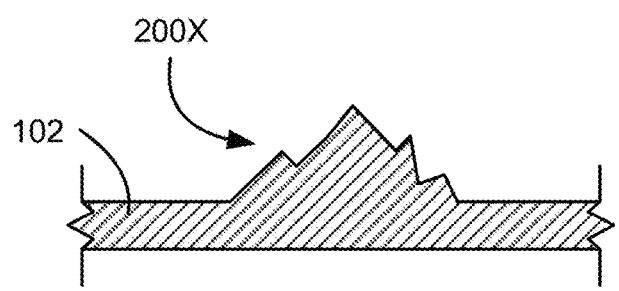

FIG. 2X is a cross-sectional view of a protrusion 200X having a jagged shape. Protrusion 200X is intended to illustrate that protrusions in accordance with the present disclosure are not limited to conventional shapes or surfaces. Rather, protrusions may be implemented having any suitable shape or surface, including random or pseudo-randomly generated shapes or surfaces.

Figure 2Y:
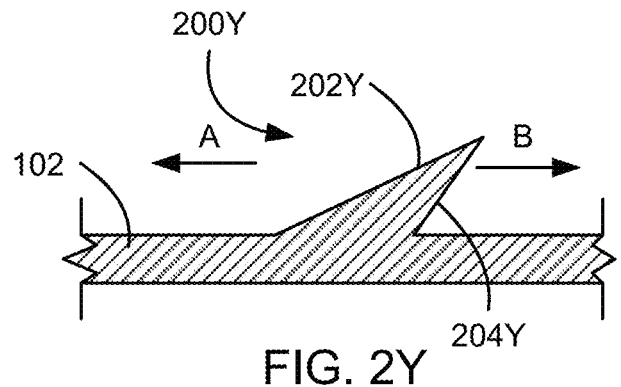

FIGS. 2Y-2AD illustrate various protrusions having a directional design. For purposes of the present disclosure, directional protrusions refer to protrusions that are specifically shaped to provide reduced friction/adhesion or improved aero- or hydrodynamic behavior in a first direction and increased friction/adhesion or reduced aero- or hydrodynamic behavior in a second direction that is generally opposite the first direction. Among other things, such protrusions designs may be beneficial for facilitating translation or movement of a balloon within a lumen in a first direction while providing increased resistance to translation or movement of the balloon in a second opposite direction.

Figure 2Z:
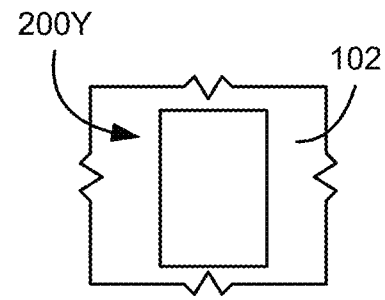
Figure 2A:
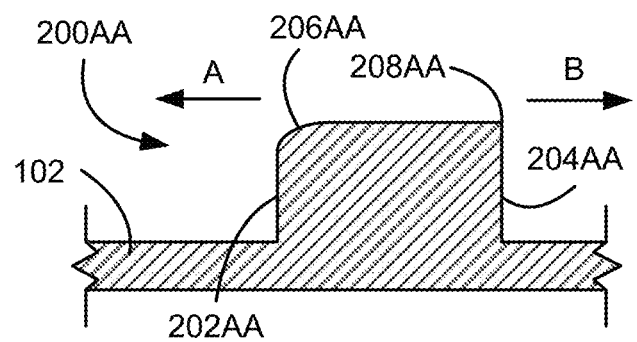
Figure 2A:
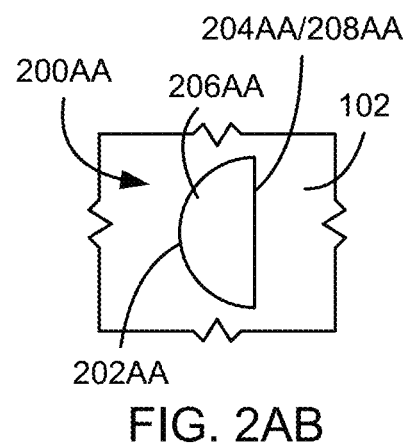
Figure 2A:
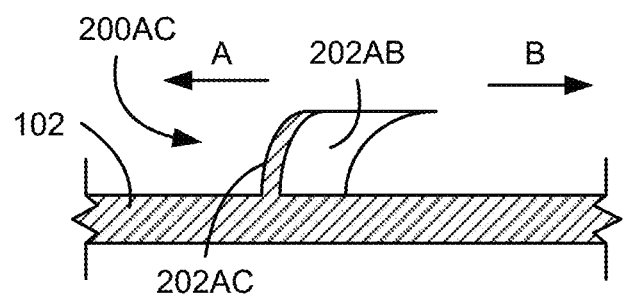
Figure 2A:
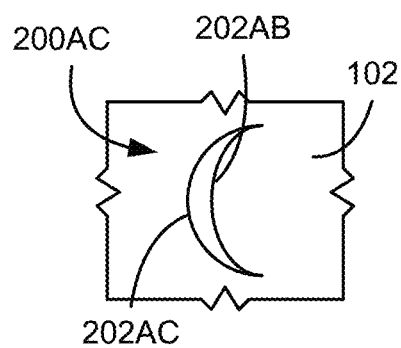

Referring first to FIGS. 2Y and 2Z, a cross-sectional and a plan view of a first directional protrusion 200Y is provided. The protrusion 200Y has a swept or saw tooth shape that provides variable resistance in opposite directions. More specifically, the shallower slope of a leading face 202Y of the protrusion provides reduced friction in a first direction a first direction (indicated by arrow A) as compared to a second, opposite direction (indicated by arrow B). In the specific implementation illustrated in FIG. 2Y, a trailing face of the protrusion 204Y is arranged such that the protrusion 200Y forms a barb or hook-like shape. However, it should be appreciated that variable directional performance may be achieved with a less aggressive design, such as the "swept" protrusions illustrated in FIGS. 2O-2R.

FIGS. 2AA and 2AB are a cross-sectional view and a plan view of a second direction protrusion 200AA having a semi-circular shape. More specifically, the protrusion 200AA includes a curved leading surface 202AA and a substantially flat tailing surface 204AA such that the protrusion 200AA provides reduced friction in a first direction (indicated by arrow A) as compared to a second direction (indicated by arrow B). Additional directional properties of the protrusion 200AA are provided by including a rounded or smoothed leading edge 206AA and a substantially sharper tailing edge 208AA. For example, in at least certain implementations, the tailing edge 208AA may have a radius from and including about 5 μm to and including about 500 μm, for example 75 μm, while the leading edge 206AA may have a radius having that is 1.1-2.0 times or greater than the radius of the tailing edge 208AA.

FIGS. 2AC and 2AD are a cross-sectional view and a plan view of a third direction protrusion 200AA having a scalloped crescent shape. More specifically, the protrusion 200AC includes a convex leading surface 202AC and a concave tailing surface 204AC such that the protrusion 200AC provides reduced friction in a first direction (indicated by arrow A) as compared to a second direction (indicated by arrow B). Similar to the protrusion 200Y illustrated in FIGS. 2Y and 2Z, the crescent shaped protrusion 200AC is also "swept" to further vary resistance between the indicated directions.

It should be understood that the protrusions illustrated in FIGS. 2A-2AD and elsewhere throughout this disclosure are intended merely as examples and should not be viewed as limiting the scope of the present disclosure. Implementations of the present disclosure may include protrusions combining features or characteristics of any of the protrusion designs discussed herein. For example and without limitation, the concave tip illustrated in FIGS. 2M and 2N may be incorporated into protrusions having any suitable base shape. Similarly, "swept" protrusion designs, as illustrated in FIGS. 2O-2R may similarly include any suitable base shape.

While illustrated in FIGS. 2A-2AD as having substantially smooth exterior surfaces, in at least certain implementations, outer surfaces of protrusions in accordance with the present disclosure may instead be selectively roughened or textured to provide additional friction/adhesion. For example and without limitation, such texturing may be applied to the protrusions by grit blasting or otherwise roughening the surfaces of the mold used to produce the protrusions. In such implementations, such additional texturing or roughening of the protrusions surfaces may be about 25 μm or less.

Figure 3:
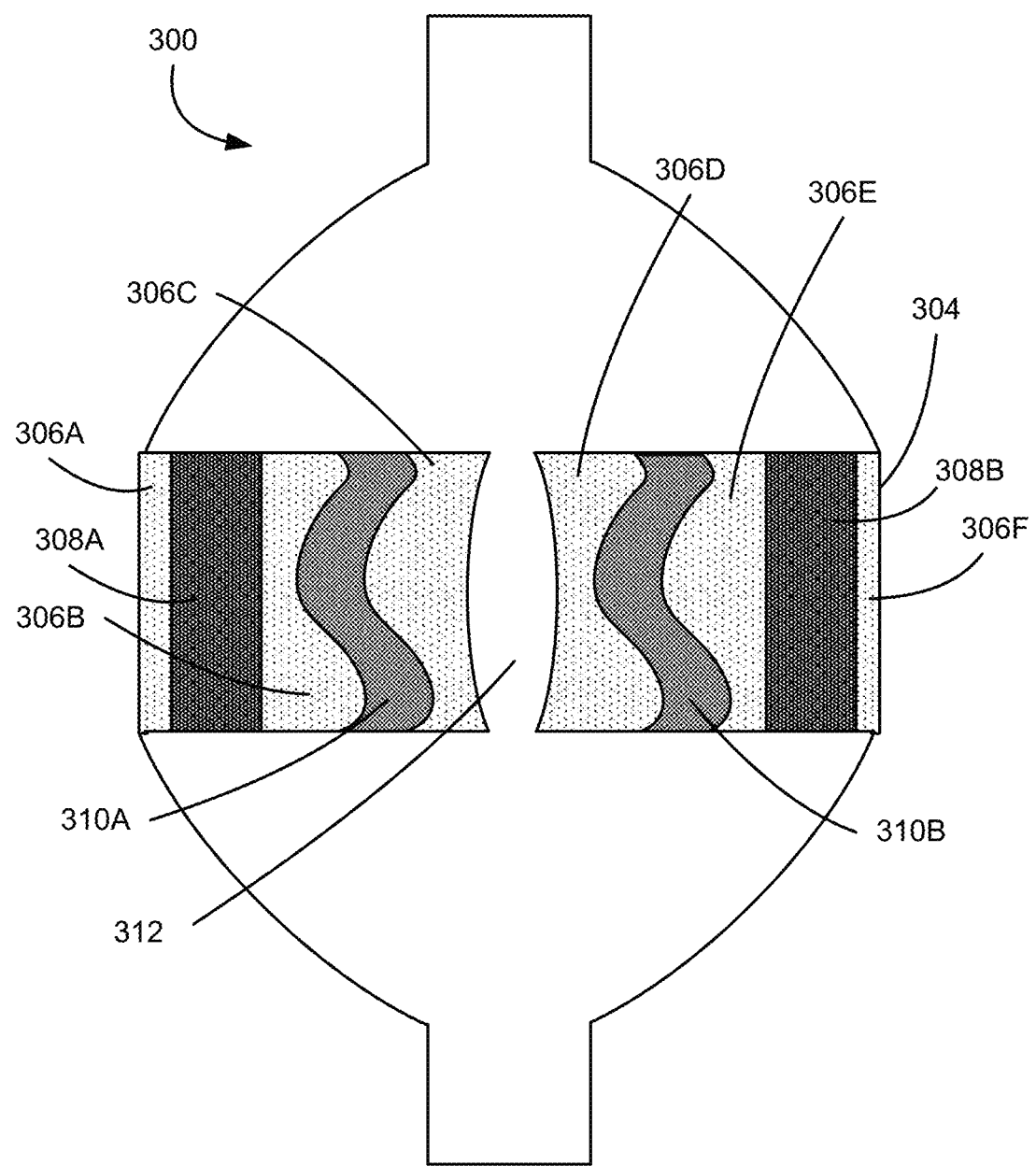
FIG. 3 is a side elevation view of an alternative balloon according to the present disclosure.

The example balloon 102 illustrated in FIGS. 1A-1E included a textured portion 104 having a substantially uniform distribution of protrusions extending therefrom. In contrast, FIG. 3 is a side elevation view of another example balloon 300 in accordance with the present disclosure in a minimally inflated state including a more complicated textured portion 304. More specifically, in contrast to the textured portion 104 of the balloon 102 illustrated in FIG. 1E, which included a substantially uniform pattern and distribution of substantially uniform protrusions, the textured portion 304 includes multiple areas 306A-312 of protrusions. More specifically, the textured portion 304 includes a first set of areas 306A-306F having a relatively low protrusion density; a second set of areas 308A, 308B having a relatively high protrusion density; a third set of areas 310A, 310B having an intermediate protrusion density; and a fourth area 312 that is substantially smooth. Although the areas are described as having different protrusion densities, it should be appreciated that each area may vary in other aspects including, without limitation, one or more of protrusion density, protrusion shape, protrusion rigidity, protrusion distribution pattern, protrusion material, and the like. Similarly, as illustrated in FIG. 3, each area of the textured portion 304 may vary in size and shape.

Referring back to the example medical device 100 of FIGS. 1A-1E, the height of the protrusions 106 may vary in different applications of the present disclosure. For example and without limitation, in at least one implementation the protrusions 106 may be from and including about 5 μm to and including about 700 μm tall when the balloon 102 is in either an uninflated or inflated state. In another implementation, the protrusions may be from and including about 15 μm to and including about 200 μm tall. In yet other implementations, the protrusions may be from and including about 30 μm to and including about 110 μm tall. In at least one specific implementation, the protrusions are from and including about 300 μm to and including about 500 μm to enable the protrusions to penetrate mucosal layers of the physiological lumen. In contrast, in applications in which a mucosal layer may not be present (e.g., cardiac applications), the protrusions may be from and including about 50 μm to and including about 100 μm in height. Although implementations of the present disclosure are not limited to any specific protrusion heights, in at least certain implementations, the protrusions may have an overall height up to and including about 5000 μm or greater. Specific implementations of the present disclosure may also include protrusions having varying heights. Also, individual protrusions may have different portions extending to different heights (e.g., having a crenellated or other top having varying height).

As noted above, protrusion height for a given application may vary depending on the type of physiological lumen within which a balloon is being deployed and, more specifically, the thickness of any fluid layers that may be present. For example and without limitation, the mucosal layer of the colon is generally around 800-900 μm thick while that of the ileum is generally around 400-500 μm thick. Accordingly, to adequately penetrate the respective mucosal layers, balloons intended for deployment in the colon may generally be provided with protrusions of greater length as compared to those of balloons intended for deployment in the ileum. Similar considerations may be made for fluidic layers (e.g., other forms of mucus, sinus fluid, perspiration, etc.) that may be present in other physiological lumens within which balloons according to the present disclosure may be deployed.

Similar to height, the cross-sectional width (e.g., the diameter in the case of protrusions having a circular or ovoid cross-section) of each protrusion may vary. For example and without limitation, in one implementation the protrusions have a cross-sectional width from and including about 5 μm to and including about 1000 μm when the balloon 102 is in either the uninflated or inflated state. In another implementation the protrusions have a cross-sectional width from and including about 25 μm to and including about 300 μm. In yet other embodiments the protrusions have a cross-sectional width from and including about 70 μm to and including about 210 μm. In still another implementation the protrusions have a cross-sectional width from and including about 600 μm to and including about 1000 μm. In yet another implementation the protrusions have a cross-sectional width from and including about 300 μm to and including about 500 μm. In another implementation, the protrusions have a cross-sectional width from and including about 150 μm to and including about 250 μm. In at least one specific implementation, the protrusions have a cross-sectional width of about 400 μm. Implementations of the present disclosure may also include protrusions having varying diameters. Also, individual protrusions may have different portions having different diameters (e.g., a tapering shape). Although protrusion cross-sectional width for implementations of the present disclosure are not limited to any particular ranges or values, in at least certain implementations, the protrusions may have an overall cross-sectional width up to and including about 5000 μm or greater.

In certain implementations, the overall proportions of a protrusion may instead be defined according to an aspect ratio relating the height of the protrusion to the cross-sectional width/diameter of the protrusion. Although any suitable aspect ratio may be used, in one example implementation, the aspect ratio is less than about 5. In another example implementation, the aspect ratio may be from and including about 0.05 to and including about 10. In yet another example implementation the aspect ratio may be from and including about 0.1 to and including about 5.0. In another example implementation the aspect ratio may be from and including about 0.5 to and including about 1.0. In still another example implementation, the aspect ratio may be from and including about 1.0 to and including about 10.0. In another implementation, the aspect ratio may be from and including about 0.1 to and including about 1. In still another implementation, the aspect ratio may be from and including about 1 to and including about 2. In yet another example implementation, the aspect ratio may be about 0.5, about 1.0, or about 2.0. It should also be appreciated that the aspect ratio for protrusions within a given implementation of the present disclosure may vary such that a first set of protrusions of a balloon conforms to a first aspect ratio while a second set of protrusions for the same balloon conforms to a second aspect ratio. Moreover the cross-sectional width/diameter of the protrusion for purposes of determining an aspect ratio may be any measure of cross-sectional width/diameter. For example, the cross-sectional width/diameter may be the maximum cross-sectional width/diameter of the protrusion, the minimum cross-sectional width/diameter of the protrusion, an average cross-sectional width/diameter of the protrusion, or the cross-sectional width/diameter of the protrusion at a particular location along the length of the protrusion.

The protrusions may also be configured to have a particular stiffness to avoid inadvertent bending or deformation while still allowing engagement of the protrusions with biological tissue. In at least certain implementations, the protrusions are formed such that they have a stiffness that is at least equal to the tissue with which the protrusions. For example, in certain implementations, the stiffness of the protrusions is from and including about 1.0 to and including 2.0 times that of the tissue with which it is to engage. The stiffness may also be expressed as a modulus of elasticity of the material from which the protrusions are formed. For example, in at least some implementations, the protrusions are formed from a material having a modulus of elasticity from and including about 50 kPa to and including about 105 kPa. In other implementations including stiffer protrusions, the protrusions may be formed of a material having a modulus of elasticity from and including about 0.8 MPa to and including about 2.0 MPa.

In certain implementations, protrusions of balloons in accordance with the present disclosure may be configured to deform in response to a strain being applied to the balloon. Such deformation may then be used to dynamically control and adjust traction between the balloon and biological tissue.

Figure 4A:
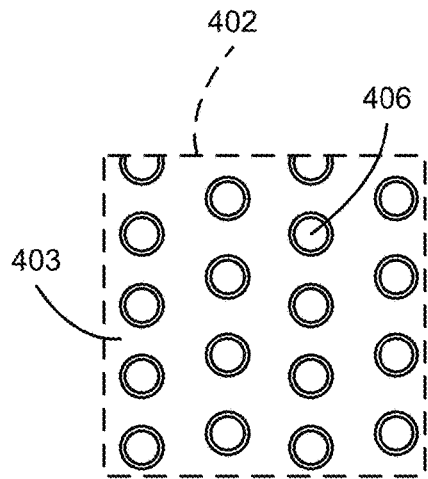
FIG. 4A is a schematic illustration of a textured portion of a balloon according to the present disclosure in a first state of strain.
Figure 4B:
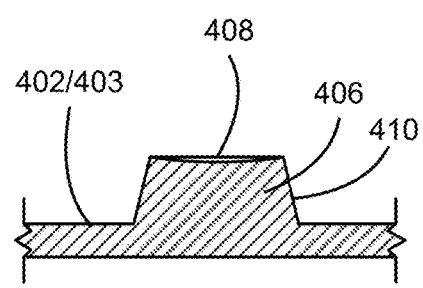
FIG. 4B is a cross-sectional view of a protrusion of the balloon of FIG. 4A.
Figure 5A:
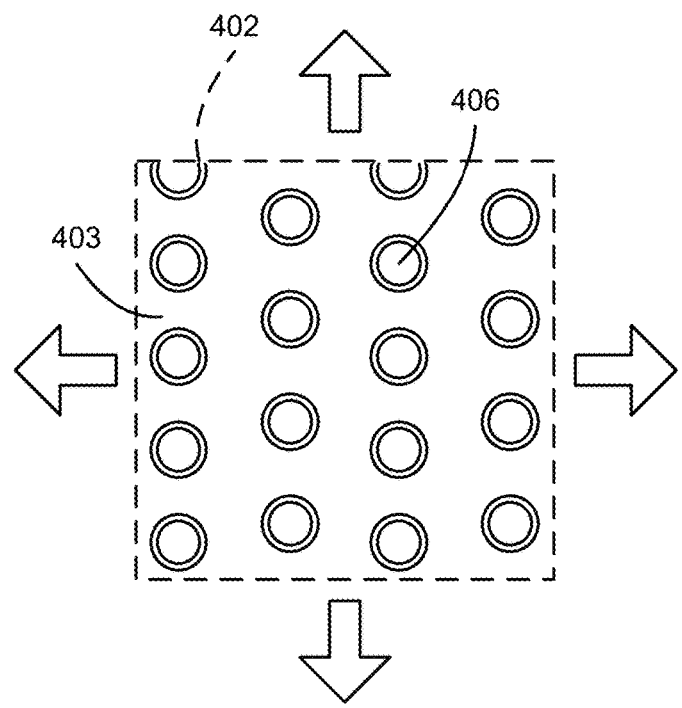
FIG. 5A is a schematic illustration of the textured portion of the balloon of FIG. 4A in a second state of strain.
Figure 5B:
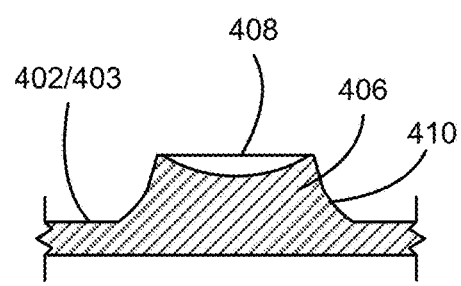
FIG. 5B is a cross-sectional view of the protrusion of FIG. 4B when the balloon of FIG. 4A is in the second state of strain.

FIG. 4A illustrates a portion of a balloon 402 or similar structure in a first state of strain. In certain applications, the first state of strain may correspond to an unstrained state or, alternatively, may correspond to a state in which a first strain is applied to the balloon 402. As shown, the balloon 402 includes multiple protrusions, such as protrusion, 406 distributed across and extending from a surface 403 of the balloon 402. As illustrated in FIG. 4B, the protrusions 406 may, in certain implementations, have a frustoconical shape. FIG. 5A illustrates the portion of the balloon 402 in a second state of strain, in which a strain greater than that of the first state of strain is applied to the balloon 402. As shown in FIG. 5A, in at least some applications, the applied strain when in the second state of strain may be biaxial. Such strain may result, for example, from inflation of the balloon 402. As illustrated in FIG. 5A, the application of strain generally results in both the distance between adjacent protrusions increasing as well as a stretching/deformation of the protrusions. FIG. 5B is a cross-sectional view of the protrusion 406 when a biaxial strain is applied to the balloon 402. As illustrated, the frustoconical shape of the protrusion 406 deforms under the biaxial strain. In particular, each of a top surface 408 and side wall 410 of the protrusion 406 become increasingly concave in response to the application of biaxial strain.

The term "biaxial strain" is generally used herein to refer to a strain applied along two axes which, in certain implementations, may be perpendicular to each other. In certain cases, the biaxial strain may be approximately equal along each axis. For example, strain applied to the balloon may be equal in each of a longitudinal direction and a transverse direction. However, in other implementations, strain may be applied unequally along the axes, including strain resulting in non-uniform deformation of the protrusions (e.g., elongation of compression primarily along a single axis). Moreover, sufficient deformation of the protrusions may also be achieved by application of a uniaxial strain or a multiaxial strain other than a biaxial strain. Accordingly, while the examples described herein are primarily discussed with reference to a biaxial strain resulting in variations in frictional and adhesive engagement resulting from deformation of the protrusion, implementations of the present disclosure are more generally directed to variations in frictional and adhesive engagement from deformation of the protrusions in response to any applied strain.

FIGS. 6A and 6B are cross-sectional views of the protrusion 406 illustrating further details of the protrusion in a strained and unstrained state, respectively. As illustrated in FIG. 6A, when in the unstrained state, the protrusion 406 has a top diameter (D1) corresponding to the top surface 408 of the protrusion and a base diameter (D2) corresponding to a base 412 of the protrusion 406. The top surface 408 of the protrusion 406 is shown as being disposed at a maximum height (H). The top surface 408 is also shown as being concave and having a concavity defined by a radius of curvature (R). The top surface 408 of the protrusion reaches a height (H) relative to the surface 403 of the balloon 402. It should be appreciated that while the top surface 408 of the protrusion is shown in FIG. 6A as being concave, in other implementations, the top surface 408 may be substantially flat. Also, while the top diameter D1 and base diameter D2 are illustrated in FIG. 6A as being different, in other implementations D1 and D2 may be equal such that the protrusion 406 is substantially cylindrical in shape.

As shown in FIG. 6B, the protrusion 406 may deform in response to a strain applied to the balloon 402. In particular, each of the top diameter (D1) and the base diameter (D2) may expand to a second base diameter (D1') and a second base diameter (D2'), respectively. The radius of curvature (R) of the top surface 408 may also decrease to a second radius of curvature (R'), thereby causing the top surface 408 to become increasingly concave. In addition to the foregoing dimensional changes, the overall height of the protrusion 406 may change from the initial height (H) to a second height (H').

As illustrated in FIGS. 6A and 6B, in at least some implementations of the present disclosure, each protrusion may include a lip or edge 414 at the transition between the side wall 410 and the top surface 408. In general, a relatively sharp lip or edge 414 may allow the protrusions to more readily engage the wall of the physiological lumen and may also facilitate penetration of mucosal or other layers that may be present on the wall. Accordingly, in at least some implementations, the edge 414 may have a radius of no more than about 3 μm.

The initial dimensions of the protrusion 406 may vary. For example, in certain implementations the unstrained upper diameter (D1) of the protrusion may be from and including about 100 μm to and including about 700 μm; the unstrained lower diameter (D2) of the protrusion may be from and including about 100 μm to and including about 750 μm; the unstrained height (H) of the protrusion may be from and including about 100 μm to and including about 700 μm; and the unstrained radius of curvature (R) of the top surface 408 of the protrusion may be from and including about 1 mm to and including about 2 mm. Similarly, in certain implementations, the strained upper diameter (D1') of the protrusion may be from and including about 375 μm to and including about 750 μm; the strained lower diameter (D2') of the protrusion may be from and including about 405 μm to and including about 825 μm; the strained height (H') of the protrusion may be from and including about 200 μm to and including about 400 μm; and the strained radius of curvature (R') of the top surface 408 of the protrusion may be from and including about 500 μm to and including about 750 μm. In one specific example, the D1 may be about 250 μm, D2 may be about 270 μm, H may be about 500 μm, and R may be about 1.5 mm. In the same example, the balloon 402 may be configured to be strained such that D1' can be up to about 375 μm, D2' can be up to about 400 μm; H' may be decreased down to about 450 μm, and R' may be decreased down to about 500 μm. In other implementations, deformation of the protrusion 406 in response to a strain applied to the balloon 402 may instead be based on a change in the surface area of the protrusion 406. For example and without limitation, the balloon 402 may be configured such that the surface area of the protrusion 406 may increase up to about 25%.

During experimental testing, it was observed that separation force between a piece of material including protrusions similar to the protrusion 406 of FIGS. 6A and 6B and a flexible probe simulating biological tissue varied with the degree of biaxial stain applied to the material. More specifically, the probe was first made to contact the material sample, causing the probe to adhere to the material sample. The probe was then withdrawn from contact with the material sample. The force required to affect such separation was measured and observed to vary non-linearly with the degree of biaxial strain applied to the material sample.

As indicated in FIG. 6A, the protrusion 406 may be further characterized by the sharpness of the edge 414 at the transition between the side wall 410 and the top surface 408 of the protrusion 406. Although the edge 414 is not limited to specific degrees of sharpness, testing has indicated that particular sharpness ranges can be advantageous in fixing balloons in accordance with this disclosure within a physiological lumen, particular in the presence of mucus and other similar fluids that may be secreted or disposed along the inner surface of the physiological lumen. More specifically, sufficient sharpness of the edge 414 appears to facilitate penetration through layers of mucus (or similar fluids) to facilitate engagement between the balloon and inner wall of the lumen. Accordingly, in at least certain implementations, the edge 414 between the side wall 410 and the top surface 408 may have a radius from and including about 25 μm to and including about 500 μm, for example 75 μm. In other implementations, the radius is not greater than about 25 μm.

Figure 7:
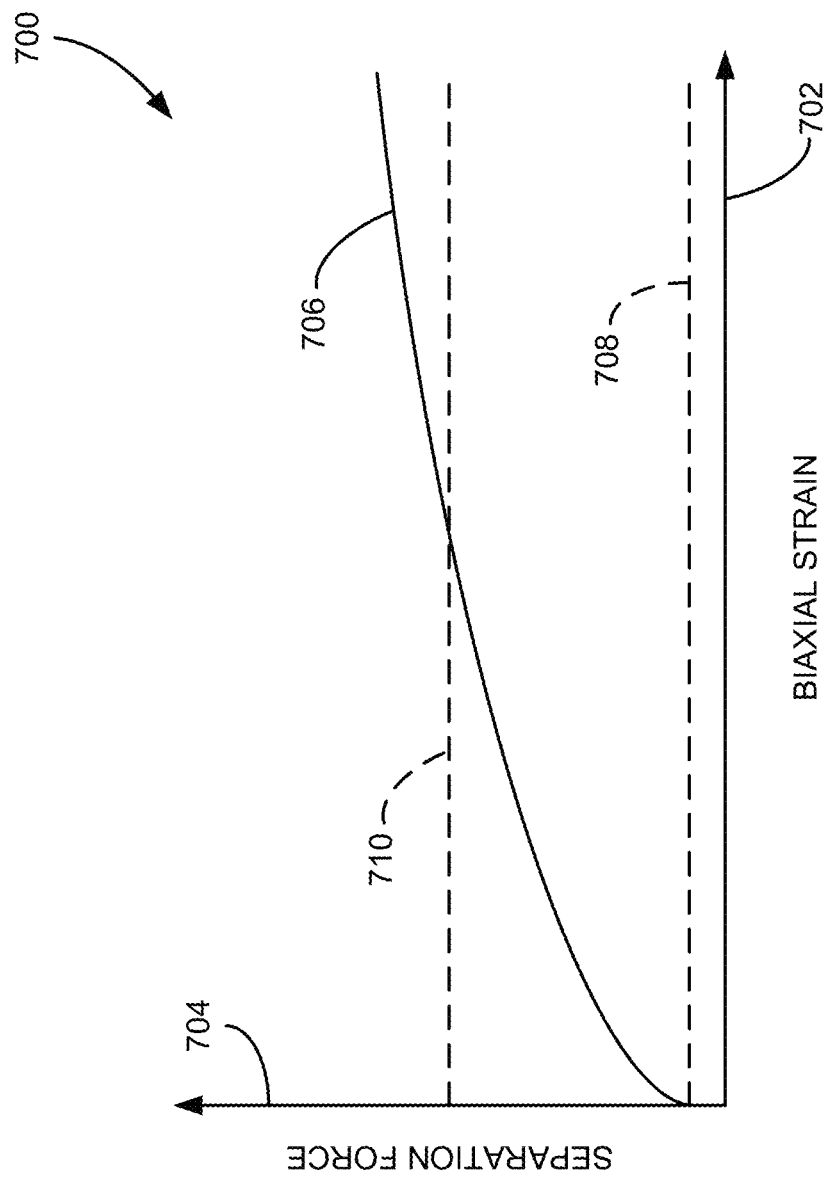
FIG. 7 is a graph illustrating an example relationship between separation force and a strain applied to a balloon in accordance with the present disclosure.

FIG. 7 is a graph 700 summarizing the experimental findings regarding the relationship between separation force and biaxial strain. More specifically, the graph 700 includes a first axis 702 corresponding to biaxial strain and a second axis 704 corresponding to the measured separation force when separating the probe and material sample. As indicated by line 706, the separation force varied in a non-linear fashion in response to changes in biaxial strain.

The graph 700 further indicates a base separation force line 708 corresponding to the separation force when the material sample is unstrained. The graph further includes a "flat" separation force line 710 corresponding to a second material sample substantially similar to the tested material sample but lacking any protrusions.

As illustrated in the graph 700, the separation force for the material having the protrusions may be varied to have a range of values by changing the biaxial strain applied to the material. For example, by applying no or relatively low biaxial strain, the material with protrusions may actually be made to have less separation force (i.e., be made to be less frictional and/or adhesive) than a flat sheet of the same material. However, as biaxial strain is increased friction and adhesion also increase such that, at a certain level of biaxial strain, the separation force of the material including protrusions may be made to exceed that of a flat sheet of the same material.

As shown in the graph 700, this may, in certain implementations, reduce the separation force when unstrained as compared to separation force of a flat material sheet. However, as strain is increased, the separation force may increase above that of the flat sheet. In other words, by selectively applying biaxial strain to the material sample, separation force may be varied, providing physicians with increased control and more reliable engagement for medical devices incorporating balloons in accordance with the present disclosure.

The specific example discussed in FIGS. 4A-7 generally includes protrusions having a flat or partially concave top surface that, when a strain is applied, causes the protrusions to become increasingly concave, thereby increasing their surface area. In other implementations of the present disclosure, the protrusions may instead include a rounded/convex or similar top surface such that when a strain is applied, the top surfaces of the protrusions at least partially flatten. Such flattening may result in a reduction of the surface area and, as a result, a change (generally a reduction) in the separation force between the protrusions and the physiological lumen. Accordingly, whereas in the previous examples a strain is applied to increase protrusion surface area to increase separation force, strain may also be used to decrease protrusion surface area and, as a result, decrease separation force. In either case, however, strain is used as the primary mechanism for altering the shape and the result separation force of the protrusions.

The separation force between the balloon and the physiological lumen may vary across different implementations of the present disclosure and across different states of inflation for any given implementation. However, in at least some implementations, the balloon may be configured to have a separation force less than about 5 N when the balloon is in its deflated state (e.g., as illustrated in FIGS. 1A-1B) to facilitate translation of the balloon along the physiological lumen with minimal adhesion and friction. In other implementations, the separation force when in the deflated state may be less than about 3 N. In a specific example, the separation force in the deflated state may be about 1 N. The balloon may also be configured to have a particular separation force in a minimally inflated state in which the balloon substantially engages the physiological lumen. For example, in at least some implementations, the separation force in the minimally inflated state may be from and including about 10 N to and including about 30 N. In other implementations, the separation force in the minimally inflated state may be from and including about 15 N to and including about 25 N. In one specific implementation, the separation force in the minimally inflated state may be about 20 N.

As previously discussed, in at least some implementations, a strain on the balloon may be applied or modified (e.g., by inflating or deflating the balloon) to modify the adhesive and frictional characteristics of the balloon and, as a result, the separation force between the balloon and physiological lumen. In one implementation, the separation force relative to a minimally inflated state may be reduced to 1% or lower by deflating the balloon and up to and including 200% by overinflating and straining the balloon. In another implementation, the deflated balloon may have a separation force of less than about 5% of the minimally inflated state and a maximum of about 150% by straining the balloon. In still another example implementation, the balloon may have a lower bound separation force of less than about 5% of the minimally inflated state and a maximum of about 125% by straining the balloon. Accordingly, in at least one specific example, the balloon may have a separation force of about 20 N in the inflated state, about 1 N in the deflated state, and about 25 N in a maximum strained state.

Figure 8:
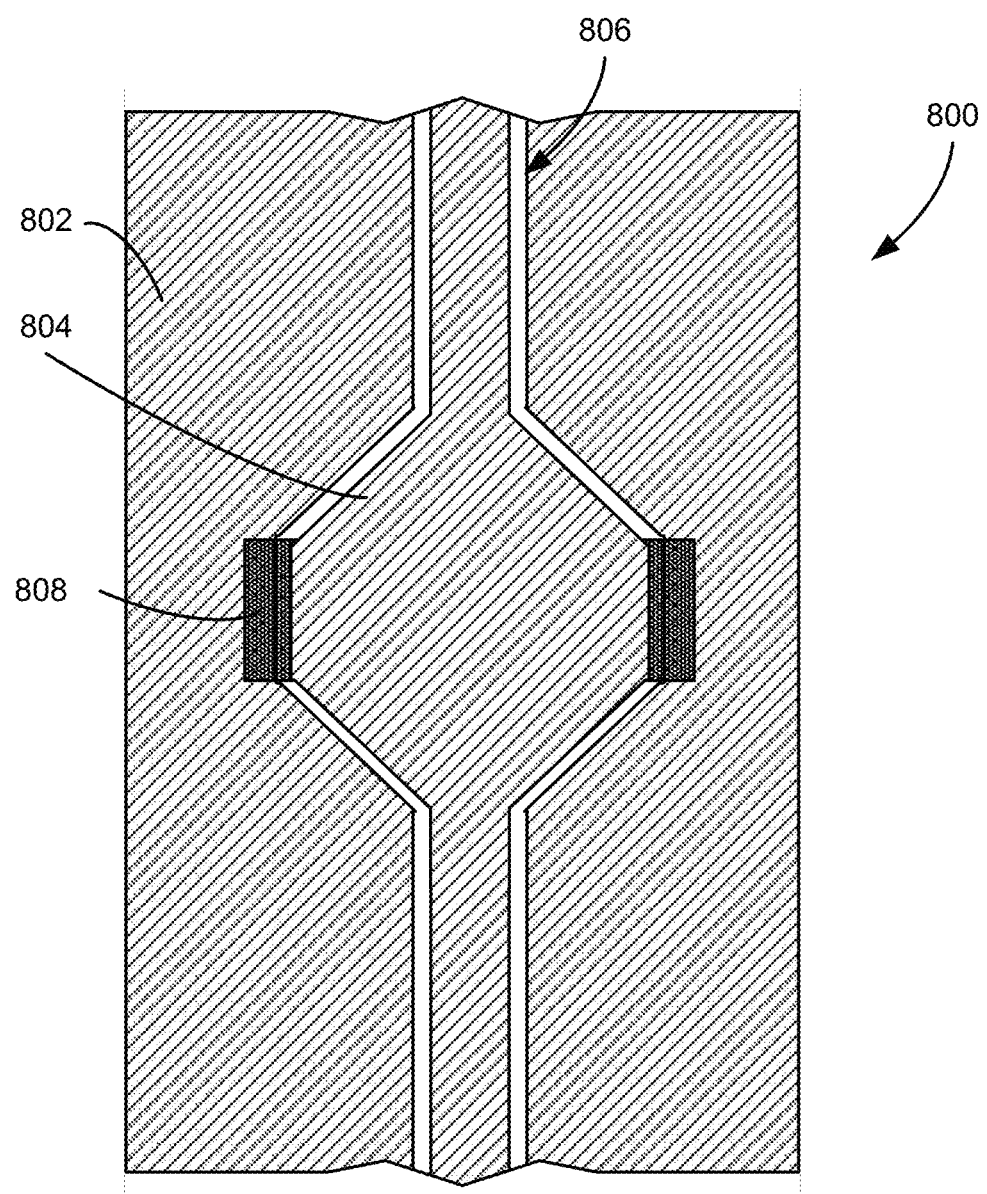
FIG. 8 is a cross-sectional view of a first mold for manufacturing balloons in accordance with the present disclosure.

As previously noted, balloons in accordance with the present disclosure may be manufactured in various ways. For example, in at least one implementation, balloons including protrusions as discussed above may be manufactured through a casting process. FIG. 8 illustrates an example mold 800 for use in such a casting process. As illustrated the mold 800 includes an outer mold piece 802 within which an inner mold piece or core 804 is disposed. The combination of the outer mold piece 802 and the core 804 defines a cavity 806 providing the general shape of the balloon to be molded.

In addition to the outer mold piece 802 and the core 804, the mold 800 includes an insert 808 for forming protrusions on the balloon during casting. The insert 808 is separately formed to have the pattern and distribution of protrusion to be included on the final balloon. The insert 808 may be manufactured in various ways including, without limitation, machining, 3D printing, microlithography, or any other similar manufacturing process. Once formed, the insert 808 may be disposed within and coupled to the outer mold piece 802. In certain implementations, the insert 808 may be formed from a semi-rigid material such as, but not limited to, Kapton® or other polyimide material, silicone, latex, or rubber.

During the casting process, balloon material (such as but no limited to ECOFLEX® 50) is poured into the cavity and allowed to set. In certain implementations, a vacuum is also applied to the mold 800 to remove air from the mold cavity 806 and to facilitate the material poured into the cavity 806 to take on the shape of the mold cavity 806, including the protrusions defined by the mold insert 808.

In certain implementations, the overall thickness of the balloon may be modified by changing the thickness of the cavity 806. For example, the outer mold piece 802 may be configured to receive cores of varying sizes such that the thickness of the cavity 806 defined between the outer mold piece 802 and the core 804 may be modified by swapping cores into the mold 800.

Although illustrated in FIG. 8 as having a substantially uniform width, the cavity 806 defined between the outer mold piece 802 and the core 804 may also be non-uniform such that the cavity 806 is wider at certain locations within the mold 800. Accordingly, any balloon formed using the mold 800 will have corresponding variations in its thickness. By varying the thickness of the balloon, various characteristics may be imparted to the balloon. For example, the thickness of certain locations of the balloon may be increased to improve the overall durability and strength of the locations. In other cases, the thickness of the balloon may be varied such that reinforced regions of the balloon are formed that cause the balloon to collapse and/or expand in a particular way. Such reinforced regions may also cause the balloon to assume a particular shape in any of a deflated state, partially inflated state, or fully inflated state.

Figure 9:
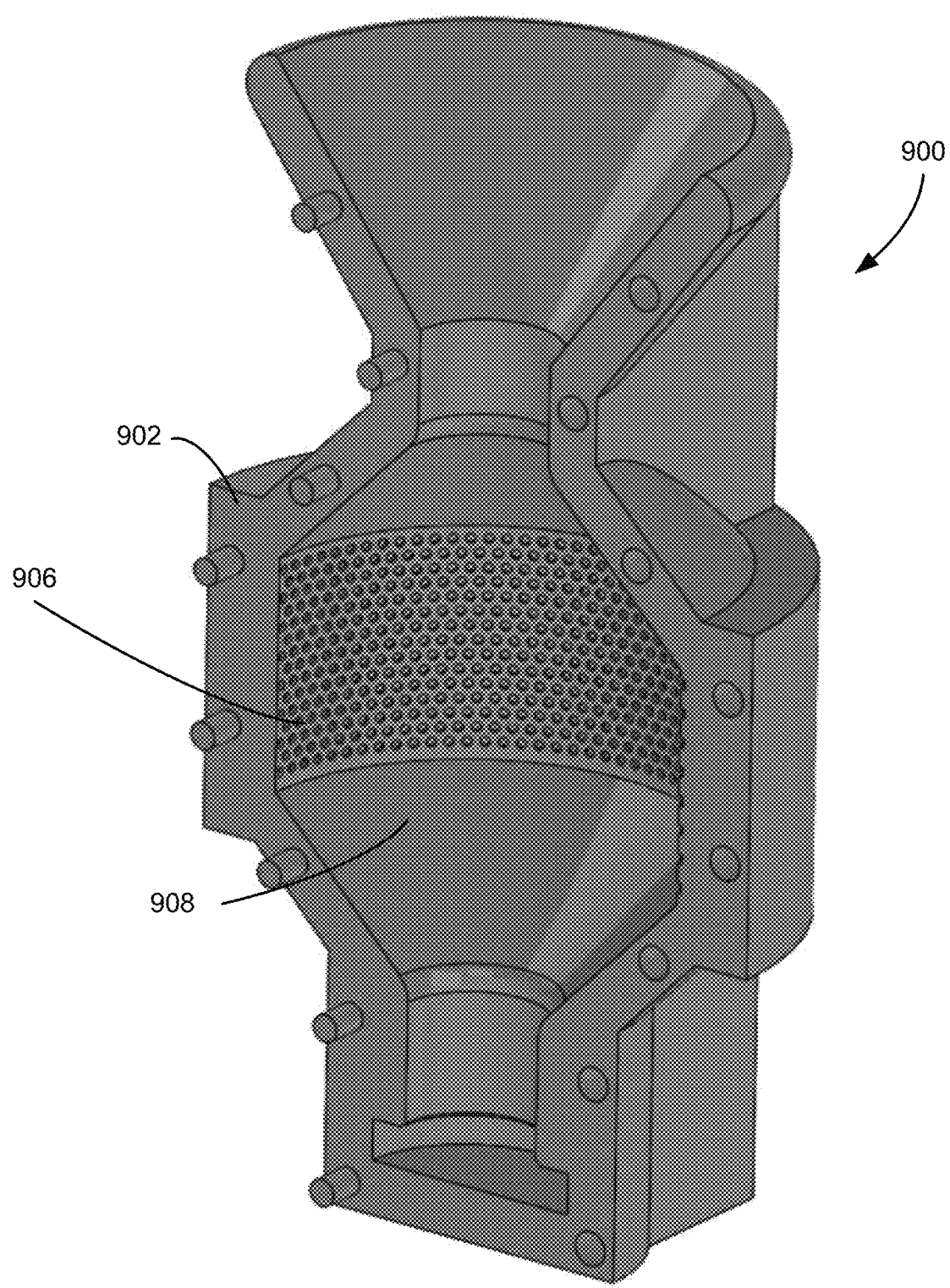
FIG. 9 is an isometric view of a second mold for manufacturing balloons in accordance with the present disclosure.

FIG. 9 is an isometric view of an alternative mold 900 for use in manufacturing balloons in accordance with the present disclosure. The mold 900 includes an outer mold piece 902 within which an inner mold piece or core (not shown) may be disposed. In contrast to the mold 800 of FIG. 8 in which a removable insert 808 is used to form the balloon protrusions, the outer mold piece 902 includes voids 906 formed directly into an inner surface 908 of the outer mold piece 902 that are used to form the protrusions during the casting process.

As discussed above, in at least some implementations, balloons in accordance with the present disclosure may be formed using a casting process. Such casting processes may include piece casting, slush casting, drip casting, or any other similar casting method suitable for manufacturing a hollow article. In a slush casting process, for example, an amount of material may be added to the mold and slushed to coat the internal surface of the mold prior to the material setting. Other fabrication methods may also be implemented including, without limitation, various types of molding (e.g., injection molding) and extrusion processes.

While previous fabrication methods included integrally forming the protrusions with the balloon, in other implementations the protrusions may instead be formed onto a previously formed balloon. For example, in at least one other fabrication method, a base balloon may first be formed. The protrusions may then be formed or coupled to the balloon using a subsequent process. In one example fabrication method, the base balloon is extruded and then the protrusions are then added to the base balloon using a spray method. In another example fabrication method, the base balloon is formed using a first casting or molding process and, once the base balloon is set, a second casting or molding process (e.g., an over-molding process) is applied to form the protrusions on the exterior surface of the base balloon.

As previously discuss in the context of FIGS. 1A-1E, balloons in accordance with the present disclosure may be implemented for use in various medical devices. FIGS. 10-16 are schematic illustrations of various example medical devices and configurations of such medical devices including balloons of the present disclosure. It should be appreciated that the medical devices provided are merely example devices and are therefore non-limiting. More generally, balloons in accordance with the present disclosure may be used in conjunction with any medical device adapted to be inserted into a physiological lumen. In certain implementations, the medical device may include a lumen running its length. The device lumen may serve as a tool or catheter port such that tools and/or catheters can be threaded down the length of the medical device and out of a distal end of the device. Alternatively, the device may be threaded onto tools or catheters already disposed within the physiological lumen.

FIG. 10 is a schematic illustration of a first medical device 1000 in the form of a catheter delivery tool. As illustrated, the medical device 1000 includes a proximal hub 1004 from which each of a catheter tool channel 1006 and a balloon insufflation channel 1008. A distal portion 1010 of the catheter tool channel 1006 extends from the hub 1004 and includes a balloon 1002 that may be selectively inflated and deflated by providing air to or allowing air to escape from the balloon 1002 via the balloon insufflation channel 1008, respectively. Accordingly, the distal portion 1010 may be inserted into a physiological lumen of a patient with the balloon deflated. Once located at a point of interest within the physiological lumen, air may be provided to the balloon 1002 via the balloon insufflation channel 1008 to cause the balloon 1002 to expand and engage the wall of the physiological lumen. When so engaged, the catheter tool channel 1006 may be used to provide a clear and direct pathway to the location of interest.

The medical device 1000 is described above as being used in conjunction with or to guide a catheter or guide wire within the physiological lumen; however, in other implementations of the present disclosure, balloons in accordance with the present disclosure may be incorporated into catheters or guide wires. For example and without limitation in at least one implementation of the present disclosure an inflatable balloon as described herein may be disposed along a guide wire or catheter (e.g., at or near distal end of the guide wire or catheter). In such implementations, the guidewire or catheter may be inserted into a physiological lumen with the balloon in the deflated state. The balloon may be subsequently inflated to engage the physiological lumen and at least partially anchor the guide wire or catheter within the physiological lumen.

Figure 11:
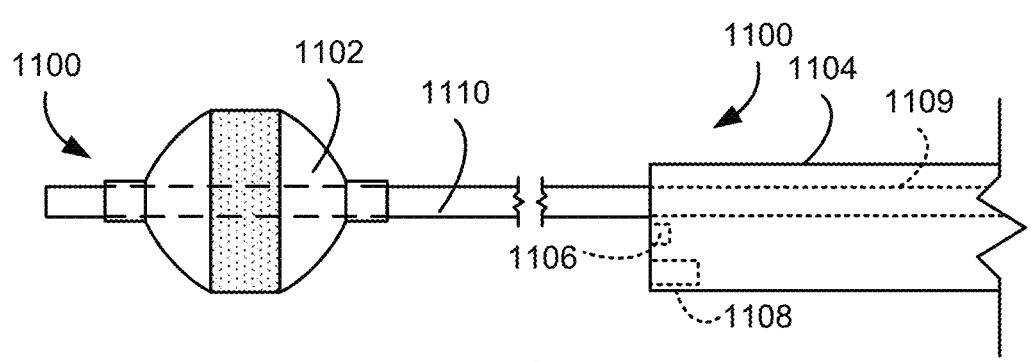
FIG. 11 is a schematic illustration of an example endoscopic medical device in accordance with the present disclosure and including a catheter-mounted balloon.

FIG. 11 is a schematic illustration of a second medical device 1100, which may be an endoscopic tool. The second medical device 1100 includes an endoscope body 1104 that may include, for example and without limitation, a light emitting diode (LED) 1106 and a camera 1108. The endoscope body 1104 may also define a catheter channel 1109 through which a catheter 1110 may be inserted. As illustrated in FIG. 11, the catheter 1110 may include a distal balloon 1102 that may be used to at least partially secure the catheter 1110 within a physiological lumen.

In one example application of the medical device 1100, the catheter 1110 may be used as a guide for the endoscope body 1104. More specifically, during a first process the catheter 1110 may be delivered to a point of interest along a physiological lumen with the balloon 1102 in an uninflated state. Once located, the balloon 1102 may be inflated to engage the balloon 1102 with the lumen and at least partially secure the catheter within the lumen. The endoscope body 1104 may then be placed onto the catheter 1110 such that the endoscope body 1104 may be moved along the catheter 1110, using the catheter as a guide.

Figure 12:
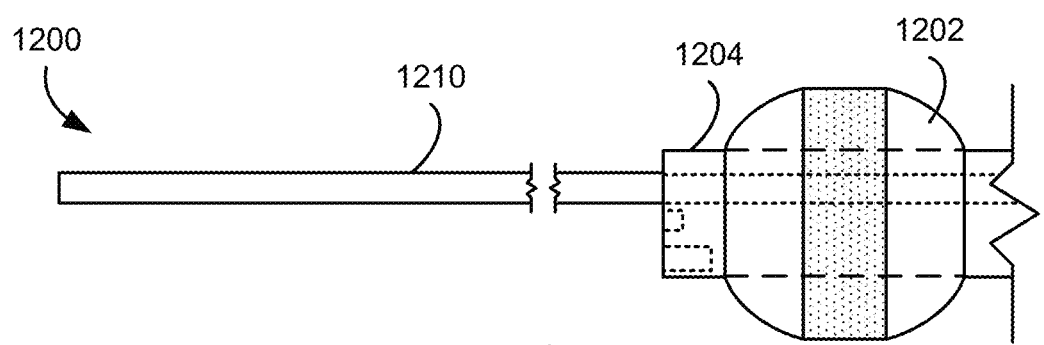
FIG. 12 is a schematic illustration of a second example endoscopic medical device in accordance with the present disclosure and including an endoscope-mounted balloon.

FIG. 12 is a schematic illustration of a third medical device 1200. Similar to the medical device 1100 of FIG. 11, the medical device 1200 includes an endoscope body 1204 (or body of a similar tool) that may be configured to receive a catheter 1210. However, in contrast to the medical device 1100 of FIG. 11 in which the balloon 1102 was coupled to the catheter 1110, the medical device 1200 includes a balloon 1202 coupled to the endoscope body 1204 and which may be used to at least partially secure the endoscope body 1204 within a physiological lumen of a patient.

Figure 13:
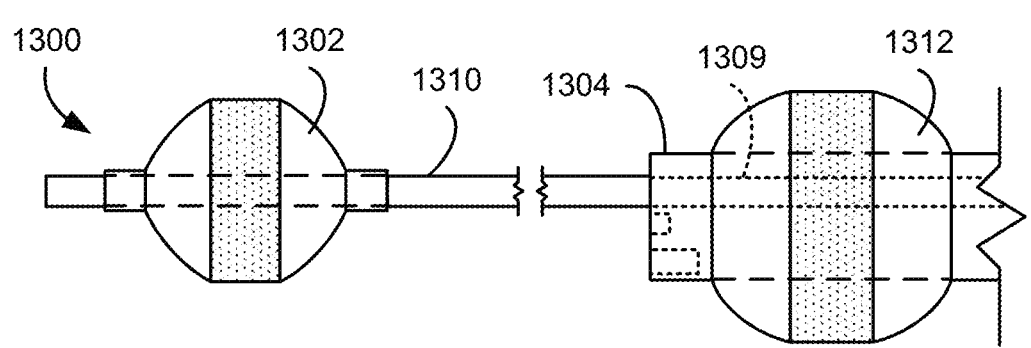
FIG. 13 is a schematic illustration of a third example endoscopic medical device in accordance with the present disclosure and including each of a catheter-mounted balloon and an endoscope-mounted balloon.

FIG. 13 is a schematic illustration of a fourth medical device 1300 that combines aspects of both the medical device 1100 of FIG. 11 and the medical device 1200 of FIG. 12. More specifically, the medical device 1300 includes an endoscope body 1304 that defines a catheter channel 1309 through which a catheter 1310 may be inserted. Like the medical device 1100 of FIG. 11, the catheter 1310 includes a distal balloon 1302 that may be used to at least partially secure the catheter 1310 within a physiological lumen. Also, like the medical device 1200 of FIG. 12, the endoscope body 1304 also includes a balloon 1312.

Figure 17:
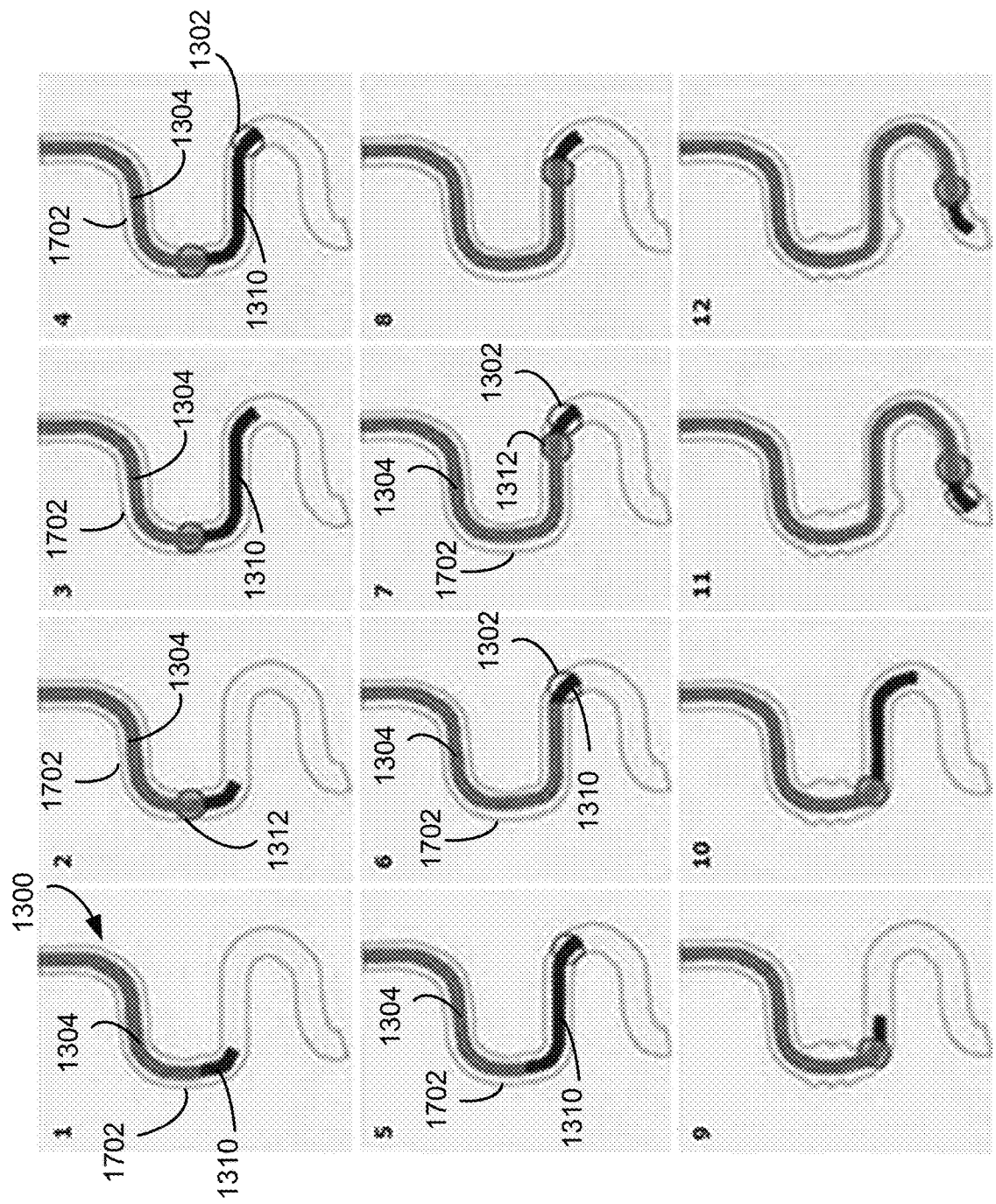
FIG. 17 is a graphical illustration of an example medical procedure performed using the medical device of FIG. 13.

The two-balloon configuration of the medical device 1300 may be used to progress the medical device 1300 along the physiological lumen. For example, FIG. 17 provides a series of illustrations depicting progression of the medical device 1300 along a physiological lumen 1702 (indicated in Frame 1). As illustrated, the medical device 1300 may first be inserted into the physiological lumen in an uninflated/disengaged configuration (Frame 1). The endoscope balloon 1312 may then be inflated to engage the balloon 1312 with the lumen 1702 and to at least partially secure the endoscope body 1304 within the lumen 1702 (Frame 2). With the endoscope body 1304 secured, the catheter 1310 may then be extended from the endoscope body 1304 along the lumen (Frame 3) and the catheter balloon 1302 may be engaged with the lumen 1702 at a second location by inflating the catheter balloon 1302 at the second location (Frame 4). The balloon 1312 may then be deflated (Frame 5) and the endoscope body 1304 may be progressed along the lumen 1702 using the anchored catheter 1310 as a guide (Frame 6). When the endoscope body 1304 reaches the catheter balloon 1302, the endoscope body 1304 may again be secured within the lumen 1702 by inflating the balloon 1312 (Frame 7). As illustrated in Frames 8-12, this process may be repeated to progress the medical device 1300 along the physiological lumen 1702.

In certain implementations, the medical device may be a double balloon endoscope comprising a flexible overtube, as described in PCT Application Publication WO 2017/096350, wherein at least a portion of the outer surface of one or both of the first and second inflatable balloons includes a micro-patterned surface as described herein. In other embodiments, the endoscope does not include an overtube.

Figure 14:
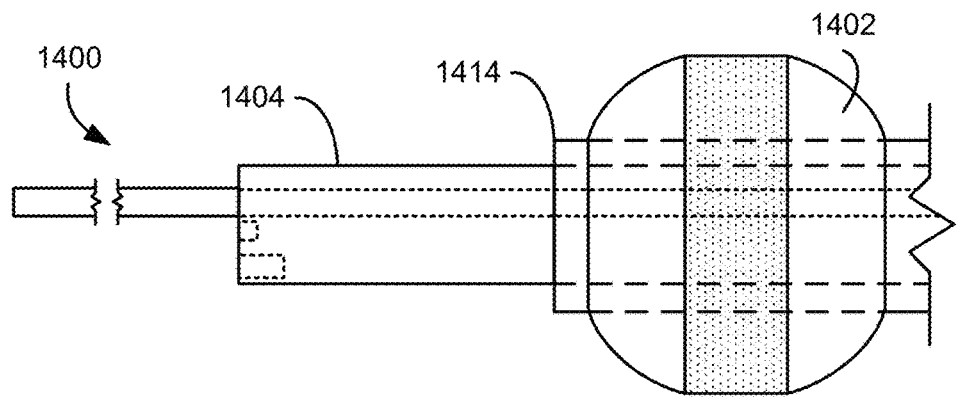
FIG. 14 is a schematic illustration of a fourth example endoscopic medical device in accordance with the present disclosure and including an overtube-mounted balloon.
Figure 15:
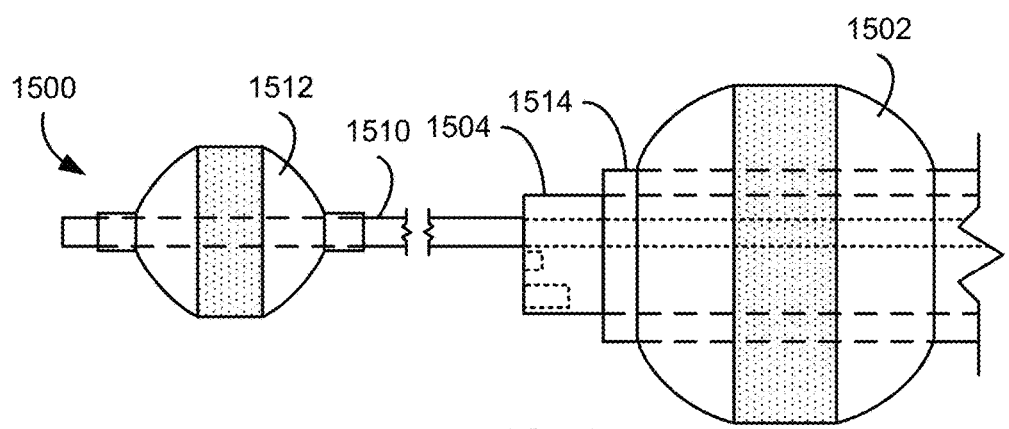
FIG. 15 is a schematic illustration of a fifth example endoscopic medical device in accordance with the present disclosure and including each of a catheter-mounted balloon and an endoscope-mounted balloon.
Figure 16:
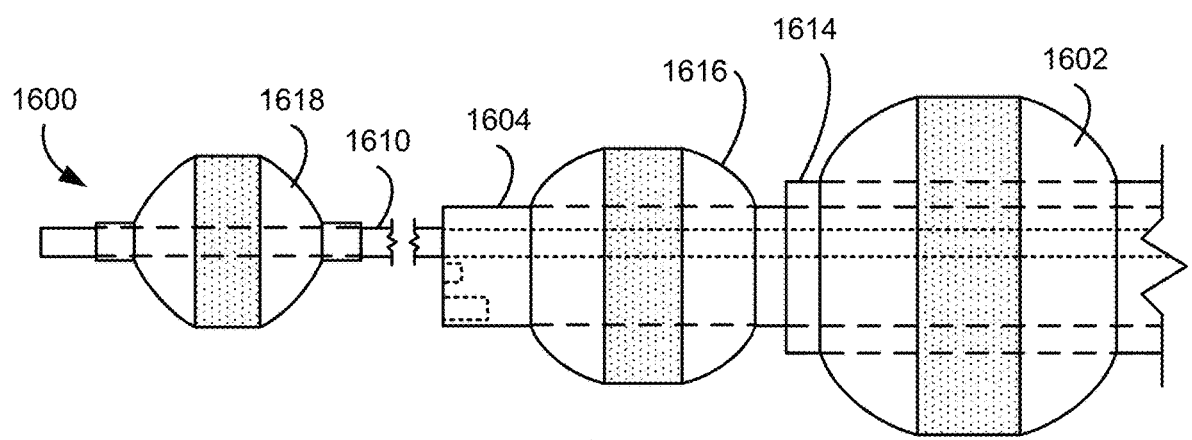
FIG. 16 is a schematic illustration of a sixth example endoscopic medical device in accordance with the present disclosure and including each of a catheter-mounted balloon, an endoscope-mounted balloon, and an overtube-mounted balloon.

FIGS. 14-16 illustrate additional variations of the foregoing example medical devices. FIG. 14 is a schematic illustration of a medical device 1400 in which a balloon 1402 is coupled to an overtube 1414 through which an endoscope device 1404 may be inserted. FIG. 15 is a schematic illustration of a medical device 1500 similar to that of FIG. 14 in that it includes a balloon 1502 coupled to an overtube 1514 through which an endoscope body 1504 extends. In addition to the balloon 1502, the medical device 1500 includes a catheter balloon 1512 coupled to a distal end of a catheter 1510 extending through the endoscope body 1504. An example double balloon endoscope device similar to that of FIG. 15 and including a flexible overtube is described in detail in PCT Application Publication WO 2017/096350, which is incorporated herein by reference in its entirety. Finally, FIG. 16 is another schematic illustration of a medical device 1600 including three distinct balloons. Specifically, the medical device 1600 includes a first balloon 1602 coupled to an overtube 1614, a second balloon 1616 coupled to an endoscope body 1604 extending through the overtube 1614, and a third balloon 1618 coupled to a catheter 1610 extending from the endoscope body 1604.

In each of the medical tools, it is assumed that the described devices include suitable channels for delivering air or other fluid to the disclosed balloons to inflate the balloons and for removing air/fluid from the balloons to deflate the balloons. For example, each device may include a proximal manifold or coupling that may be connected to a pump or other fluid supply and that further includes a vent or return channel through which fluid may be removed from the balloons. In certain implementations, the medical device includes tubing that is in fluidic communication with one or more balloons of the device, the tubing allowing for controlled inflation and/or deflation of one or more of the balloons. In implementations in which the medical device includes multiple balloons, the tubing used to inflate one or more of the multiple balloons. Alternatively, different sets of tubing may be used to independently control inflation and deflation of respective subsets of the balloons of the medical device.

It should also be appreciated that in implementations of the present disclosure having multiple balloons, only one balloon need to have protrusions in accordance with the present disclosure. In other words, medical devices in accordance with the present disclosure my include one textured balloon as described herein, but may also include any number of non-textured balloons or balloons having designs other than those described herein. Moreover, while the example medical devices of FIGS. 10-17 illustrate balloons located near the distal end of components of the medical devices (e.g., catheters, endoscope bodies, overtubes), in other implementations, balloons may be disposed at any location along such components, including at multiple locations along a given component.

Figure 18:
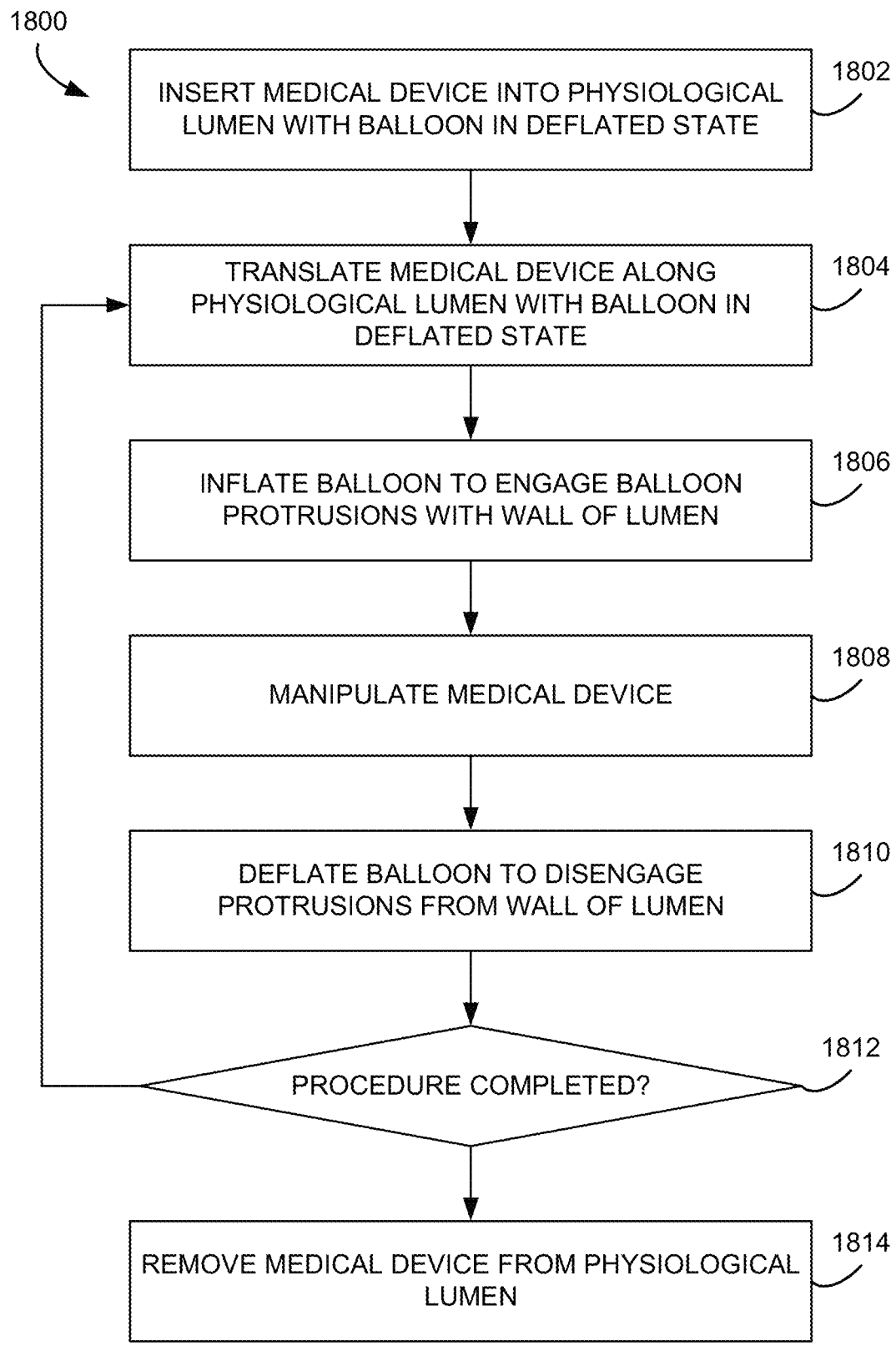
FIG. 18 is a flowchart illustrating an example method of performing a procedure using a medical device according to the present disclosure.

The current disclosure further provides methods of performing endoscopy or similar medical procedures within a body cavity. FIG. 18 is a flowchart illustrating an example method 1800 of such procedures which may be generally performed using medical devices in accordance with the present disclosure, including but not limited to the medical devices discussed in the context of FIGS. 1A-1E and 10-17.

At operation 1802, the medical device is introduced into a physiological lumen or body cavity at least with a balloon of the medical device in a deflated state. As previously discussed, in at least one application of the present disclosure, the physiological lumen may include (but is not limited to) a portion of a patient's GI tract. For example, in the context of a small bowel endoscopy, the physiological lumen may correspond to a portion of a patient's lower digestive system and the medical device may include distal components, such as a light and/or camera, adapted to facilitate examination of the physiological lumen.

Once inserted into the physiological lumen, at least a portion of the medical device is translated along the physiological lumen to an engagement location while the balloon is in the deflated state (operation 1804). For example, in certain implementations, the portion of the medical device may be a catheter including the balloon and translating the portion of the medical device may include extending the catheter and balloon along the physiological lumen while a second portion of the medical device (e.g., an endoscope body) remains at the initial insertion location. In another example implementation, translating the portion of the medical device may include moving an endoscope or similar portion of the medical device along a guide wire or catheter extending along the physiological lumen.

Following translation of the portion of the medical device, the balloon of the medical device is inflated such that protrusions of the balloon as described herein engage with the wall of the physiological lumen (operation 1806).

Once at least partially secured within the lumen, the medical device may be manipulated to perform various functions (operation 1808). In one example, the secured portion of the medical device may include a catheter and the medical device may be manipulated by translating an unsecured portion of the medical device along the physiological lumen using the secured catheter as a guide. In another implementation, the medical device may be manipulated to remove a foreign object or tissue from the physiological lumen. For example, manipulation of the medical device may include insertion and operation of one or more tools of the medical device configured to capture, excise, ablate, biopsy, or otherwise interact with tissue or objects within the physiological lumen. In one specific example, the balloon may be disposed distal a foreign object or tissue of interest within the lumen during operation 1804. The balloon may then be inflated in operation 1806 to obstruct the lumen. In one implementation, the balloon may then be moved proximally through the lumen to remove the foreign object. In another implementation, the balloon may instead be disposed within the lumen and moved distally to remove a foreign object distal the balloon. In another implementation, tools may be inserted through the medical device such that the tools may be used in a portion of the lumen proximal the inflated balloon. The foregoing examples may be useful for removing kidney stones from urinary ducts, removing gall stones from bile ducts, or clearing other foreign or undesirable matter present within the physiological lumen.

In another example medical procedure, a second balloon in accordance with the present disclosure may be disposed and inflated within the physiological lumen such that the protrusions of the second balloon partially engage the wall of the physiological lumen but otherwise remains at least partially movable within the physiological lumen. For example, the second balloon may be disposed on a guide wire or catheter that is then inserted through a medical device previously disposed within the physiological lumen (e.g., during operations 1804 and 1806). With the protrusions of the second balloon partially engaged, the second balloon may be translated along the physiological lumen to rub or scrape the wall of the physiological lumen.

Following manipulation of the medical device, the balloon is deflated to disengage the balloon from the physiological lumen (operation 1810) and an evaluation is conducted to determine when the medical procedure is complete (operation 1812). If so, the medical device is removed from the physiological lumen (operation 1814). Otherwise, the medical device may be repositioned within the physiological lumen for purposes of conducting any additional steps of the procedure (e.g., by repeating operations 1804-1812).

Figure 19:
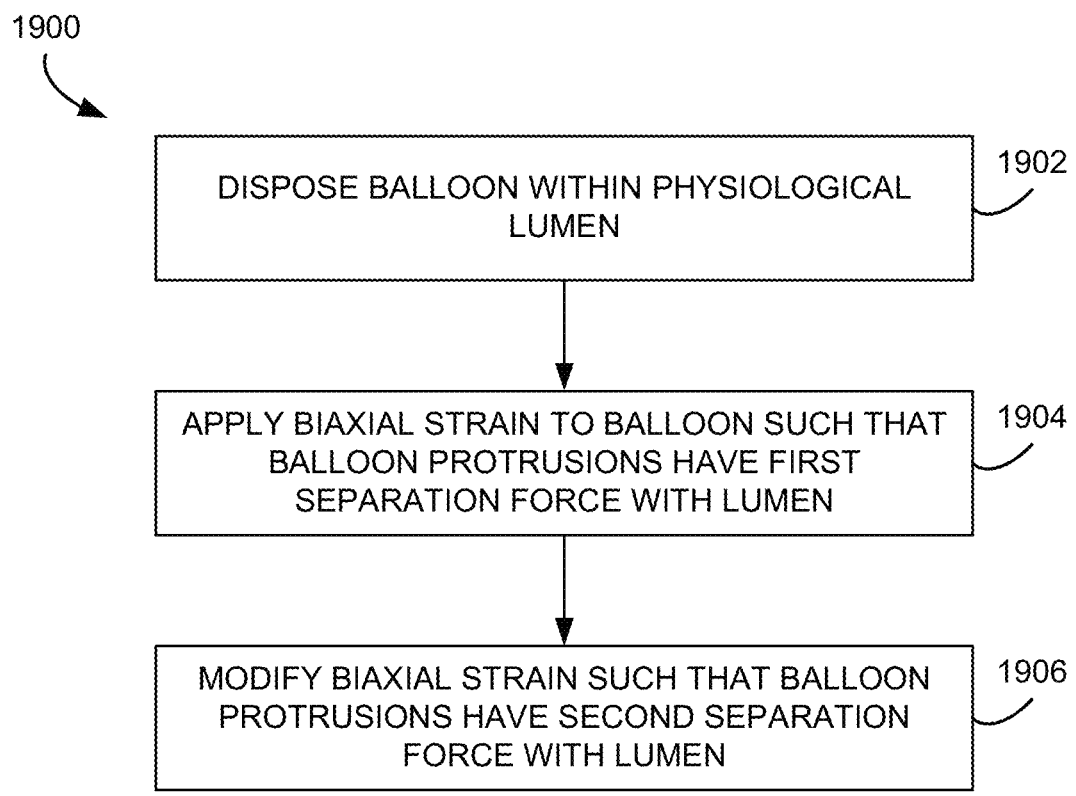
FIG. 19 is a flowchart illustrating a method of modifying engagement between a balloon in accordance with the present disclosure and a physiological lumen.

FIG. 19 is a second flowchart illustrating a method 1900 of modifying engagement between a balloon in accordance with the present disclosure and a physiological lumen. As previously discussed in the context of FIGS. 4A-7, the protrusions of balloons in accordance with the present disclosure may be configured to have adhesive and frictional properties that vary based on the biaxial strain applied to them. More specifically, applying strain to the balloon (e.g., by selectively inflating or deflating the balloon) causes deformation of the protrusions on the balloon's surface which in turn modifies adhesion and friction between the balloon and adjacent tissue. As previously discussed, by modifying the strain applied to the balloon, the adhesive and frictional properties may be dynamically manipulated by a physician to allow for improved control and flexibility during medical procedures.

With the foregoing in mind, the method 1900 begins with disposing a balloon having protrusions in accordance with the present disclosure within a physiological lumen (operation 1902). At operation 1904, a biaxial strain is applied to the balloon, such as by inflating the balloon, such that protrusions of the balloon interact with a wall of the physiological lumen and have a first separation force with the wall. At operation 1906 the biaxial strain is modified such that a second separation force different from the first separation force is achieved between the balloon and the wall of the physiological lumen.

With respect to the foregoing, modifying the biaxial strain in operation 1906 may include either of increasing or decreasing the biaxial strain on the balloon. Increasing the biaxial strain may include, for example, inflating the balloon beyond the extent to which the balloon was inflated during operation 1904. As discussed in the context of FIG. 7, increasing strain on the balloon in such a manner may generally result in an increase in the force required to separate the balloon from the wall of the physiological lumen (i.e., increase friction and/or adhesion). Decreasing the biaxial strain may include, for example, at least partially deflating the balloon to decrease the force required to separate the balloon from the wall of the physiological lumen (i.e., decrease friction and/or adhesion).

Figure 25A:
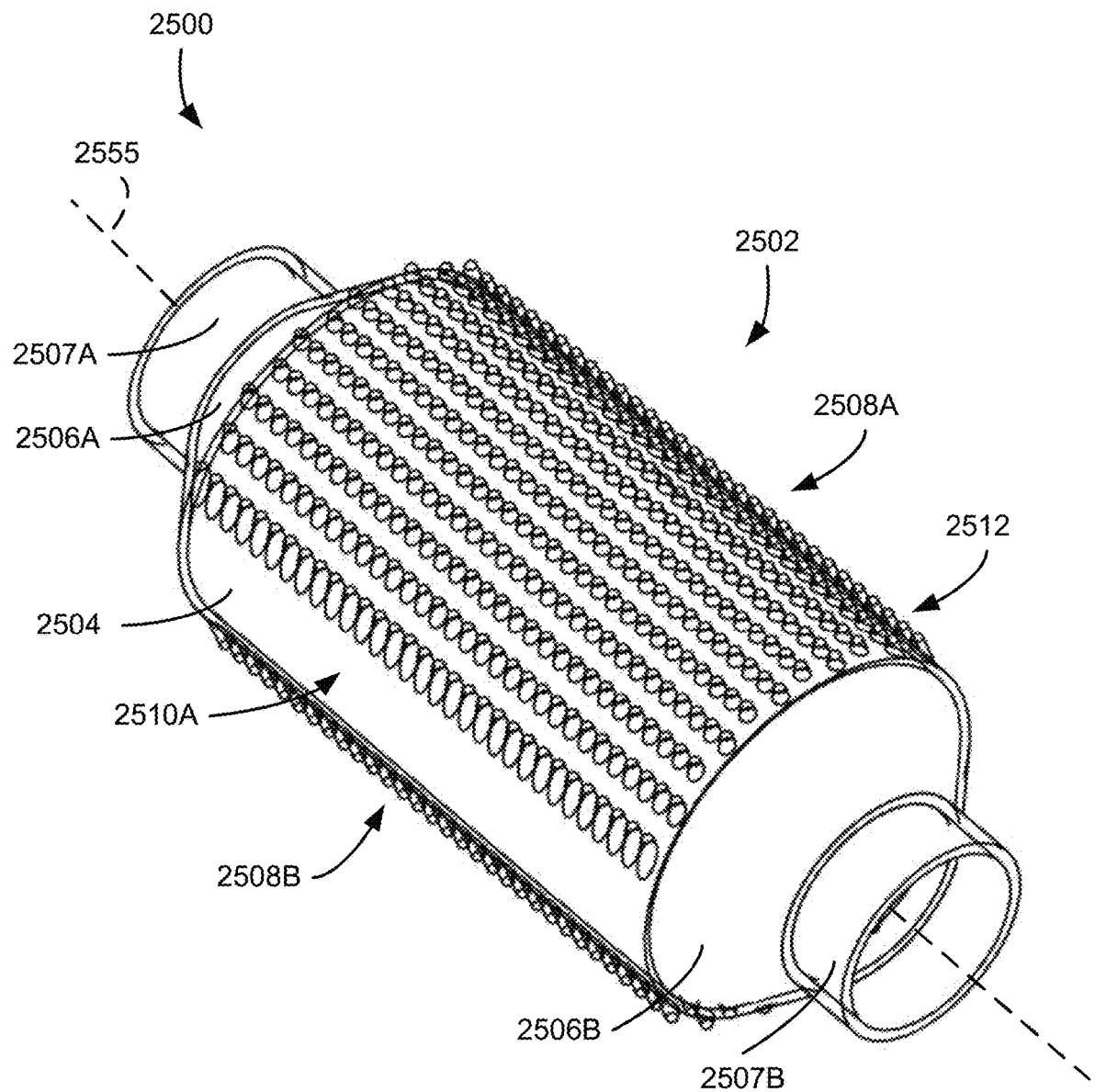
FIGS. 25A-25D are isometric, plan, end, and partial cross-sectional views of an example balloon having textured portions including transverse protrusions.
Figure 25B:
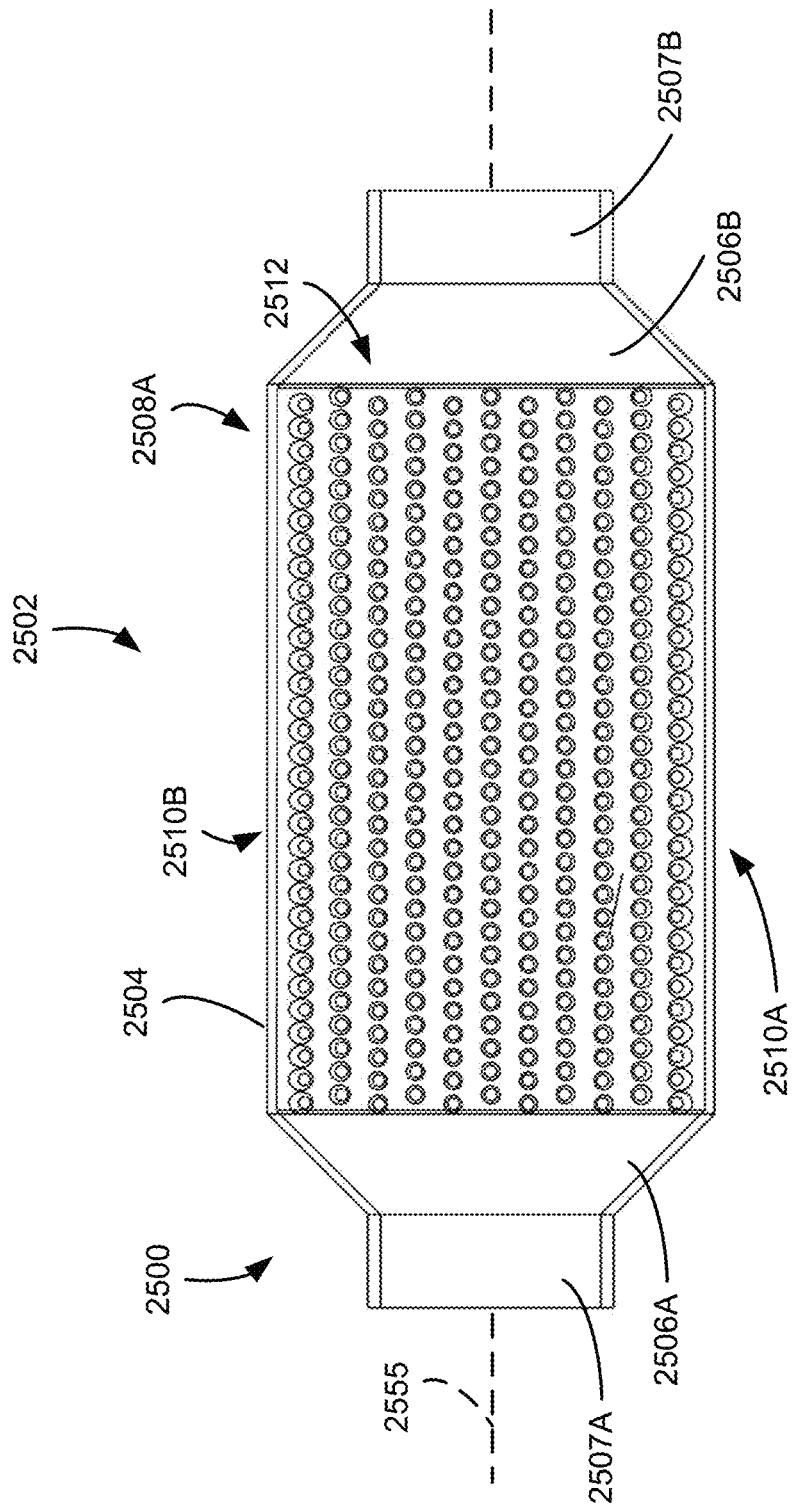
Figure 25C:
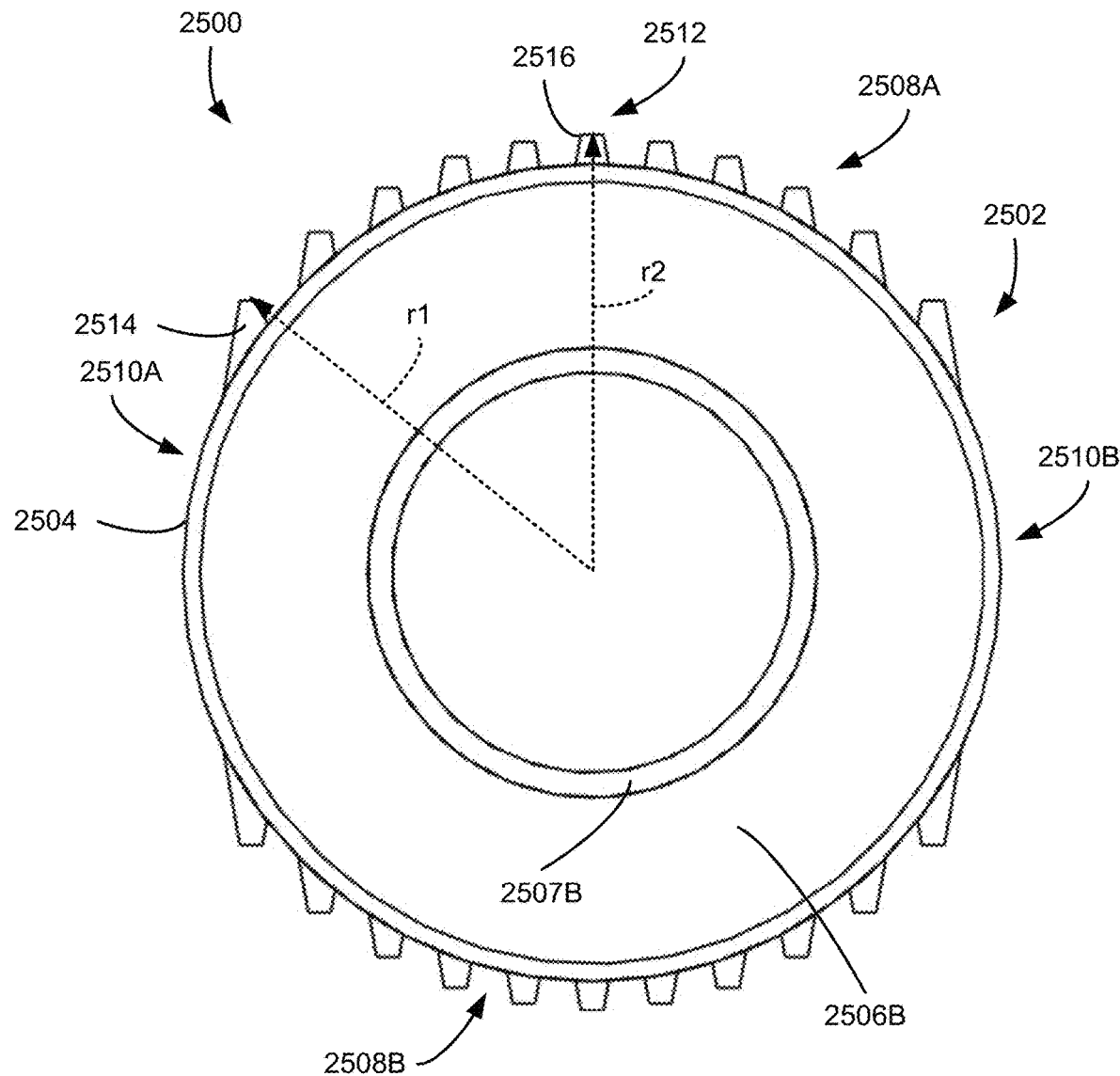
Figure 25D:
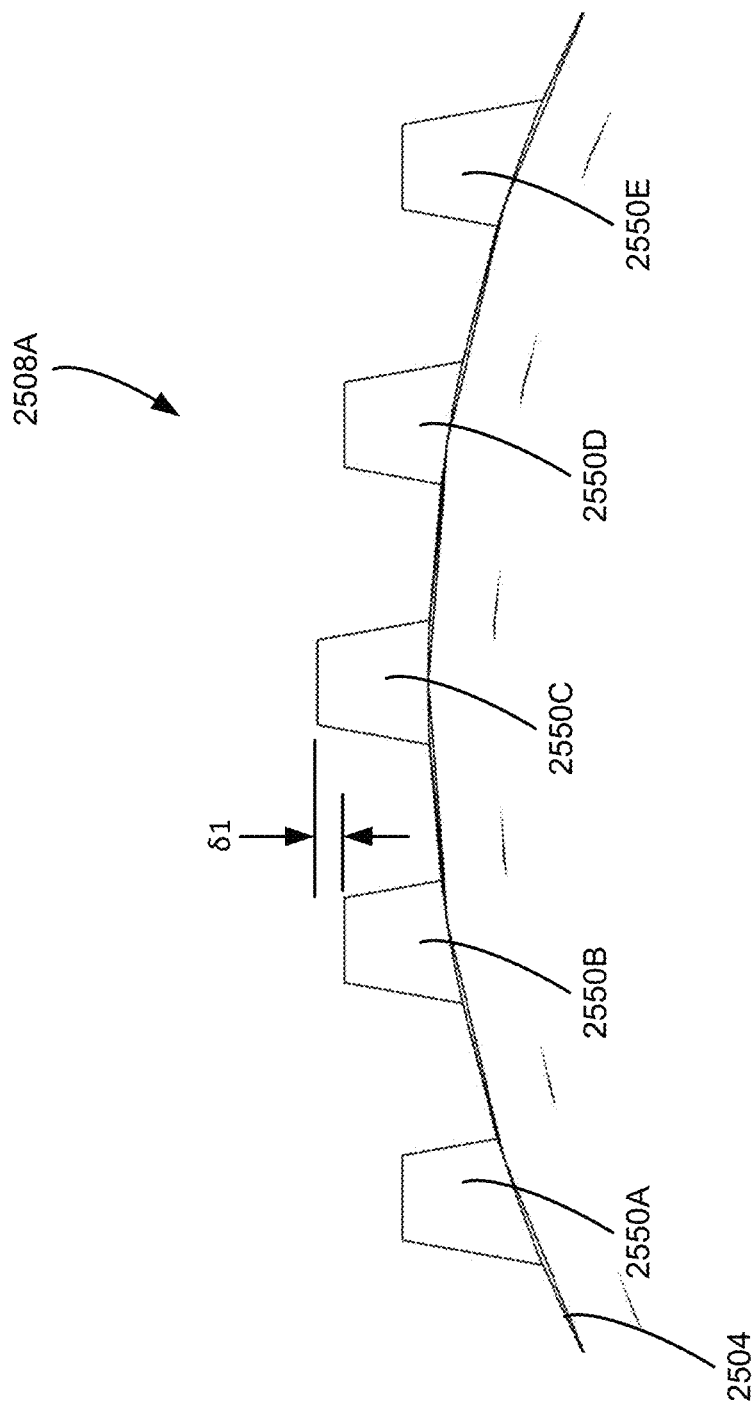

FIGS. 25A-25D illustrate one example implementation of a balloon 2500 in accordance with the present disclosure in an unstrained state. More specifically, FIG. 25A is an isometric view of the balloon 2500, FIG. 25B is a plan view of the balloon 2500, FIG. 25C is an end view of the balloon 2500, and FIG. 25D is a cross-sectional view of a textured surface of the balloon 2500.

Referring first to FIGS. 25A-25C, the balloon 2500 includes an elongate body 2502 extending along a longitudinal axis 2555. The elongate body 2502 generally includes a middle portion 2504 and tapering end portions 2506A, 2506B, each of which terminates in a respective annulus 2507A, 2507B. The middle portion 2504 of the balloon 2500 includes oppositely disposed textured portions 2508A, 2508B. Extending between the textured portions 2508A, 2508B are untextured portions 2510A, 2510B. In other implementations, the surface of the middle portion 2504 of the balloon 2500 may be divided into more than two textured portions and/or more than two untextured portions. Similarly, balloons in accordance with the present disclosure may include only one textured portion.

As best seen in FIG. 25B, the textured portions 2508A, 2508B of the balloon 2500 include uniformly distributed longitudinal rows of protrusions (e.g. protrusions rows 2512). As discussed below in further detail, the protrusions of the balloon 2500 have a truncated cone shape, although other protrusion shapes may be used in other implementations. Also, as visible in FIG. 25B, adjacent rows of protrusions of the balloon 2500 are offset relative to each other such that every other row is aligned. In other implementations other row configurations may be implemented. For example, all rows may be aligned or multiple offsets may be used between different pairs of rows.

In at least certain implementations, the frictional and adhesive properties of the protrusions within a given row may vary based on the longitudinal spacing between the protrusions. For example, if spacing between protrusions is relatively narrow (e.g., from around 25 µm to around 400 µm, or from around 5% to 50% of the width of the protrusions), traction in a collapsed or unstrained state is generally reduced as compared to implementations including wider spacing. Testing suggest that such variable traction is the result of narrowly spaced protrusions in a given row more closely approximating the drag and traction provided by a continuous structure (e.g., a rib) as opposed to a series of independent protrusions. For example, during certain tests, it was observed that when in a partially deflated state, traction for a given balloon having twenty rows of approximately forty protrusions each approximated the traction provided by twenty continuous ribs extending along the length of the balloon. However, as the spacing between the protrusions was increased (e.g., by inflating and expanding the balloon) traction was observed to increase significantly. Among other things, the increase in traction was attributable to substantially all of the leading edges of the 400 protrusions being exposed and able to fully engage and interact with the inner wall of the physiological lumen when in the expanded state as compared to when the protrusions were more closely spaced.

The protrusions are configured such that when in a partially inflated state, each protrusion of each respective textured portion 2508A, 2508B extends in a common transverse direction relative to the longitudinal axis. In other words, the protrusions of the textured portion 2508A extend parallel to each other in a first transverse direction while the protrusions of the textured portion 2508B extend parallel to each other in a second transverse direction that is opposite the first lateral direction. In other implementations, the textured portions 2508A, 2508B may not be oppositely disposed but nevertheless including protrusions that extend in respective transverse directions.

As shown in FIG. 25C, the textured portions 2508A, 2508B and the untextured portions 2510A, 2510B collectively extend around the circumference of the middle portion 2504 of the balloon 2500. In the particular example illustrated in FIG. 25C, each textured portion 2508A, 2508B extends around about a third of the surface of the middle portion 2504, while the remaining third of the surface is divided between the untextured portions 2510A, 2510B. It should be appreciated, however, that the distribution of the textured and untextured portions of the balloon 2500 may vary from that which is illustrated in FIGS. 25A-D.

As previously noted, each of the tapering end portions 2506A, 2506B terminate in a respective annulus 2507A, 2507B. In general, each annulus 2507A, 2507B is sized and shaped to be fit onto an overtube, catheter, endoscope, or similar tool. Accordingly, the shape and dimensions of each annulus 2507A, 2507B may vary depending on the specific tool onto which the balloon 2500 is to be disposed. However, in at least certain implementations, each annulus 2507A, 2507B may be reinforced relative to other portions of the balloon 2500 that are intended to expand. For example, in certain implementation, the wall thickness of each annulus 2507A, 2507B may be from and including about 1.25 times to and including about 5 times thicker than the wall thickness of the rest of the balloon 2500. Among other things, thickening each annulus 2507A, 2507B facilitates improved retention of the balloon 2500 on an overtube or other tool, particularly when the balloon 2500 is subjected to inflation and deflation.

As illustrated in FIG. 25C, in at least certain implementations, the height of each protrusion may be defined such that each protrusion extends to a common radius. For example, protrusion 2514 has a height such that a center of the tip of the protrusion 2514 extends to a radius r1 while protrusion 2516 has a height such that a center of the tip of the protrusion 2516 extends to a radius r2 that is substantially the same as the radius r1 of protrusion 2514. An alternative interpretation of this approach to determining protrusion heights is that each protrusion extends from the surface of the balloon 2500 such that the midpoint of a top surface of each protrusion lies on a common circle.

Referring now to FIG. 25D, a partial cross-sectional view of the middle portion 2504 of the balloon 2500 is provided to illustrate further details of the protrusions of the textured portions 2508A, 2508B. In the particular illustrated design, each protrusion (e.g. protrusions 2550A-2550E) of the balloon 2500 has a truncated conical shape. While illustrated as having flat tops, in at least certain implementations, the top surface of each protrusion may instead be concave, as previously discussed herein.

FIG. 25D illustrates an alternative approach to selecting the height of each protrusion. More specifically, in at least certain implementations, the height of protrusions in each row may be selected such that there is a predetermined height difference between adjacent rows. For example, FIG. 25D includes a dimension δ1 corresponding to the difference in height between adjacent rows. As illustrated, δ1 may be maintained between successive pairs of adjacent rows such that the top surfaces of the protrusions in adjacent rows descend in a step-like manner. Alternatively, δ1 may differ between adjacent rows. Although various values of δ1 may be used in implementations of the present disclosure, in at least certain implementations δ1 may be from and including about 5 µm to and including about 3 mm. The foregoing approach may be used as an alternative to the previously discussed approach in which each protrusion extends such that a midpoint of its tip is at a common radius or lies on a common circle.

Although the specific dimensions of the balloon 2500 may vary based on the particular application of the balloon 2500, in at least certain implementations, the balloon 2500 may have an overall length from and including about 10 mm to and including about 100 mm. In such implementations, the middle portion 2504 of the balloon may be from and including about 5 mm to and including about 90 mm and the end portions 2506A, 2506B may each be from and including about 2 mm to and including about 10 mm. The middle portion 2504 may also have a resting/partially inflated diameter from and including about 2 mm to and including about 50 mm, with the diameter corresponding to the surface of the middle portion 2504 from which the protrusions extend. The middle portion 2504 may also have a wall thickness from and including about 100 µm to and including about 3000 µm. Further in such implementations, each annulus 2507A, 2507B may have an outer diameter from and including 1 mm to and including 20 mm and a wall thickness from and including 100 µm to and including 5000 µm. The foregoing dimensions should be understood to be merely examples and designs in which the foregoing dimensions fall below or exceed the specified ranges should still be regarded as being within the scope of this disclosure.

Referring next to FIGS. 26A-26D, a second balloon 2600 in an unstrained state is provided. Similar to the previously disclosed balloon 2500, the balloon 2600 includes an elongate body 2602 extending along a longitudinal axis 2655, the elongate body including a middle portion 2604 and tapering end portions 2606A, 2606B. Each of the end portions 2606A, 2606B similarly terminates in a respective annulus 2607A, 2607B for coupling the balloon 2600 to an overtube or similar tool. The middle portion 2604 of the balloon 2600 also includes oppositely disposed textured portions 2608A, 2608B and untextured portions 2610A, 2610B extending therebetween.

Figure 26A:
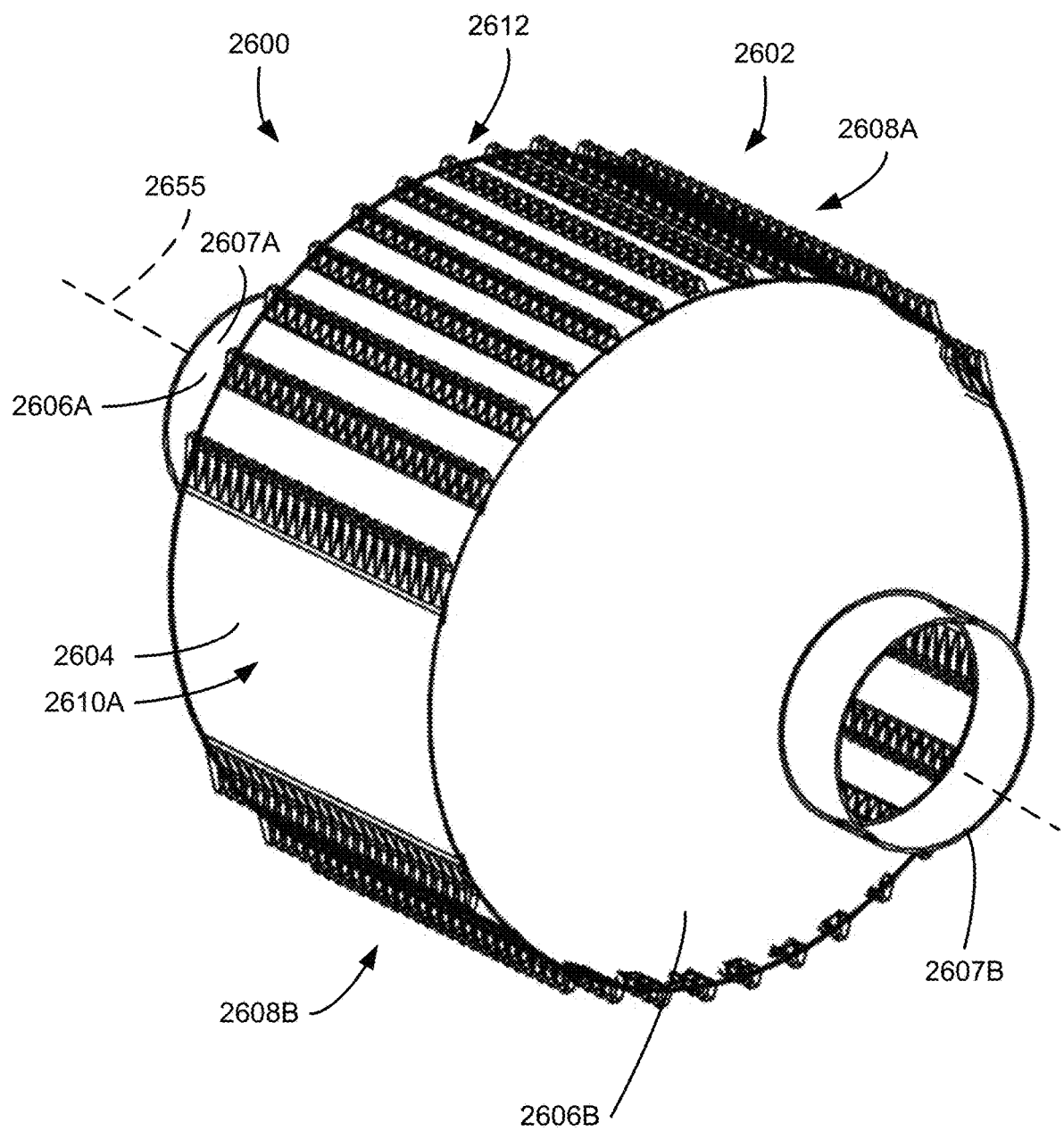
FIGS. 26A-26D are isometric, plan, end, and partial cross-sectional views of another example balloon having textured portions including transverse protrusions.
Figure 26B:
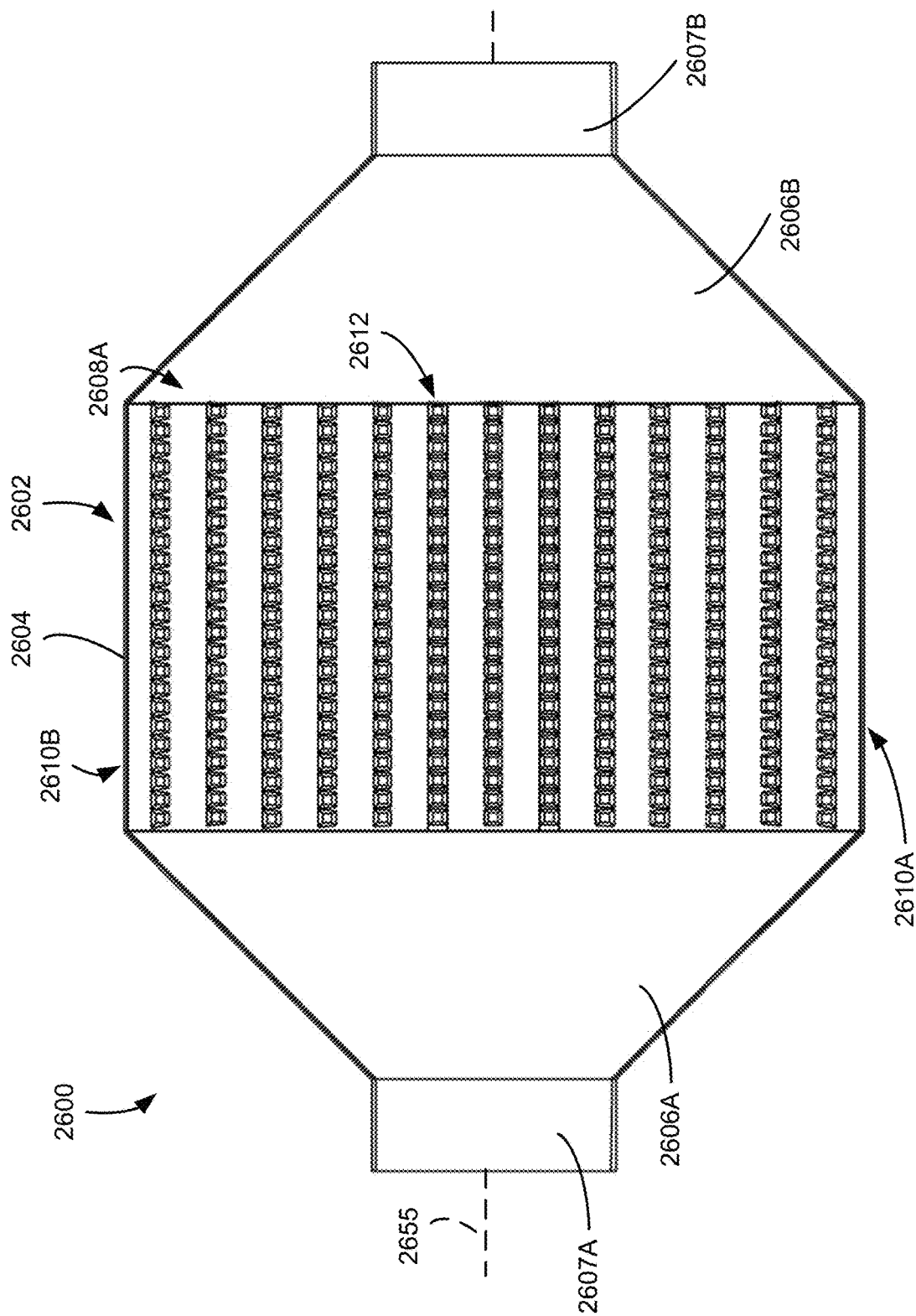
Figure 26C:
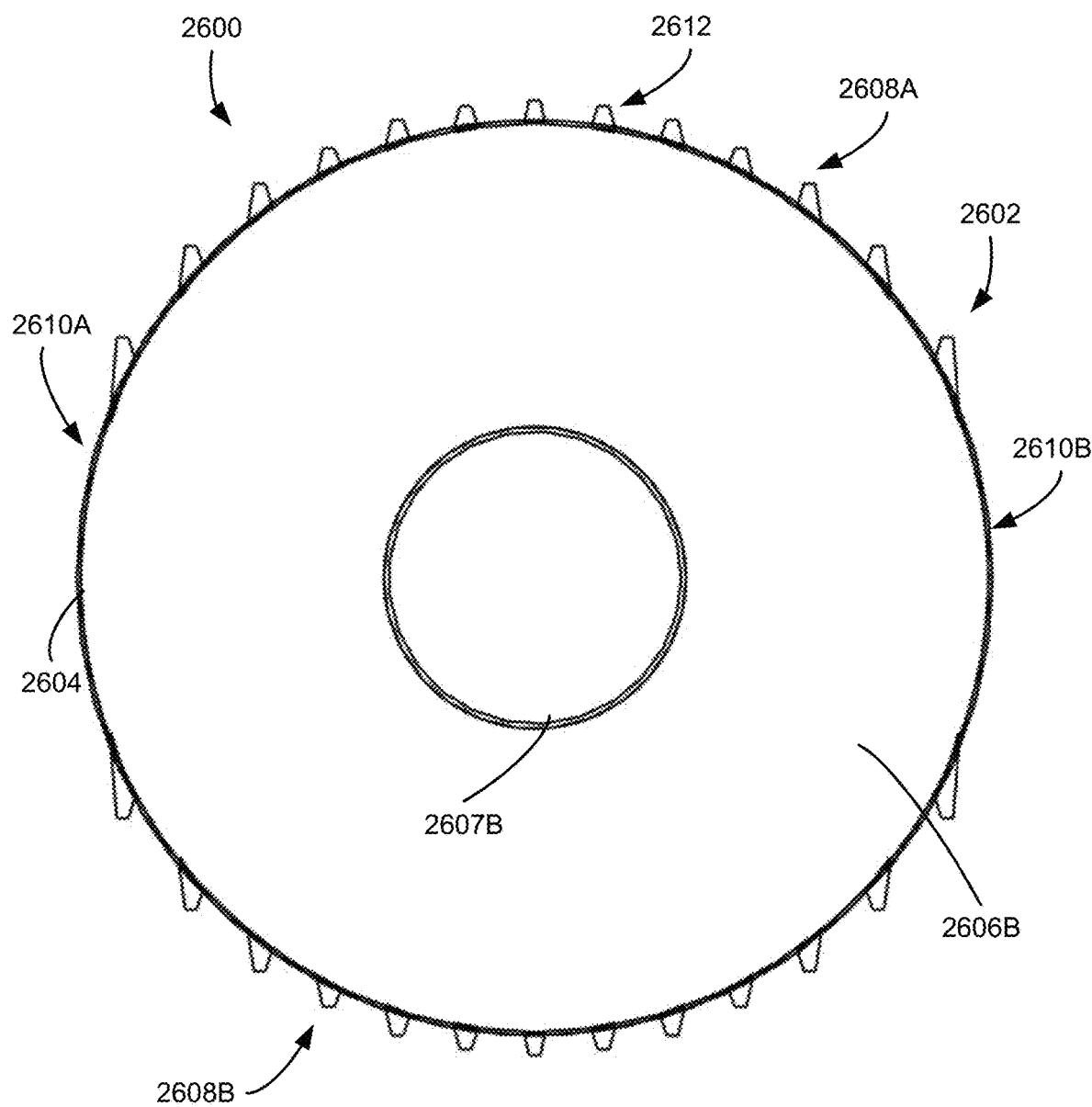

As best seen in FIG. 26B, the textured portions 2608A, 2608B of the balloon 2600 include uniformly distributed rows of protrusions 2612. In contrast to the truncated cone protrusions of the balloon 2500 discussed above, the protrusions of the balloon 2600 have a truncated pyramidal shape. Also, as shown in FIG. 26B, adjacent rows of protrusions of the balloon 2600 are aligned relative to each other, as compared to the offset configuration of the balloon 2500 and adjacent protrusions within a given row of the balloon 2600 are sized and shaped such that they contact each other. This in contrast to the rows of the balloon 2500 in which adjacent protrusions in a row were spaced apart.

Like those of the balloon 2500, the protrusions 2612 of the balloon 2600 are configured such that when in a partially inflated state, each protrusion of each respective textured portion 2608A, 2508B extends in a lateral direction relative to the longitudinal axis. In other words, the protrusions of the textured portion 2608A extend in a first lateral direction while the protrusions of the textured portion 2608B extend in a second lateral direction that is opposite the first lateral direction.

Figure 26D:
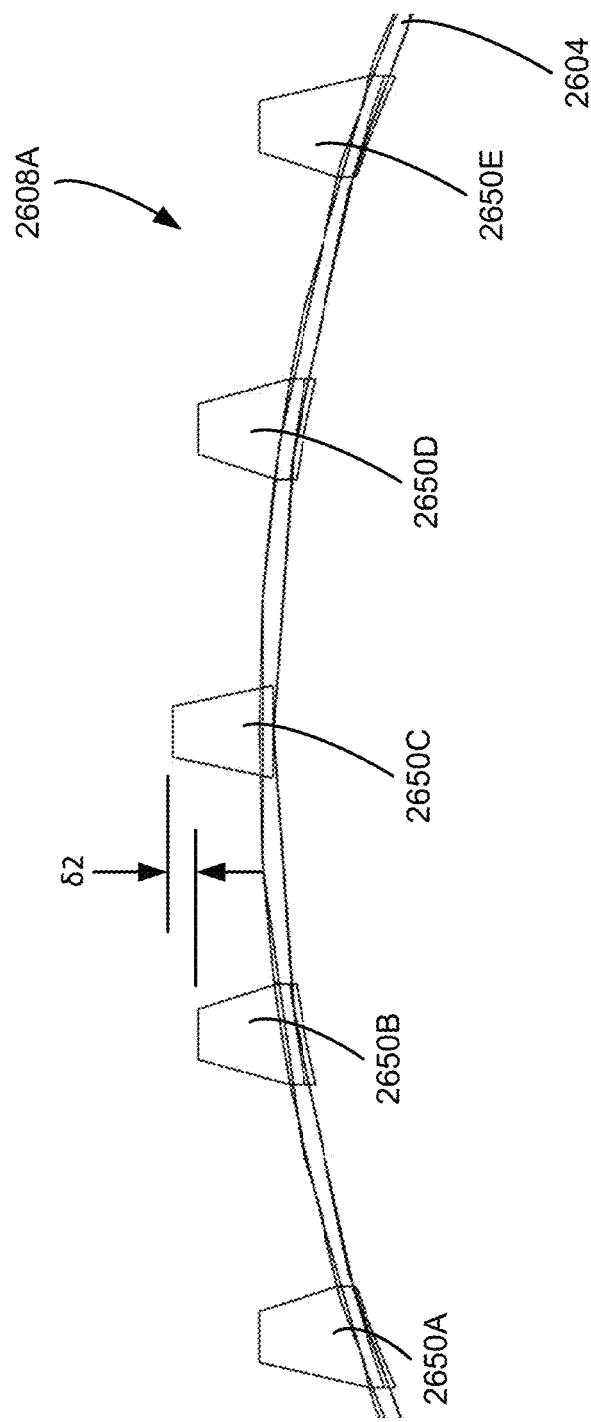

Referring now to FIG. 26D, a partial cross-sectional view of the middle portion 2604 of the balloon 2600 is provided to illustrate further details of the protrusions of the textured portions 2608A, 2608B (e.g., protrusions 2650A-2650E). As previously noted the protrusions 2650A-2650E have a truncated square-based pyramid shape having a flat top. Nevertheless, the top surface of each protrusion may instead be concave, as previously discussed herein. Like the protrusions of the balloon 2500, adjacent rows of the protrusions of the balloon 2600 may be configured such that the change in height (indicated as δ2) between adjacent rows of protrusions may be from and including about 5 µm to and including about 3 mm. Alternatively, and as described above in the context of FIG. 25C, each protrusion may have a height such that a midpoint of a tip of each protrusion extends to a common radius/lies on a common circle.

Although the specific dimensions of the balloon 2600 may vary based on the particular application of the balloon 2600, in at least certain implementations, the balloon 2600 may have an overall length from and including about 10 mm to and including about 100 mm. In such implementations, the middle portion 2604 of the balloon may be from and including about 5 mm to and including about 90 mm and the end portions 2606A, 2606B may each be from and including about 2 mm to and including about 10 mm. The middle portion 2604 may also have a resting/partially inflated diameter from and including about 2 mm to and including about 50 mm, with the diameter corresponding to the surface of the middle portion 2604 from which the protrusions extend. The middle portion 2604 may also have a wall thickness from and including about 100 µm to and including about 3000 µm. Further in such implementations, each annulus 2607A, 2607B may have an outer diameter from and including 1 mm to and including 20 mm and a wall thickness from and including 100 µm to and including 5000 µm. The foregoing dimensions should be understood to be merely examples and designs in which the foregoing dimensions fall below or exceed the specified ranges should still be regarded as being within the scope of this disclosure.

Referring next to FIGS. 27A-27D, a third balloon 2700 in an unstrained state is provided. Similar to the previously disclosed balloons, the balloon 2700 includes an elongate body 2702 extending along a longitudinal axis 2755, the elongate body including a middle portion 2704 and tapering end portions 2706A, 2706B. Each of the end portions 2706A, 2706B terminates in a respective annulus 2707A, 2707B for coupling the balloon 2700 to an overtube or similar tool. The middle portion 2704 of the balloon 2700 includes oppositely disposed textured portions 2708A, 2708B and untextured portions 2710A, 2710B extending therebetween.

The textured portions 2708A, 2708B of the balloon 2700 include uniformly distributed rows of protrusions 2712 and, more specifically, pyramidal protrusions. Similar to the rows of protrusions of the balloon 2600, the rows of protrusions 2712 of the balloon 2700 are aligned relative to each other and adjacent protrusions within a given row of the balloon 2700 are sized and shaped such that they contact each other. However, in contrast to the previous two example balloons 2500, 2600, the protrusions 2712 of the balloon 2700 are configured such that when in a partially inflated state, each protrusion of each respective textured portion 2708A, 2708B extends radially.

Figure 27A:
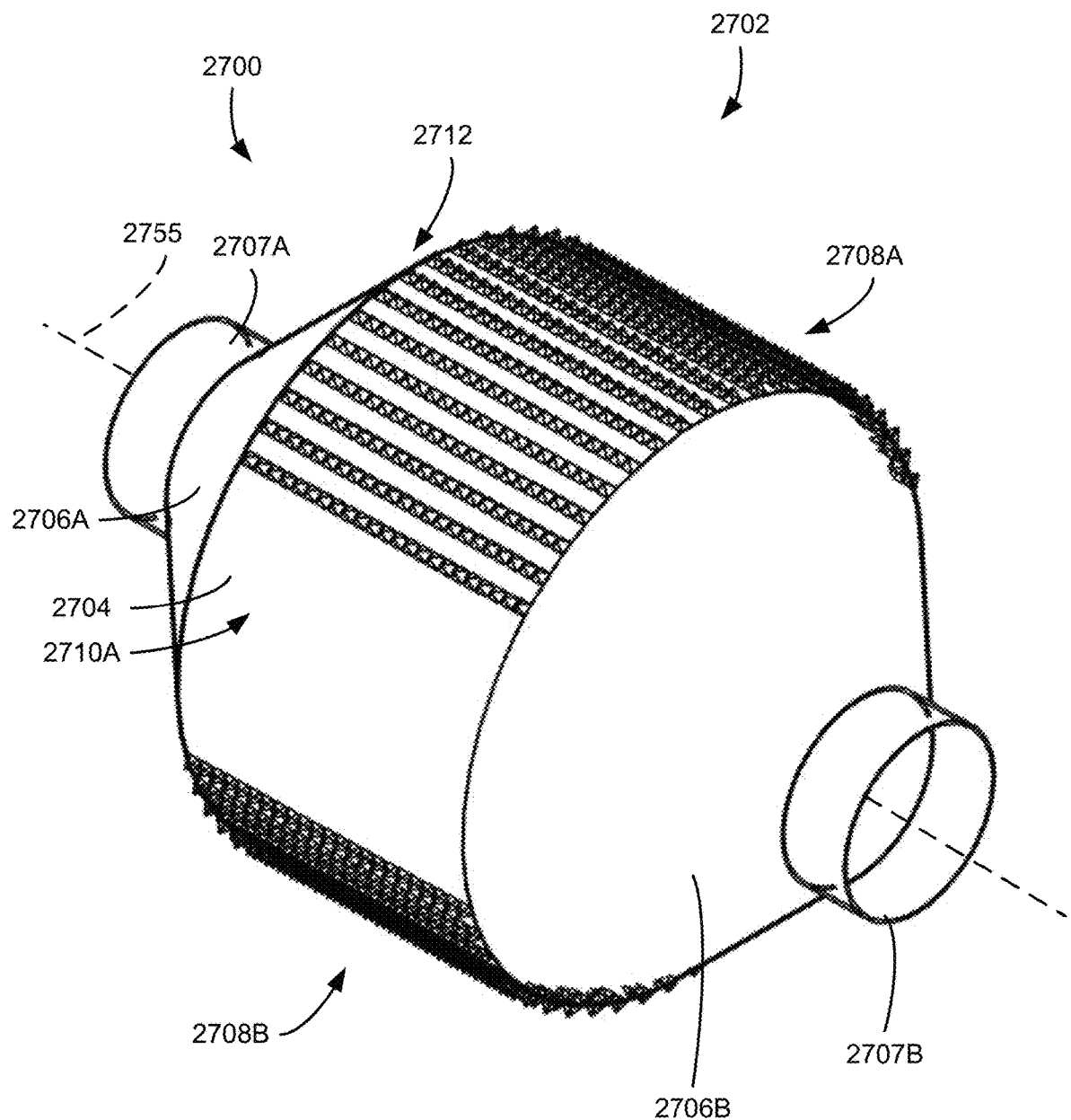
FIGS. 27A-27D are isometric, plan, end, and partial cross-sectional views of an example balloon having texturing portions including radial protrusions.
Figure 27B:
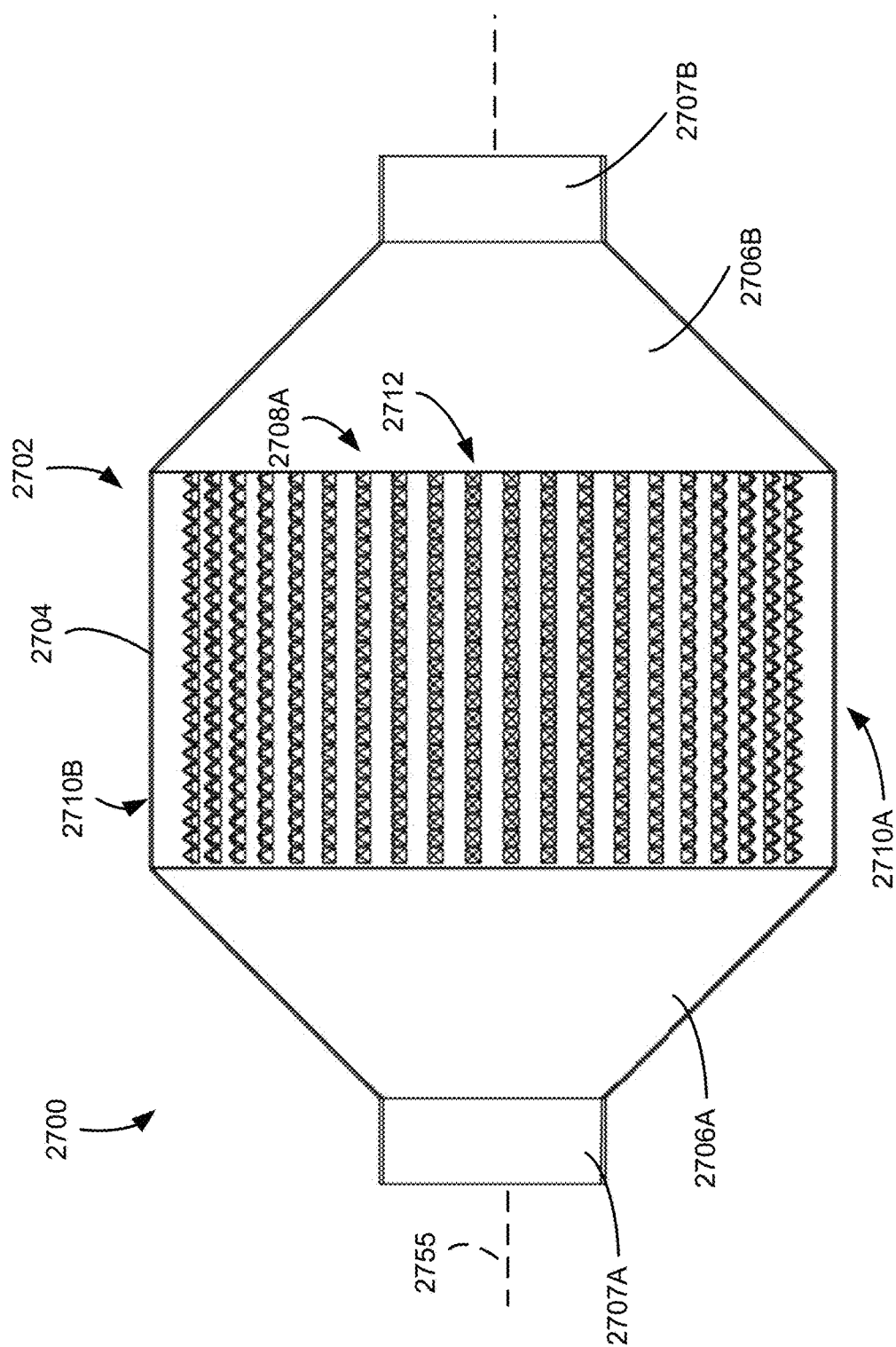
Figure 27C:
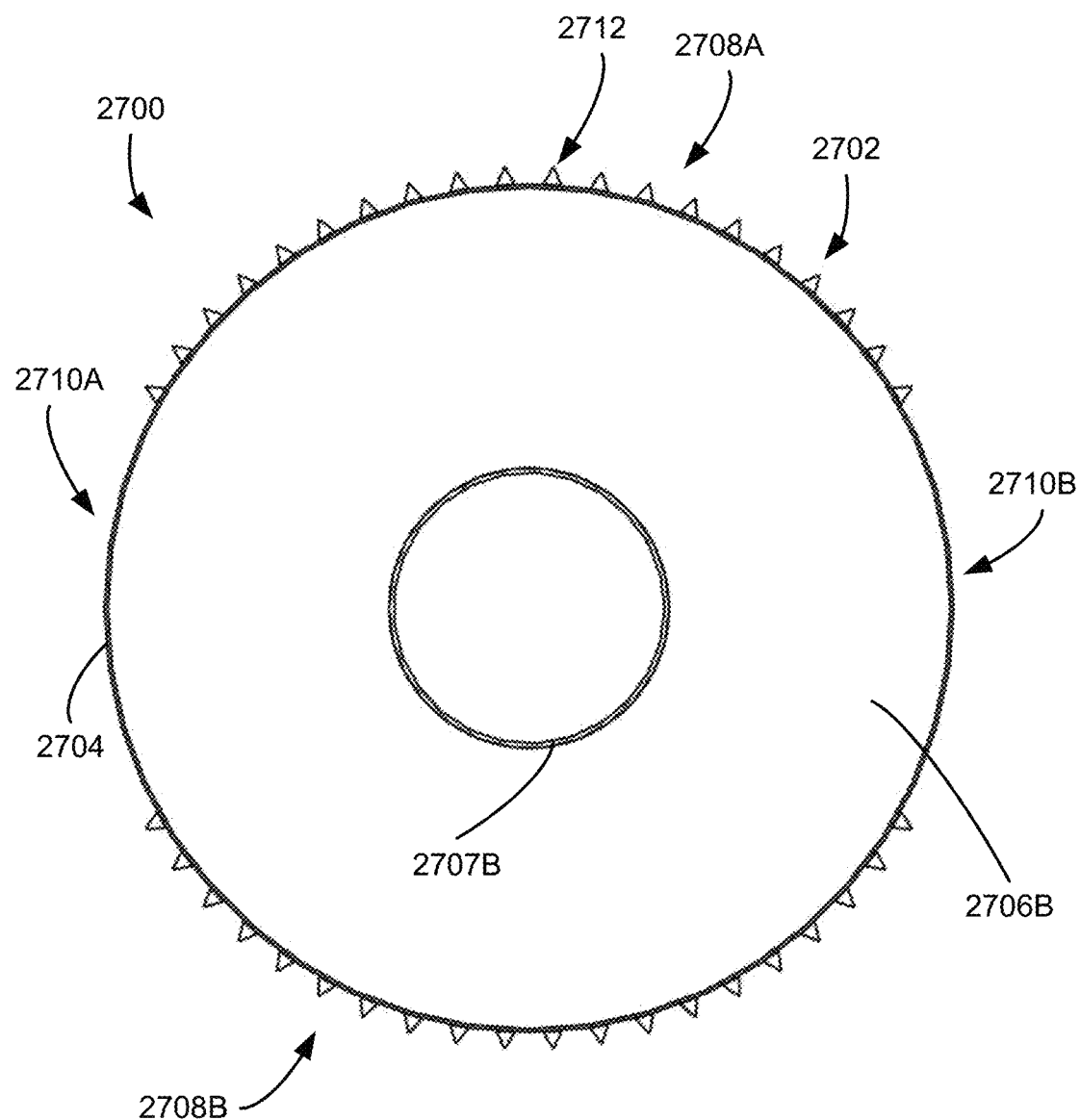
Figure 27D:
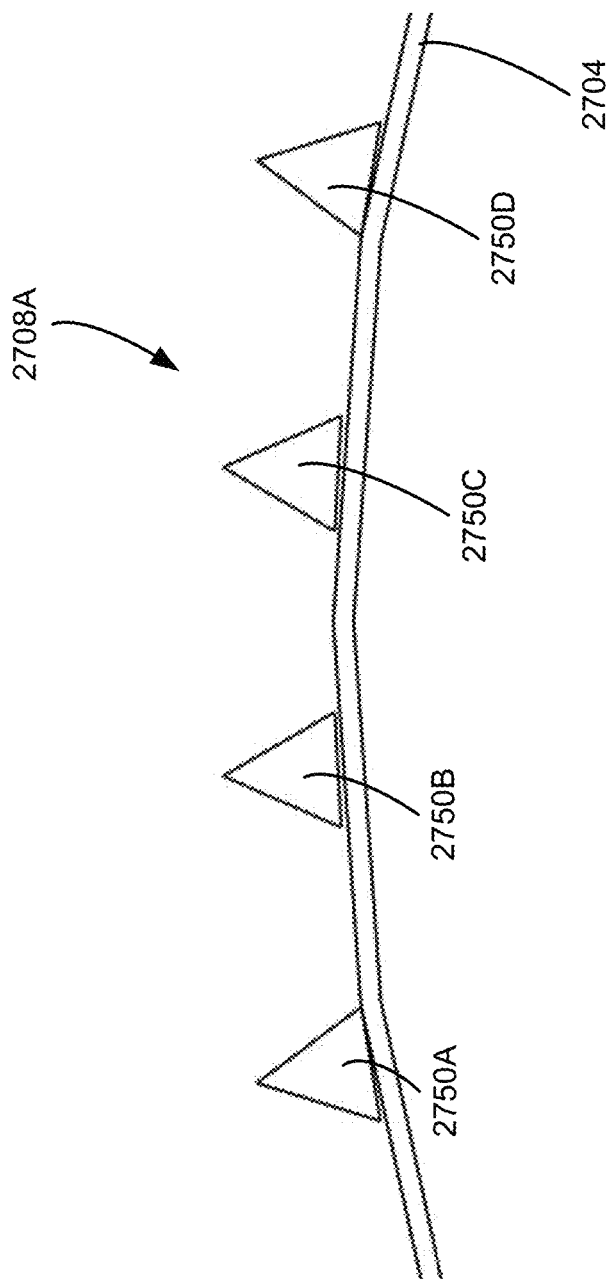

Referring now to FIG. 27D, a partial cross-sectional view of the middle portion 2704 of the balloon 2700 is provided to illustrate further details of the protrusions of the textured portions 2708A, 2708B. As previously noted the protrusions (e.g., protrusions 2750A-2750D) have a pyramidal shape; however, the pyramidal shaped protrusions may have any other suitable shape discussed herein, including shapes having concave top surfaces.

Although the specific dimensions of the balloon 2700 may vary based on the particular application of the balloon 2700, in at least certain implementations, the balloon 2700 may have an overall length from and including about 10 mm to and including about 100 mm. In such implementations, the middle portion 2704 of the balloon may be from and including about 5 mm to and including about 90 mm and the end portions 2706A, 2706B may each be from and including about 2 mm to and including about 10 mm. The middle portion 2704 may also have a resting/partially inflated diameter from and including about 2 mm to and including about 50 mm, with the diameter corresponding to the surface of the middle portion 2704 from which the protrusions extend. The middle portion 2704 may also have a wall thickness from and including about 100 µm to and including about 3000 µm. Further in such implementations, each annulus 2707A, 2707B may have an outer diameter from and including 1 mm to and including 20 mm and a wall thickness from and including 100 µm to and including 5000 µm. The foregoing dimensions should be understood to be merely examples and designs in which the foregoing dimensions fall below or exceed the specified ranges should still be regarded as being within the scope of this disclosure.

Figure 28A:
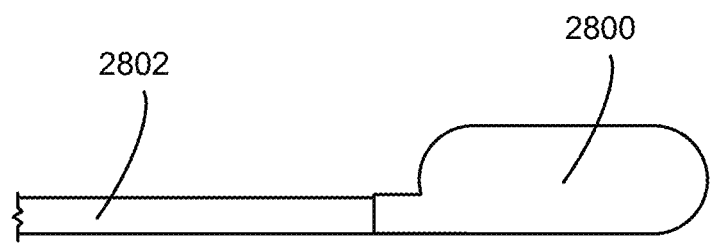
FIGS. 28A and 28B are schematic illustrations of a first directional balloon in a collapsed state and an at least partially inflated state, respectively.
Figure 28B:
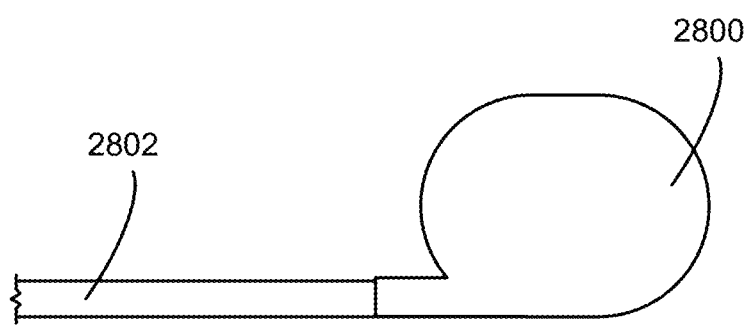

Previous implementations discussed herein generally include balloons that are mounted coaxially with an overtube or similar medical tool and expand in a substantially uniform, radial direction about the tube. Nevertheless, it should be appreciated that in at least certain implementations, such balloons may instead be configured to expand directionally. For example, 28A and 28B illustrates a first example balloon 2800 eccentrically mounted to an overtube 2802. Accordingly, as the balloon 2800 is inflated and expands (as illustrated in the transition from FIG. 28A to 28B), the balloon 2800 is biased to one side of the overtube 2802.

Figure 29A:
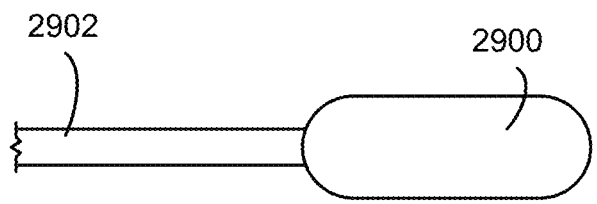
FIGS. 29A and 29B are schematic illustrations of a second directional balloon in a collapsed state and an at least partially inflated state, respectively.
Figure 29B:
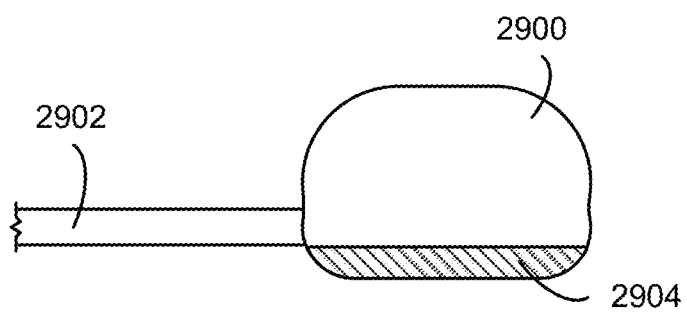

FIGS. 29A and 29B illustrate an alternative implementation in which a balloon 2900 is configured to expand directionally from an overtube 2902 or similar tool on which the balloon 2900 is mounted. Such directional expansion may be achieved, for example, by forming the balloon to have a localized region or side (indicated by hashed area 2904) having increased stiffness or rigidity as compared to other portions of the balloon 2900. Such reinforcement may be achieved, for example, by increasing the wall thickness of the balloon 2900 in the region having reduced expansion; using a stiffer material in the region having reduced expansion; including internal or external ribs, bands, or similar reinforcing structures in the area having reduced expansion; or using any other suitable technique for locally increasing stiffness.

Figure 30A:
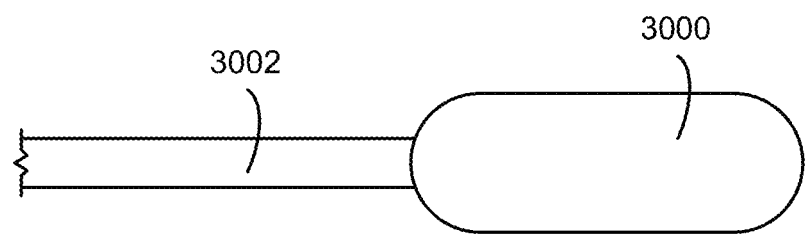
FIGS. 30A and 30B are schematic illustrations of a balloon having non-uniform inflation in a collapsed state and an at least partially inflated state, respectively.
Figure 30B:
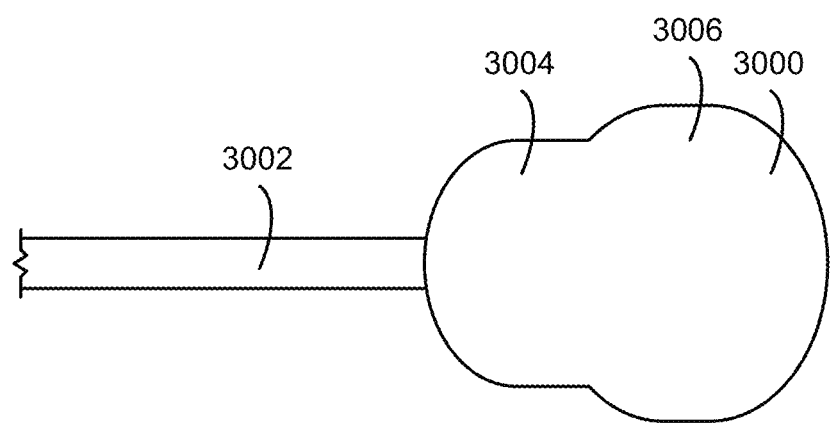

In addition to directional expansion, balloons in accordance with the present disclosure may have variable expansion along their length. For example FIGS. 30A and 30B are schematic illustrations of a balloon 3000 disposed on an overtube 3002 or similar tool. As illustrated in the transition between FIGS. 30A and 30B, when inflated, a proximal portion of the balloon 3004 expands to a lesser extent than a distal portion of the balloon 3006. Similar to the balloon 2900 of FIGS. 29A and 29B, such variable expansion may be achieved by varying material, wall thickness, and reinforcement along the length of the balloon 3000.

Figure 31:
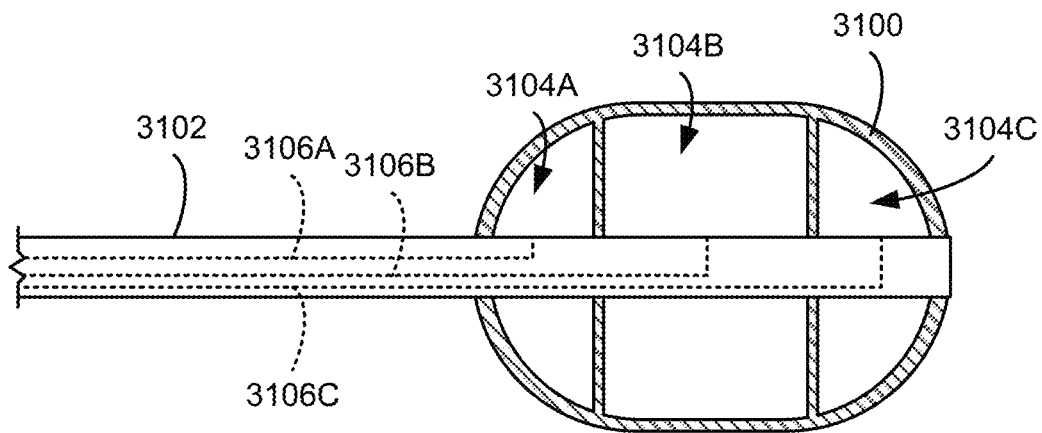
FIG. 31 is a cross-sectional view of a balloon including multiple and independently inflatable internal chambers.

In addition to or as an alternative to selectively reinforcing sections of a balloon to provide variable expansion, balloons in accordance with the present disclosure may include distinct and selectively expandable compartments. For example, FIG. 31 illustrates an example balloon 3100 disposed on an overtube 3102 or similar tool and defining three distinct and isolated internal compartments 3104A-3104C. Each compartment 3104A-3104C is connected to an independently controlled air line 3106A-3106C such that air may be selectively supplied and removed from each of the compartments 3104A-3104C to selectively control their respective expansion and deflation.

Figure 32:
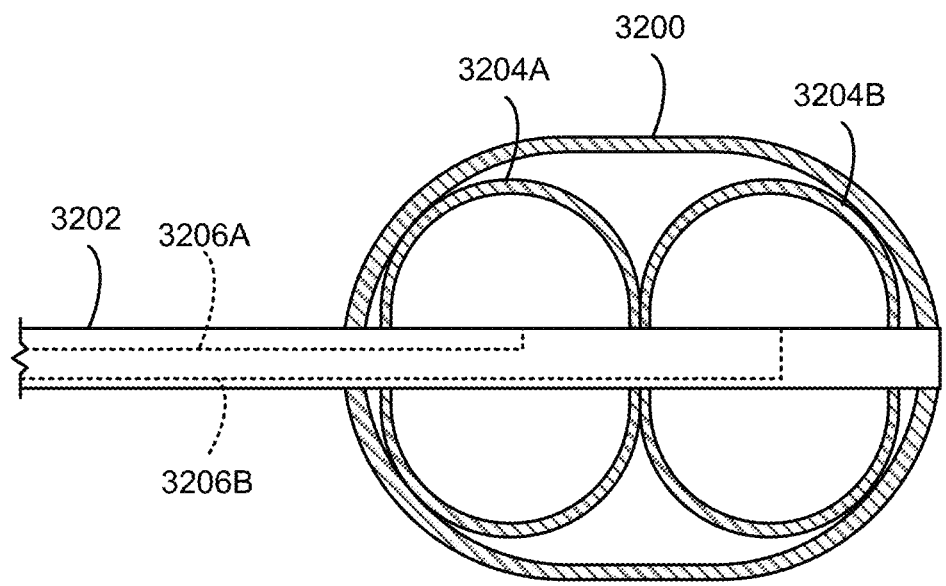
FIG. 32 is a cross-sectional view of a balloon including an outer sheath/balloon and independently inflatable internal balloons disposed within the outer sheath/balloon.

FIG. 32 illustrates an alternative approach to providing a balloon having variably expandable regions. More specifically, FIG. 32 illustrates a sheath or outer balloon 3200 within which multiple and independently inflatable internal balloons 3204A, 3204B may be disposed. Each of the balloons 3200, 3204A, and 3204B may in turn be coupled to an overtube 3202 or similar tool. In such implementations, the outer balloon 3200 may include texturing or protrusions, as described herein, while the internal balloons may be substantially smooth. Similar to the compartmentalized balloon 3100 of FIG. 31, each internal balloon 3204A, 3204B may be in communication with a respective and independently controlled air line 3106A, 3106B to selectively control inflation and deflation of the internal balloons and, as a result, the overall shape of the outer balloon 3200.

Figure 33:
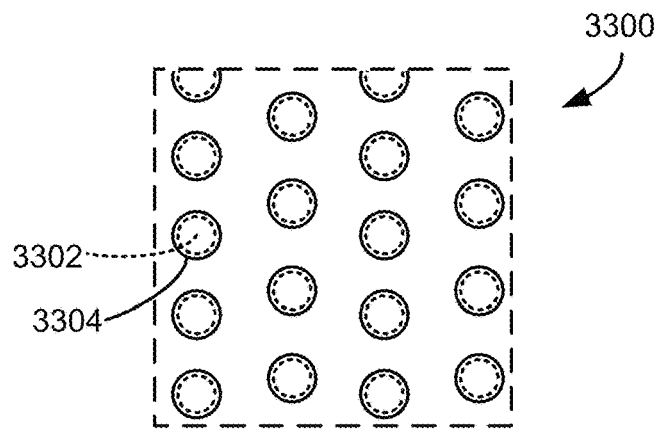
FIGS. 33-35 illustrate various implementations of protrusion reinforcement on internal surfaces of balloons in accordance with the present disclosure.
Figure 34:
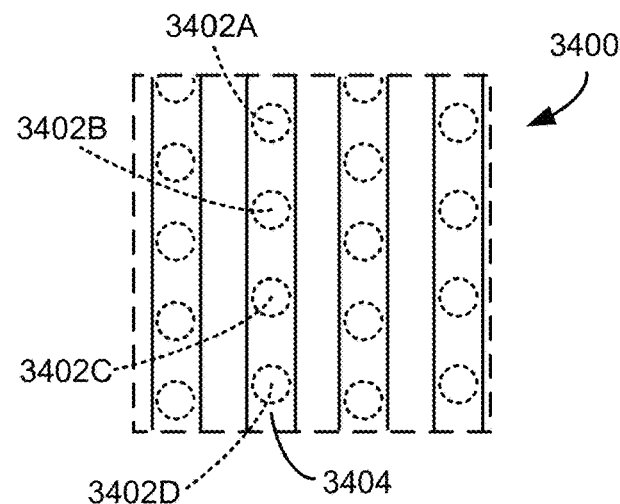
Figure 35:
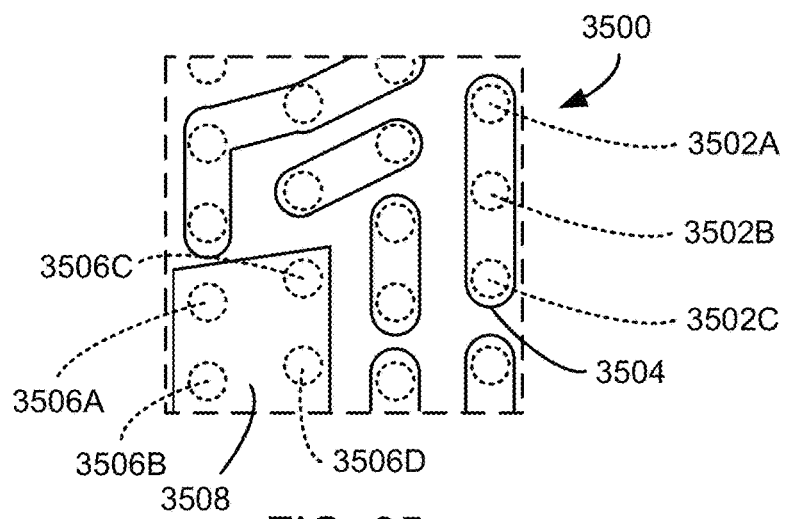

In certain implementations of the present disclosure, protrusions extending from the balloon may be reinforced to increase overall rigidity of the protrusions, thereby preventing or reduce bending or other deformation during transportation of the balloon within a physiological lumen or following anchoring of the balloon within the lumen. In certain implementations, such reinforcement of the protrusions may be provided on the internal surface of the balloon. For example, FIGS. 33-35 each illustrate non-limiting examples of internal reinforcement that may be applied to the protrusions. FIG. 33, for example, illustrates a portion 3300 of an example inner balloon surface in which each protrusion (e.g., protrusion 3302) is individually reinforced by a corresponding bump (e.g., bump 3304 corresponding to protrusion 3302) or similar localized thickening of the balloon wall opposite the protrusion. As another example, FIG. 34 illustrates a portion 3400 of another example inner balloon surface in which multiple protrusions (e.g., protrusions 3402A-3402D) are linked by a corresponding ridge, rib, or similar reinforcing structure (e.g., rib 3404) extending along the inner surface of the balloon. FIG. 35 illustrates another portion 3500 of an example inner balloon surface illustrating that such reinforcement may be non-uniform. For example, while protrusions 3502A-3502C are reinforced using a common and straight rib 3504, protrusions 3506A-3406D are reinforced by a patch 3508 of balloon material.

Figure 36:
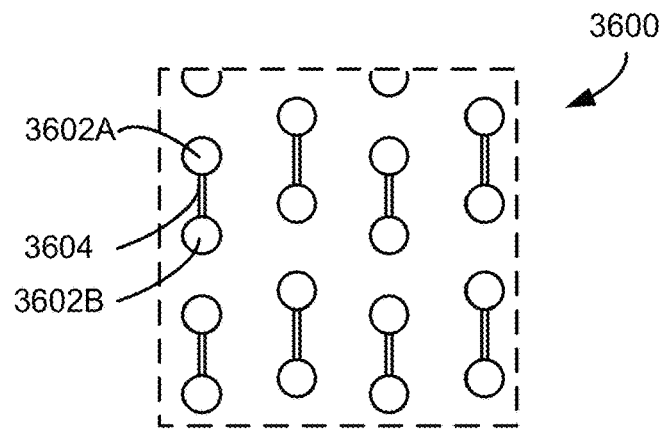
FIGS. 36-38 illustrate various implementations of protrusion reinforcement on external surfaces of balloons in accordance with the present disclosure.
Figure 37:
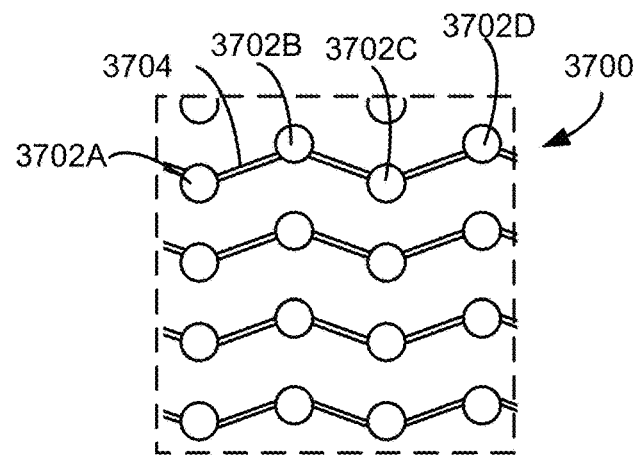
Figure 38:
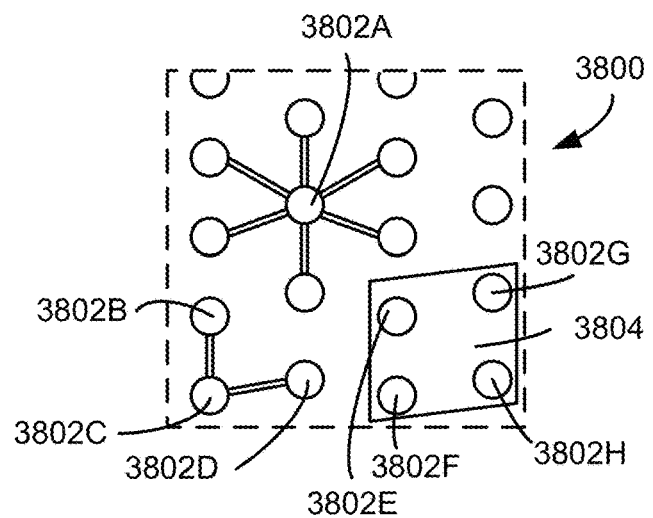

Reinforcement of the protrusions may also be achieved by linking or connecting protrusions on the exterior surface of the balloon. For example, FIG. 36 illustrates a portion 3600 of an external surface of a first example balloon in which adjacent protrusions (e.g., protrusions 3602A, 3602B) are linked or otherwise mutually reinforced by a rib 3604 extending therebetween. FIG. 37 illustrates a portion 3700 of a second example balloon in which protrusions (e.g., protrusions 3702A-3702D) are linked by continuous ribs (e.g., rib 3704). Finally, FIG. 38 illustrates a portion 3800 of a third example balloon having non-uniform protrusion reinforcement. For example, protrusion 3802A is coupled to and reinforced by each of its nearest neighboring protrusions, protrusions 3802-3802D are reinforced to form an "L" shaped pattern, and protrusions 3802E-3802H are reinforced by a patch 3804 or pad extending therebetween.

The foregoing examples of internal and external protrusion reinforcement are intended merely as non-limiting examples. More generally, reinforcement of protrusions in accordance with the present disclosure may be achieved by either or both of providing additional material on the inner surface of the balloon opposite the protrusions, providing additional material on the external surface of the balloon adjacent the protrusions, or forming a mechanical link between protrusions, such as by forming a rib or similar structure extending between protrusions.

The foregoing balloon designs are intended merely as examples and are not intended to limit the scope of the present disclosure. Rather, features of any balloon disclosed herein may be combined in any suitable manner. For example, any size, shape, and arrangement of protrusions may be implemented with any corresponding balloon shape or size. Similarly, other features, such as those related to controlled collapse, may be incorporated into any balloon design disclosure herein. Similarly, any specific dimensions or proportions provided in the context of specific balloon designs are intended merely as examples and should not be construed as limiting. More generally, any particular implementations of balloons discussed or illustrated herein should be regarded as one possible combination of features of balloons in accordance with the present disclosure.

Overtube Assemblies Including Balloon Inflation/Deflation Systems

An endoscopic overtube is a sleeve-like device designed to facilitate endoscopic procedures. During upper endoscopic procedures, for example, overtube may be used to protect, among other things, the hypopharynx from trauma during intubations, the airway from aspiration, and the esophagus during extraction of sharp foreign bodies. Similarly, during lower endoscopic procedures, such as enteroscopy and colonoscopy, overtubes may be used to protect various structures of the gastrointestinal tract while also preventing loop formation.

In endoscopic processes including endoscopic balloons, the balloon may be coupled to the overtube and the overtube may include passageways or ducts that extend along its length from the balloon to one or more proximal ports. For example, certain conventional balloon overtubes include a balloon and overtube with an inflation/deflation port and a fluid access port. Such conventional balloon overtubes are often operated using a separate and cumbersome inflation system coupled to the overtube by one or more small plastic tubes. The inflation system generally includes a pump and valves for providing air to and extracting air from the inflation/deflation port of the overtube via the plastic tubes. Such systems may be actuated by foot pedal or handheld button, either by the gastroenterologist user, or by a technician.

Among other issues, such conventional inflation systems are expensive to purchase and operate, time consuming to set up, and lack portability. Accordingly, such conventional systems generally preclude balloon endoscopy from being used in facilities that may lack the resources for a conventional system or in applications outside of an endoscopic center.

To address the foregoing issues, among others, an improved overtube assembly is provided. The improved overtube assembly includes an inflation/deflation system integrated with the overtube to provide a standalone or substantially standalone system.

Figure 39:
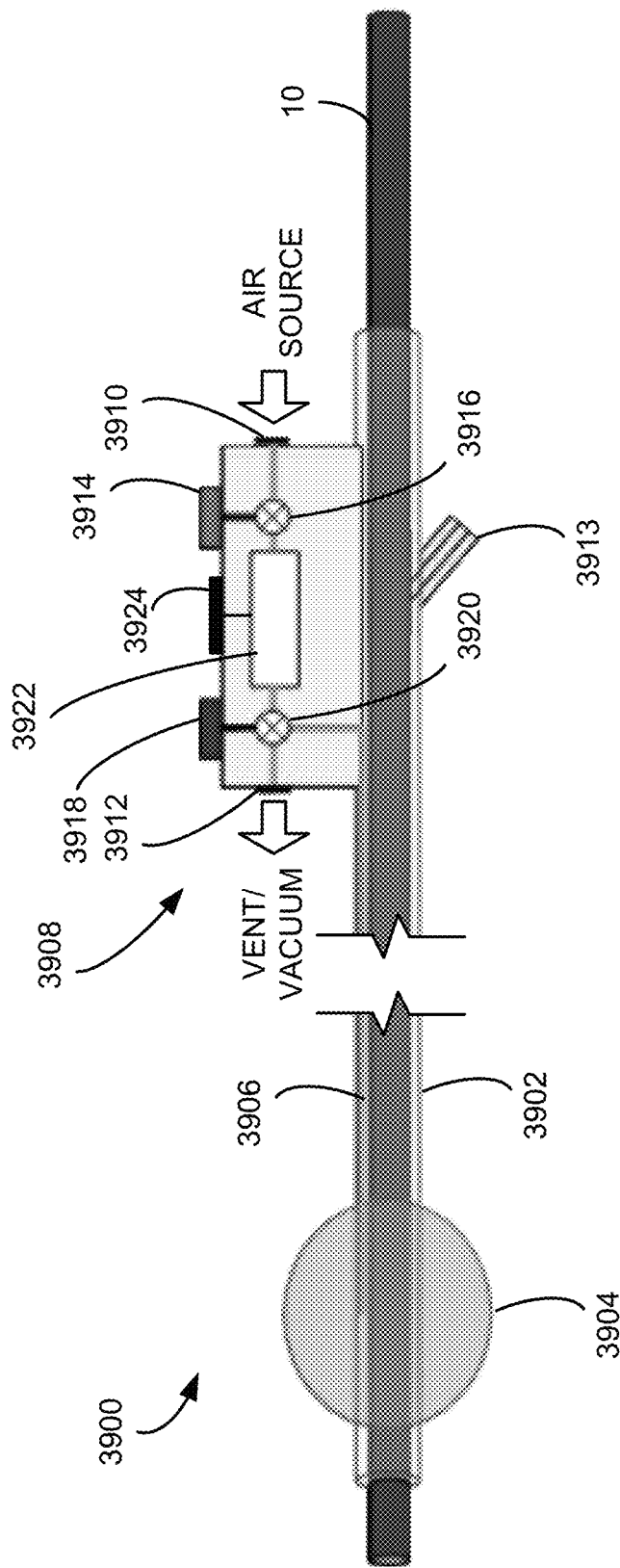
FIG. 39 is a schematic illustration of an overtube assembly according to the present disclosure including an integrated inflation/deflation assembly.

FIG. 39 is a schematic illustration of an example overtube assembly 3900 in accordance with the present disclosure. As illustrated, the overtube assembly 3900 is disposed on an endoscope 10. The overtube assembly 3900 includes an overtube 3902 coupled to a balloon 3904. A balloon line 3906 extends along or through the overtube 3902 from the balloon 3904 to an inflation/deflation assembly 3908. In certain implementations, the balloon line 3906 may be a lumen defined by the overtube 3902; however, in other implementations, the balloon line 3906 may be a separate lumen coupled to or embedded within the overtube 3902.

The balloon 3904 may be, but is not necessarily limited to, an endoscopic balloon including one or more textured portions according to any implementation discussed herein.

The inflation/deflation assembly 3908 includes various ports and controls to facilitate the inflation and deflation of the balloon 3904. For example, the inflation/deflation assembly 3908 includes each of an inflation port 3910 and a deflation port 3912. The inflation port 3910 is adapted to be coupled to a suitable source of pressurized air (not shown), which may include, without limitation, "house air" available within an endoscopy or operation room suite, a hand pump, a hand syringe, a foot-actuated floor pump, or a reservoir of compressed air. Similarly, the deflation port 3912 may be configured to be coupled to a vacuum to facilitate rapid deflation of the balloon 3904. Alternatively, the deflation port 3912 may vent to atmosphere. The overtube assembly 3900 may further include other ports, such as, but not limited to, a fluid in/out port 3913 to facilitate injection or removal of fluid from the physiological lumen within which the overtube assembly 3900 is disposed.

The inflation/deflation assembly 3908 further includes controls for selectively inflating and deflating the balloon 3904. In the specific implementation illustrated in FIG. 39, for example, the inflation/deflation assembly 3908 includes each of an inflation button 3914 for selectively opening an inflation valve 3916 and a deflation button 3918 for selectively opening a deflation valve 3920. When opened (e.g., by depressing the inflation button 3914), the inflation valve 3916 permits air flow from the air source through a regulator 3922 of the inflation/deflation assembly 3908 and to the balloon 3904 via the balloon line 3906. Similarly, when opened, the deflation valve 3920 permits air flow from the balloon 3904, through the balloon line 3906, and out of the deflation port 3912.

As noted, the inflation/deflation assembly 3908 may include a regulator 3922 disposed between the inflation port 3910 and the balloon line 3906. In certain implementations, the regulator 3922 may be fixed to provide a predetermined flow rate at a predetermined pressure; however, in at least some implementations the regulator 3922 may be adjustable (e.g., by an adjustment knob 3924 or similar control element coupled to the regulator 3922).

The various control elements included in the inflation/deflation assembly 3908 may be mechanical, electronic, or a combination of both. In implementations in which electronic components are included, the inflation/deflation assembly 3908 may generally include suitable circuitry, memory, and processing components to perform various functions such as, but not limited to, receiving inputs from the buttons 3914, 3918; actuating the valves 3916, 3920; and adjusting the regulator 3922. In certain implementations the inflation/deflation assembly 3908 may also be communicatively coupled to one or more remote computing devices that may be used to operator and/or collect data from the inflation/deflation assembly 3908. To the extent any electronic components are included in the inflation/deflation assembly 3908, the inflation/deflation assembly 3908 may further include an onboard power source (such as a battery) and/or may be electrically coupleable to an external power source, such as a wall socket or external battery.

In certain implementations, the inflation/deflation assembly 3908 may include an onboard pump between the inflation port 3910 and the regulator 3922 and the inflation port 3910 may simply be open to ambient air. In such implementations, the inflation/deflation assembly 3908 may further include one or more permanent or replaceable filter element disposed between the inflation port 3910 and the regulator 3922 to improve the quality of the air provided to the balloon 3904.

As shown in FIG. 39, the inflation/deflation assembly 3908 may be directly coupled to a proximal portion of the overtube 3902. In certain implementations, the inflation/deflation assembly 3908 may be specifically sized and shaped to be manipulated using one hand, thereby improving ease of use and freeing a user's second hand to perform other tasks. Accordingly, the size and shape of the inflation/deflation assembly 3908 may be chosen for any of right-, left-, or ambidextrous operation.

In at least certain implementations, the overtube assembly 3900, including the inflation/deflation assembly 3908, may be configured to be disposable in whole or in part. For example, in certain implementations, the overtube assembly 3900 may be disassembled in whole or in part, with certain of the components of the overtube assembly 3900 being recyclable or otherwise readily disposable.

It should be understood that the foregoing overtube assembly 3900 is merely an example and implementations of the present disclosure are limited to the specific implementation discussed above. Rather, overtube assemblies in accordance with the present disclosure more generally include an overtube to which flow and pressure regulating components are coupled and with which such flow and pressure regulating components are integrated into a unitary assembly.

Split Overtubes

Conventional overtubes, including balloon overtubes, are continuous tubular structures. As a result, such overtubes may only be installed on endoscopes (or similar tools) by inserting a distal end of the endoscope into a proximal end of the overtube and extending the endoscope through the overtube. This process necessarily requires that the endoscope be outside the patient and, as a result, must be performed at the outset of any endoscopic procedure. In certain instances, however, a physician may not know whether an overtube is required until mid-procedure. At such time in the procedure, it may be very difficult to fully intubate the patient due to irregular anatomy, or other complications. Physicians also sometime realize they cannot easily position the endoscope to successfully biopsy tissue. In these example cases, a physician would generally need to remove the endoscope from the patient, attach an overtube, re-intubate the patient, and deliver the endoscope to its prior location. This leads to increased procedure time and challenges of advancing the scope to the previous furthest point. Thus, there is a need to be able to attach an overtube mid-procedure and, more specifically, to attach an overtube to the endoscope and advance the overtube to the tip of the endoscope without losing any purchase with the endoscope, removing the endoscope from the patient, or otherwise backtracking in the procedure.

To address the foregoing issues, among others, a split or wraparound overtube is provided here. In general, the split overtube includes a longitudinally extending split that allows the overtube to be opened and placed onto an endoscope. To prevent separation of the split overtube and/or disengagement from the endoscope, the split overtube may include features to secure the overtube to the underlying endoscope. For example, in certain implementations, the overtube may have a high-friction inner surface adapted to frictionally engage the endoscope. Such high-friction properties may be a result of the material of the split overtube, a coating or adhesive applied to the inner surface, texturing of the inner surface, and the like. In certain implementations, friction between the overtube and the endoscope may be selectively modified by introducing a fluid into the annular space between the overtube and the endoscope, such that the fluid acts as a lubricant between the two components.

The overtube may also include features to prevent the overtube from splitting once coupled to the endoscope. For example, in certain implementations surfaces of the overtube that contact when closed about an endoscope may be textured or treated to frictionally engage each other. In certain implementations, the overtube may be configured to wrap about the endoscope such that portions of the overtube overlap. Like the previously mentioned contacting surfaces, the overlapping portions of the overtube may also include coatings, texturing, or structural features configured to engage each other and maintain the overtube in a closed configuration about the endoscope.

Referring first to FIGS. 40A and 40B, an endoscope and overtube assembly 4000 is illustrated in each of a separated and coupled configuration. More specifically, FIG. 40A illustrates the endoscope 20 adjacent the overtube 4004. The overtube 4004 includes a split 4006 extending along its length such that the overtube 4004 may be opened (e.g., into a "C"-shape) and an exposed/ex vivo portion of the endoscope 20 may be inserted laterally into the overtube 4004. Although illustrated in FIGS. 40A and 40B as being straight, the split 4006 more generally extends along the full length of the overtube 4004, but may extend both about and along the overtube 4004 in doing so. For example, instead of a straight split (such as illustrated), the split 4006 may be helical or include helically extending segments. FIG. 40B illustrates the endoscope and overtube assembly 4000 in an assembled configuration in which the endoscope 20 is disposed within the overtube 4004. Once disposed on the endoscope 20, the overtube 4004 may be advanced along the endoscope 20 (e.g., in vivo) to the tip of the endoscope 20.

Figure 42:
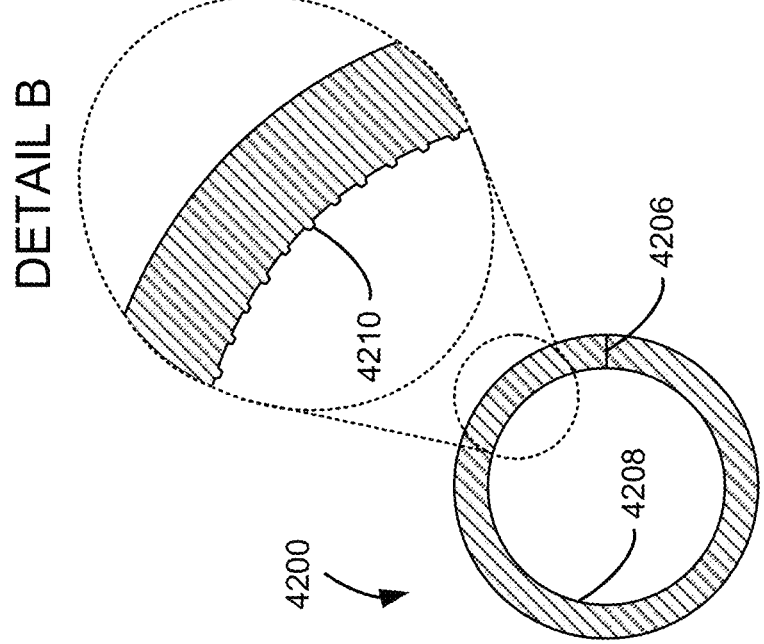
FIG. 42 is a cross-section view of the split overtube of FIGS. 23A-23B including inner texturing.
Figure 41:
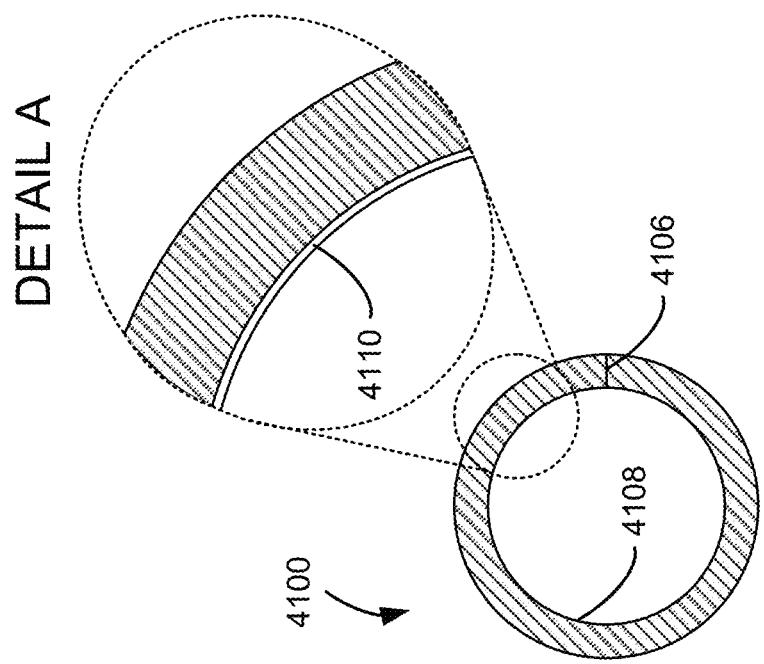
FIG. 41 is a cross-section view of the split overtube of FIGS. 23A-23B including an inner layer/coating.

Although the overtube may be advanced along the endoscope 20, in certain implementations, the frictional engagement between the endoscope 20 and the overtube 4004 may be designed to provide at least some resistance to undesirable movement of the endoscope 20 relative to the overtube 4004 once the overtube 4004 is installed. FIGS. 41 and 42 provide two example approaches of modifying the engagement between the endoscope 20 and overtube 4004.

Referring first to FIG. 41, a cross-sectional view of a first example overtube 4100 is provided. As illustrated, the overtube 4100 includes a split 4106 that allows the overtube 4100 to be opened for insertion of the endoscope. As illustrated in Detail A, at least a portion of the inner surface 4108 of the overtube 4100 may include a coating or layer 4110 with predetermined frictional properties. Similarly, FIG. 42 is a cross-sectional view of a second example overtube 4200 is provided. As illustrated, the overtube 4200 also includes a split 4206 that allows the overtube 4200 to be opened for insertion of the endoscope. As illustrated in Detail B, at least a portion of the inner surface 4208 of the overtube 4200 may include texturing 4210 to modifying the frictional properties of the inner surface 4208. Although various textures may be used, in at least certain implementations, such texturing 4210 may be similar to the texturing described above in the context of endoscopic balloons. It should be appreciated that similar coating or texturing may also be applied to portions of the exterior surface of the overtubes 4100, 4200 to modify the frictional engagement between the overtubes 4100, 4200 and any physiological lumen within which they may be used.

FIGS. 43-46 illustrate alternative configurations of split overtubes in accordance with the present disclosure and, in particular, different ways in which such overtubes may be retained on an endoscope.

Figure 43:
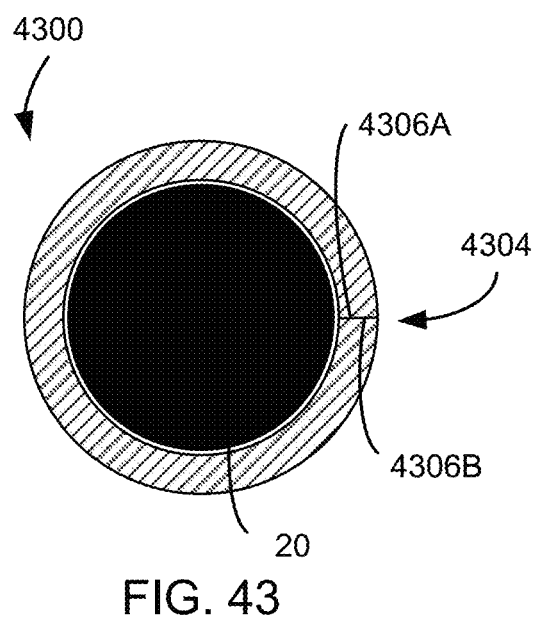
FIGS. 43-46 are cross-sectional views of alternative split overtubes.

Referring first to FIG. 43, a cross-sectional view of an overtube 4300 disposed on an endoscope 20 is provided. As illustrated, the overtube 4300 includes a lateral split 4304 including a first surface 4306A and a second surface 4306B. As illustrated, when disposed on the endoscope 20, the first surface 4306A and the second surface 4306B abut. In certain implementations, the overtube 4300 may be formed from a material having sufficient rigidity that the first surface 4306A and the second surface 4306B are in positive contact. Alternatively or in addition, one or both of the first surface 4306A and the second surface 4306B may have a coating, layer, texture, adhesive, or similar treatment to increase frictional engagement between the first surface 4306A and the second surface 4306B.

Figure 44:
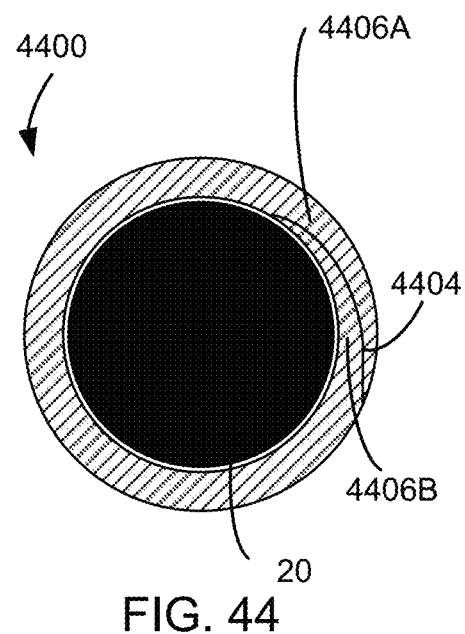

FIG. 44 is a cross-sectional view of another overtube 4400 disposed on the endoscope 20. As illustrated, the overtube 4400 includes a split 4404 formed between overlapping portions of the overtube 4400. More specifically, when disposed about the endoscope 20 a first portion 4406A of the overtube 4400 is disposed inwardly of a second portion 4406B of the overtube 4400, forming an interface between the inward surface of the first portion 4406A and the outward surface of the second portion 4406B. In certain implementations, the overtube 4400 may be formed from a material having sufficient rigidity that the first portion 4406A of the overtube 4400 is maintained in positive contact with the second portion 4406B of the overtube 4400. Alternatively or in addition, one or both of the inward surface of the first portion 4406A and the outer surface of the second portion 4406B may have a coating, layer, texture, or similar treatment to increase frictional engagement at the interface between the two portions 4406A, 4406B.

Figure 45:
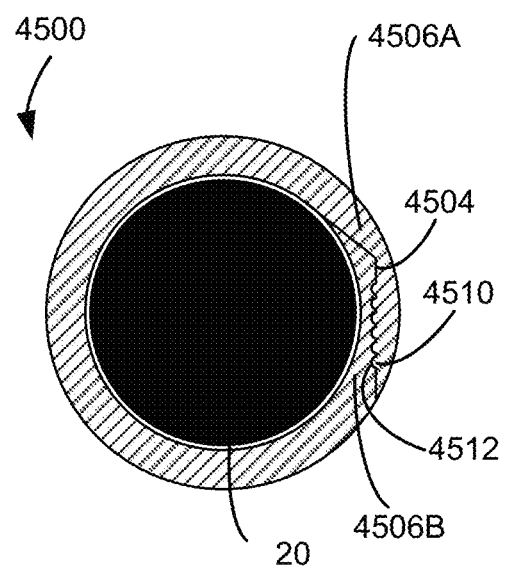

FIG. 45 is a cross-sectional view of another overtube 4500 disposed on the endoscope 20. As illustrated and similar to the overtube 4400 of FIG. 44, the overtube 4500 includes a split 4504 formed between overlapping portions of the overtube 4500. More specifically, when disposed about the endoscope 20 a first portion 4506A of the overtube 4500 is disposed inwardly of a second portion 4506B of the overtube 4500, forming an interface between the inward surface of the first portion 4506A and the outward surface of the second portion 4506B. In addition to the overlap at the interface, the first portion 4506A and the second portion 4506B may include mating or engaging structures. For example, as illustrated in FIG. 45, the first portion 4506A includes a series of longitudinal ridges 4510 shaped to be received by corresponding longitudinal grooves 4512 defined in the second portion 4506B.

Figure 46:
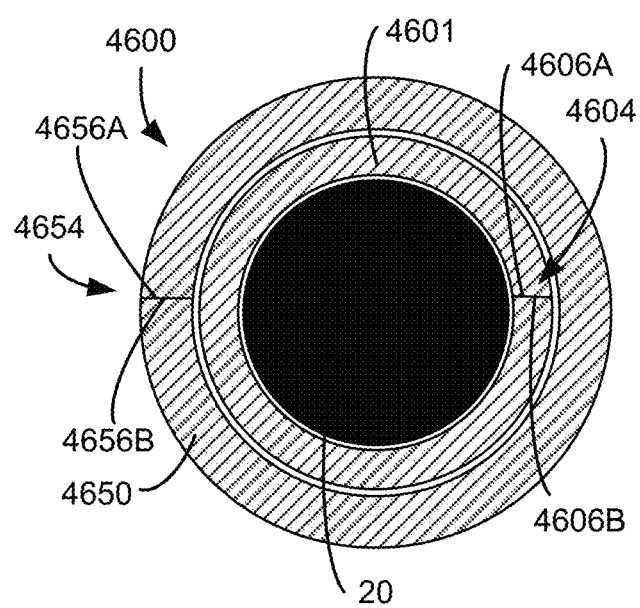

As yet another example, FIG. 46 is a cross-sectional view of an overtube assembly 4600 disposed on the endoscope 20. As illustrated, the overtube assembly 4600 includes multiple overtubes and, more specifically an inner overtube 4601 and an outer overtube 4650. Each of the inner overtube 4601 and the outer overtube 4650 may be similar to any of the other split overtube designs discussed herein; however, for purposes of the current example, each of the inner overtube 4601 and the outer overtube 4650 are similar to the overtube 4300 of FIG. 43. More specifically, the inner overtube 4601 includes a lateral split 4604 including a first surface 4606A that abuts a second surface 4606B. Similarly, the outer overtube 4650 includes a lateral split 4654 including a first surface 4656A that abuts a second surface 4656B, the lateral split 4654 enabling insertion of the inner overtube 4601 with the endoscope 20 therein to be received within the outer overtube 4650. In certain implementations the inner overtube 4601 may be rotatable or otherwise movable within the outer overtube 4650.

It should be appreciated that in at least some implementations, the outer overtube 4650 extend along only a portion of the inner overtube 4601. In such implementations, multiple outer overtubes may also be distributed along the length of the inner overtube 4650. In still other implementations the outer overtubes 4650 may instead be substituted with split rings, straps, clips, or similar components adapted to extend around and maintain the inner overtube 4601 in a closed configuration.

Further aspects of overtubes and overtube assemblies in accordance with the present disclosure are now provided with reference to FIGS. 47-63, which illustrate another example overtube assemblies and associated methods of manufacturing.

FIGS. 47-50 are an isometric view, a plan view, an elevation view, and a distal end view of the overtube assembly 4700. As previously discussed, the overtube assembly 4700 may be disposed on an elongate/tubular medical tool. For purposes of the following discussion, the tubular medical device is generally referred to as an endoscope, however, it should be understood that the overtube assembly 4700 may be configured to work with other medical devices having generally tubular shapes, including medical devices other than endoscopes.

Figure 47:
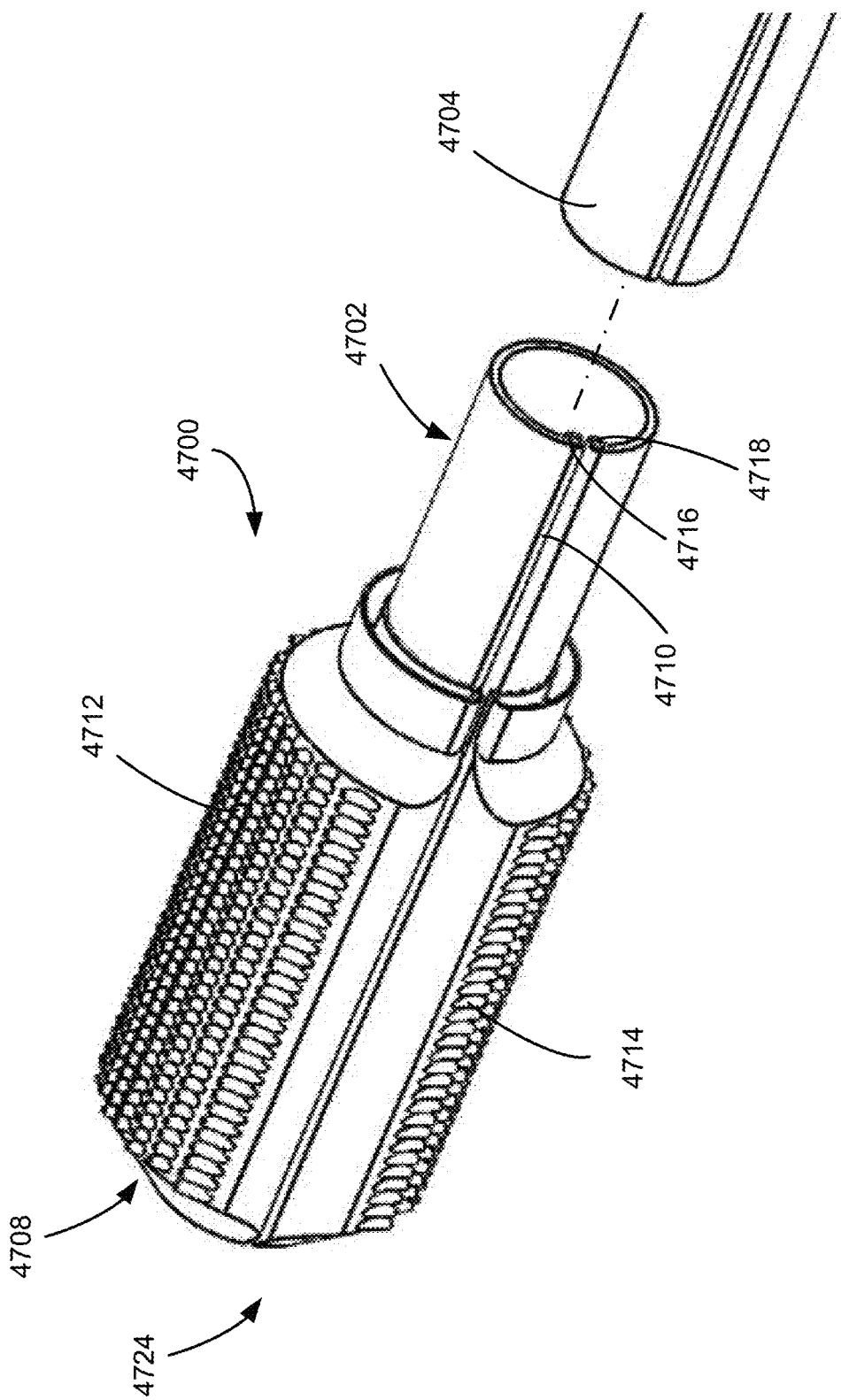
FIG. 47 is an isometric view of a distal portion of a split overtube assembly in accordance with the present disclosure.

As illustrated in FIG. 47, the overtube assembly 4700 includes an overtube 4702 having a flexible tubular body 4704. The tubular body 4704 generally includes a proximal end 4706 (indicated in FIGS. 48 and 49) and a distal end 4708. The tubular body 4704 defines a split 4710 extending from the proximal end 4706 to the distal end 4708. As noted in the context of the foregoing example overtubes, the split 4710 permits the overtube assembly 4700 to receive an elongate medical tool, such as an endoscope, by inserting the tool through the split 4710 as opposed to passing the tool through a lumen defined by the tubular body 4704. Notably, in at least some implementations, the split 4710 may include overlapping portions of the tubular body 4704 as previously discussed in the context of FIGS. 43-46.

The overtube assembly 4700 may further include one or more inflatable balloons, such as inflatable balloon 4712 and 4714, which are illustrated as being disposed on opposite sides of the tubular body 4704 on a distal portion 4724 of the tubular body 4704. Air may be provided to or removed from each of the inflatable balloons 4712, 4714 via respective air supply lumens 4716, 4718 defined by and extending through the tubular body 4704. Although not illustrated, in at least certain implementations, each of the air supply lumens 4716, 4718 may extend fully through the tubular body 4704 and may be capped by an insert or otherwise sealed at the distal end 4708 of the tubular body 4704. Also, while not illustrated, the proximal end of each air supply lumen 4716, 4718 may be coupled to one or more pumps or similar air supply devices that provide air to, remove air from, ventilate, etc. the inflatable balloons 4712, 4714. Although described herein as an "air supply lumen", similar lumens may be implemented that deliver any suitable fluid to or remove fluid from the inflatable balloons 4712, 4714.

Although the overtube assembly 4700 includes inflatable balloons 4712, 4714, in other implementations, the inflatable balloons 4712, 4714 may be omitted or replaced with other fluid-controlled features. In implementations in which the balloons are removed and not replaced with another device, the air supply lumens 4716, 4718 may be omitted. The inflatable balloons of other implementations discussed herein may similarly be omitted.

Figure 50:
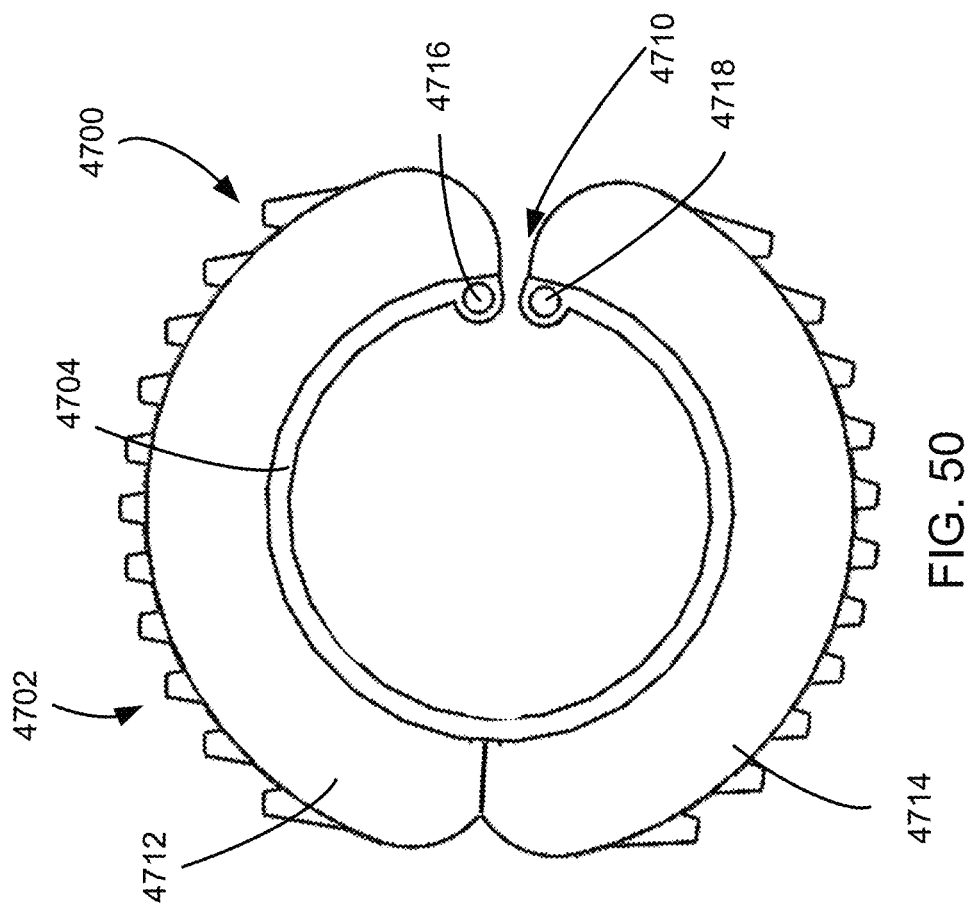
FIG. 50 a distal end view of the distal portion of the split overtube assembly of FIG. 47.

As most clearly shown in FIG. 50, in at least some implementations, the air supply lumens 4716, 4718 may be disposed on opposite sides of the split 4710 and may generally run parallel to the split 4710. In other implementations, the air supply lumens 4716, 4718 may be defined within the tubular body 4704 at a location other than adjacent the split 4710. Moreover, while the air supply lumens 4716, 4718 are shown as extending in a longitudinal direction, in other implementations, the air supply lumens 4716, 4718 may also extend in a circumferential direction as well. Also, while the split 4710 extends along the full length of the tubular body 4704, the air supply lumens 4716, 4718 may only extend along a portion of the tubular body 4704 sufficient to extend from the proximal end 4706 of the overtube 4702 to the inflatable balloons 4712, 4714.

Figure 48:
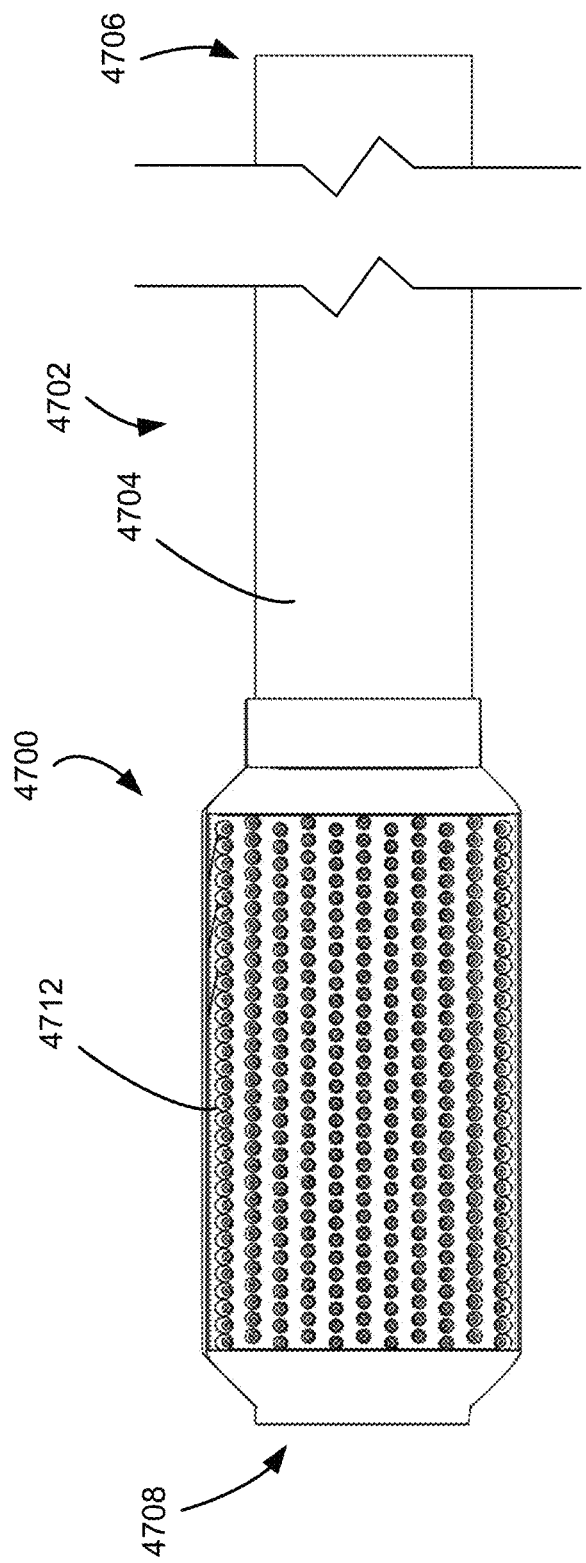
FIG. 48 is a plan view of the distal portion of the split overtube assembly of FIG. 47.
Figure 49:
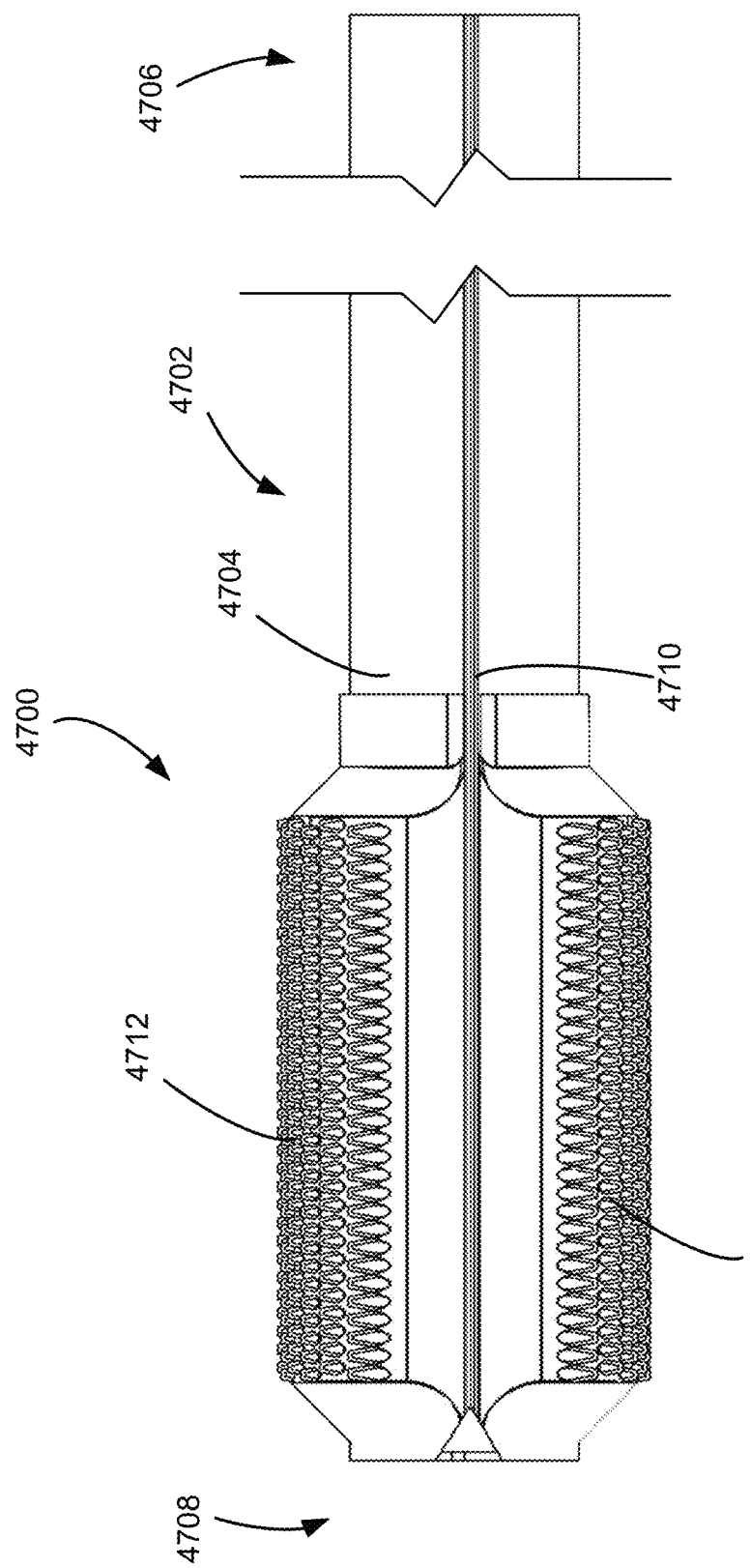
FIG. 49 is a side elevation view of the distal portion of the split overtube assembly of FIG. 47.

Although illustrated in FIGS. 47-49 as being a single tubular structure, in at least certain implementations, the tubular body 4704 may be embedded with or otherwise include additional structural elements and features. For example, the tubular body 4704 may include reinforcement in the form of ribs, ridges, or other similar structural elements disposed along the length of the tubular body 4704. In certain implementations, such structural elements may be integrally formed with the tubular body 4704. In other implementations, such structural elements may instead be separate components that are embedded within, attached to, or otherwise coupled to the tubular body 4704. As another example, the tubular body 4704 may include one or more radiopaque markers to facilitate viewing of the overtube assembly 4700 using fluoroscopy. Similar to the reinforcing structures, in at least certain implementations such markers may be embedded within or attached to the tubular body 4704.

As noted above, in the specific implementation illustrate in FIGS. 47-49, the overtube assembly 4700 includes two inflatable balloons 4712, 4714 that are disposed near the distal end of the overtube 4702 and on opposite sides of the overtube 4702. As shown, the inflatable balloons 4712, 4714 include texturing in the form of frustoconical projections, similar to those of the balloon 2500 illustrated in FIGS. 25A-25D and discussed above. Although illustrated with frustoconical projections, it should be understood that the inflatable balloons 4712, 4714 may include any texturing disclosed herein on their exterior surfaces. It should also be appreciated that in at least some implementations, at least one of the inflatable balloons 4712, 4714 may be untextured.

This specific arrangement is provided merely as an example and other configurations are contemplated. For example, in certain implementations the overtube assembly 4700 may include any suitable number of inflatable balloons, including one. Also, the one or more inflatable balloons may be disposed at any location along the overtube 4702. To the extent the overtube assembly 4700 includes multiple inflatable balloons, such balloons may be disposed at different longitudinal locations along the overtube 4702. Similarly, while the inflatable balloons 4712, 4714 collectively extend around substantially the full circumference of the overtube assembly 4700, in other implementations, the inflatable balloons may instead be disposed only on one side of the overtube 4702 or otherwise extend around only a portion of the circumference of the overtube 4702.

Figure 51:
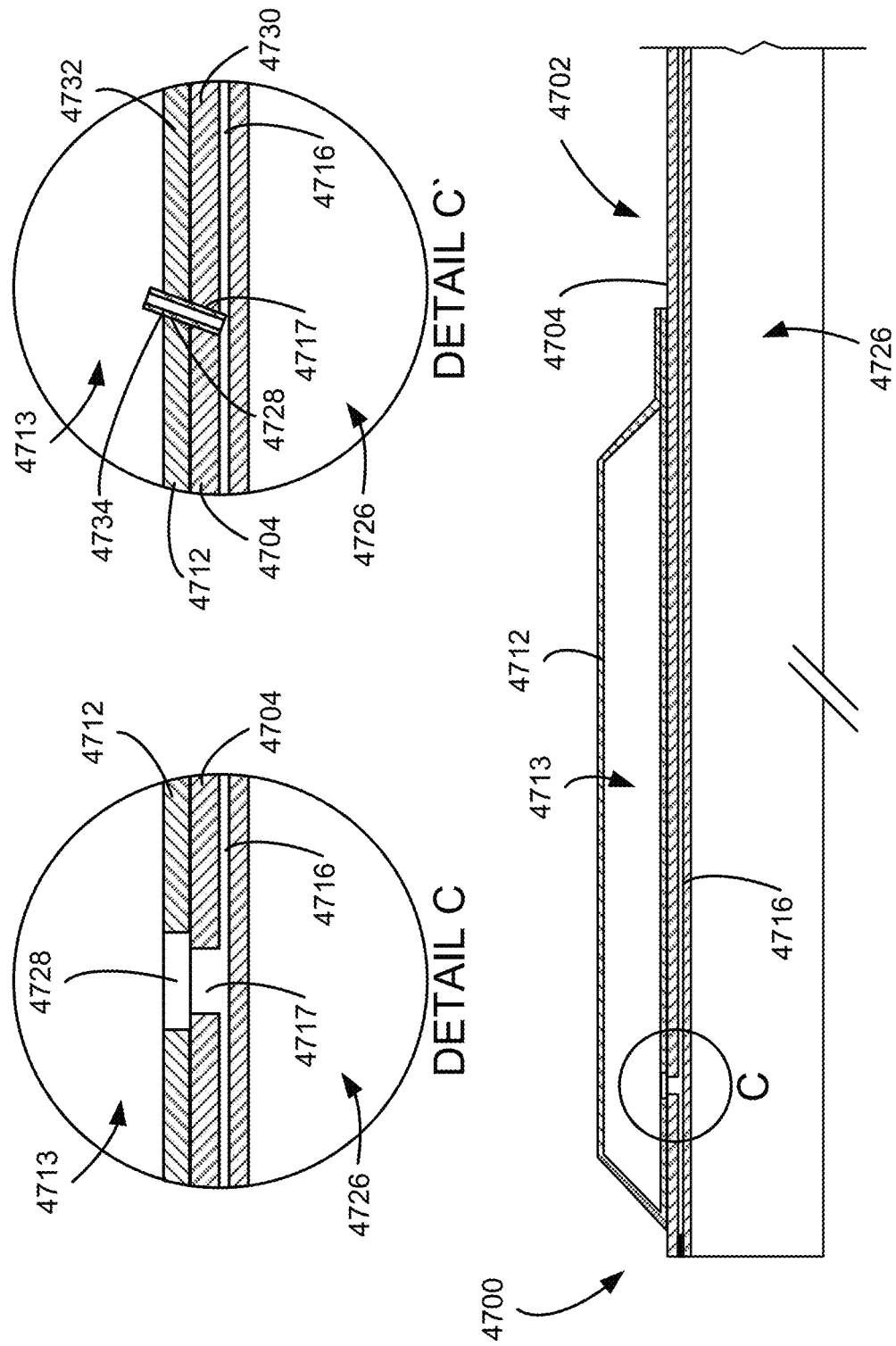
FIG. 51 is a cross-sectional side view of the distal portion of the split overtube assembly of FIG. 47.

FIG. 51 is a partial longitudinal cross-section of the overtube assembly 4700. As illustrated, the tubular body 4704 of the overtube 4702 defines a tubular cavity 4726 within which the endoscope 20 or other medical tool is received via the split 4710 (shown in FIG. 49). FIG. 51 further illustrates the air supply lumen 4716, which is defined by and extends along the tubular body 4704. Each air supply lumen defined by the tubular body 4704 is in communication with an internal volume of one or more of the inflatable balloons 4712, 4714 (texturing of the balloons is omitted in FIG. 51 for clarity). In the specific example of the overtube assembly 4700, for instance, the air supply lumen 4716 is in communication with an internal volume 4713 of the inflatable balloon 4712. More specifically, the tubular body 4704 defines an overtube port 4717 in communication with the air supply lumen 4716. The inflatable balloon 4712 similarly defines a balloon port 4728 in communication with the internal volume 4713. During assembly and as illustrated in Detail C of FIG. 51, the inflatable balloon 4712 is coupled to the tubular body 4704 such that the overtube port 4717 and the balloon port 4728 are also in communication, thereby enabling air flow between the internal volume 4713 of the balloon 4712 and the air supply lumen 4716 during use of the overtube assembly 4700.

In certain implementations, each of the overtube port 4717 and the balloon port 4728 may be formed after initial extruding, molding, etc. of the tubular body 4704 and the balloon 4712. For example, following extrusion of the tubular body 4704, the overtube port 4717 may be formed by cutting, puncturing, etc. a wall 4730 of the tubular body 4704. Similarly, following forming of the balloon 4712, a wall 4732 of the balloon 4712 may be cut, punctured, etc. to form the balloon port 4728. Alternatively, in either case, either of the overtube port 4717 or the balloon port 4728 may be formed directly during the extrusion, molding, etc. process.

In certain implementations, a hollow conduit 4734 or similar reinforcing structure may also extend between the overtube port 4717 and the balloon port 4728 and provide an air channel between the internal volume 4713 of the inflatable balloon 4712 and the air supply lumen 4716. The hollow conduit 4734 may be inserted after formation of the overtube port 4717 and the balloon port 4728. In other implementations and as illustrated in Detail C', the conduit 4734 may alternatively be used to puncture each of the wall 4730 of the tubular body 4704 and the wall 4732 of the balloon 4712 to form each of overtube port 4717 and the balloon port 4728.

Figure 52:
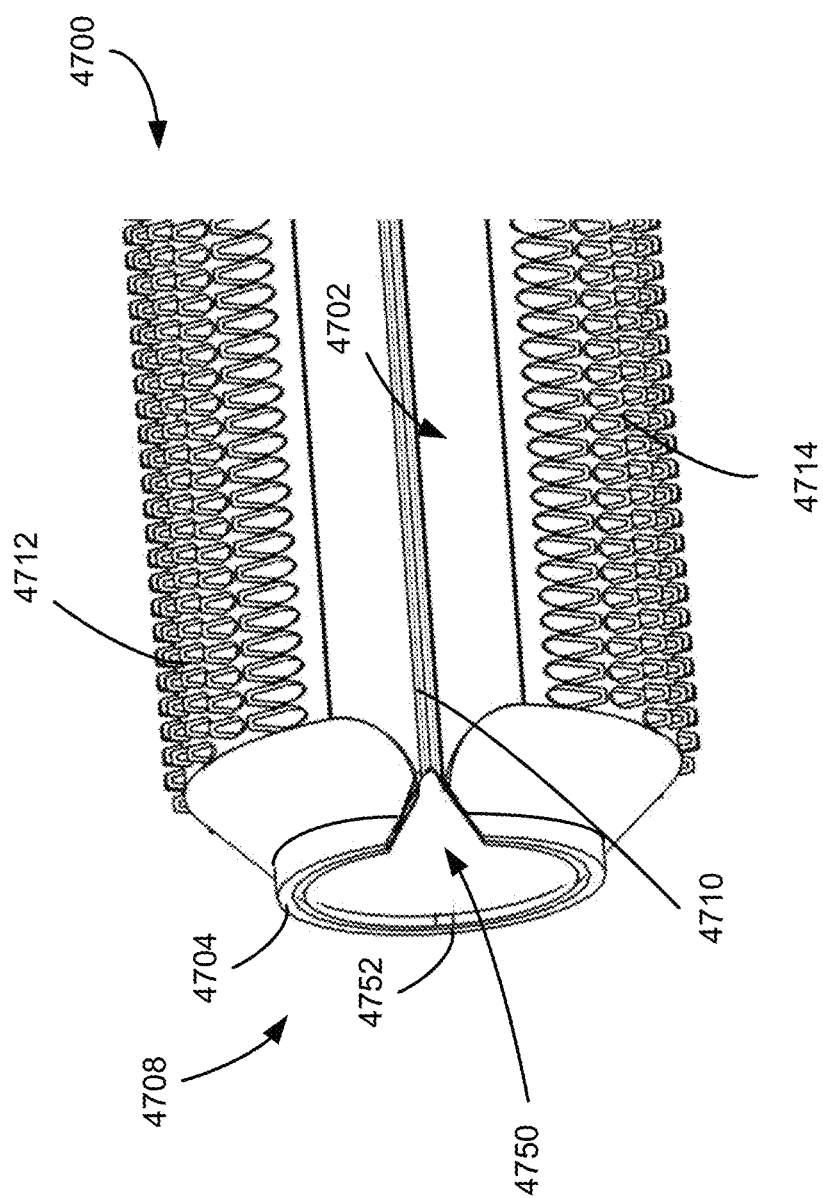
FIG. 52 is a detailed view of a distal end of the split overtube assembly of FIG. 47.

FIG. 52 is a detailed view of the distal end 4708 of the overtube assembly 4700. Among other things, FIG. 52 illustrates the inclusion of a notch 4750 formed in the distal end of the tubular body 4704, which may be included in implementations of the present disclosure. As illustrated, the notch 4750 generally extends proximally from a distal end 4752 of the tubular body 4704, tapering toward the split 4710, and ultimately being in communication with the split 4710

The notch 4750 is provided to facilitate placement of the overtube assembly 4700 onto an elongate medical tool, such as an endoscope. More specifically, when disposing the overtube assembly 4700 onto the elongate medical tool, the elongate medical tool is first placed within the notch 4750. As the overtube 4702 is forced onto the tool, the notch 4750 provides a wedge-like action that opens the overtube 4702 along the split 4710, thereby facilitating placement of the overtube assembly 4700 onto the tool. Inclusion of the notch 4750 is particularly useful in implementations in which the overtube 4702 is particularly thick or stiff and, as a result, separation along the split 4710 may be difficult without the added leverage afforded by the notch 4750. Although the notch 4750 is shown as being triangular in FIG. 52, in other implementations, the notch 4750 may have other shapes. However, in general, the notch 4750 begins at the distal end 4752 of the overtube 4702 and tapers proximally.

FIGS. 53 and 54 are an isometric view and an end view, respectively, of the inflatable balloon 4712 of the overtube assembly 4700. More specifically, FIGS. 53 and 54 illustrated the inflatable balloon 4712 in an unstrained state. Similar to the previously disclosed balloons, the balloon 4712 includes an elongate body 5302 including a middle portion 5304 and tapering end portions 5306A, 5306B. In contrast to the balloons previously disclosed herein, which had a substantially cylindrical shape through which an overtube or medical tool may extend, the inflatable balloon 4712 has a semi-annular shape intended to be disposed on the exterior of the overtube 4702 of the overtube assembly 4700. Accordingly, the inflatable balloon 4712 includes an inner concave surface 5308 shaped to receive the overtube 4702. In certain implementations, the balloon 4712 is formed to have the inner concave surface 5308 in others however, the balloon 4712 may have an oblong or "D"-shaped cross-section and the concave surface 5308 may be formed by indenting the inner surface of the balloon prior to application onto the overtube 4702.

The inflatable balloon 4712 may further include a textured outer convex surface 5310. As illustrated, the texturing 5312 on the outer convex surface 5310 includes longitudinally extending rows of frustoconical protrusions; however, texturing of the outer convex surface 5310 may generally conform to any texturing discussed herein.

To facilitate assembly, the inflatable balloon 4712 may be formed with one or more open ends, such as open end 5314. During assembly, the open end 5314 permits access to the internal volume of the balloon 4712 to facilitate coupling of the balloon 4712 to the overtube 4702. For example, the balloon 4712 may be positioned onto the overtube 4702 and then each of the balloon 4712 and the overtube 4702 may be simultaneously pierced from within the balloon 4712 to form the overtube port 4717 and the balloon port 4728 previously discussed in the context of FIG. 51. Similarly, the open end 5314 of the balloon 4712 may be used to enable insertion of a conduit 4734, as illustrated in Detail C' of FIG. 51. As illustrated in the transition between FIGS. 55 and 56 (each of which is an isometric view of the overtube assembly 4700, the open end 5314 is ultimately closed (e.g., using an adhesive, plastic welding, or similar process), thereby sealing the inflatable balloon 4712.

In certain implementations of the present disclosure, the tubular body of the overtube may include cutouts or similar voids to increase the flexibility of the overtube. In certain implementations, such voids may be evenly distributed along and about the length of the overtube to provide relatively uniform increased flexibility along the length of the tubular body. Alternatively, such voids may be disposed at specific locations (e.g., at particular longitudinal locations and/or on a particular side of the tubular body) to locally vary the flexibility of the tubular body. In certain implementations, localized thinning, scoring, grooves, etc. may similarly be used to vary the flexibility of the tubular body along its length.

In implementations in which voids or similar flexibility modifying features are disposed along the length of the tubular body, the tubular body may be wrapped, at least in part, in a low-friction sheath. For example, subsequent to coupling the tubular assembly to an endoscope or similar elongate tool, tape, a wrap, or similar layer formed of a low friction material (e.g., silicone) may be applied to the overtube of the overtube assembly to reduce interaction between the tubular body (and, in particular, any edges of the voids or flexibility modifying features) and the physiological lumen within which the tool is being used.

Figure 57:
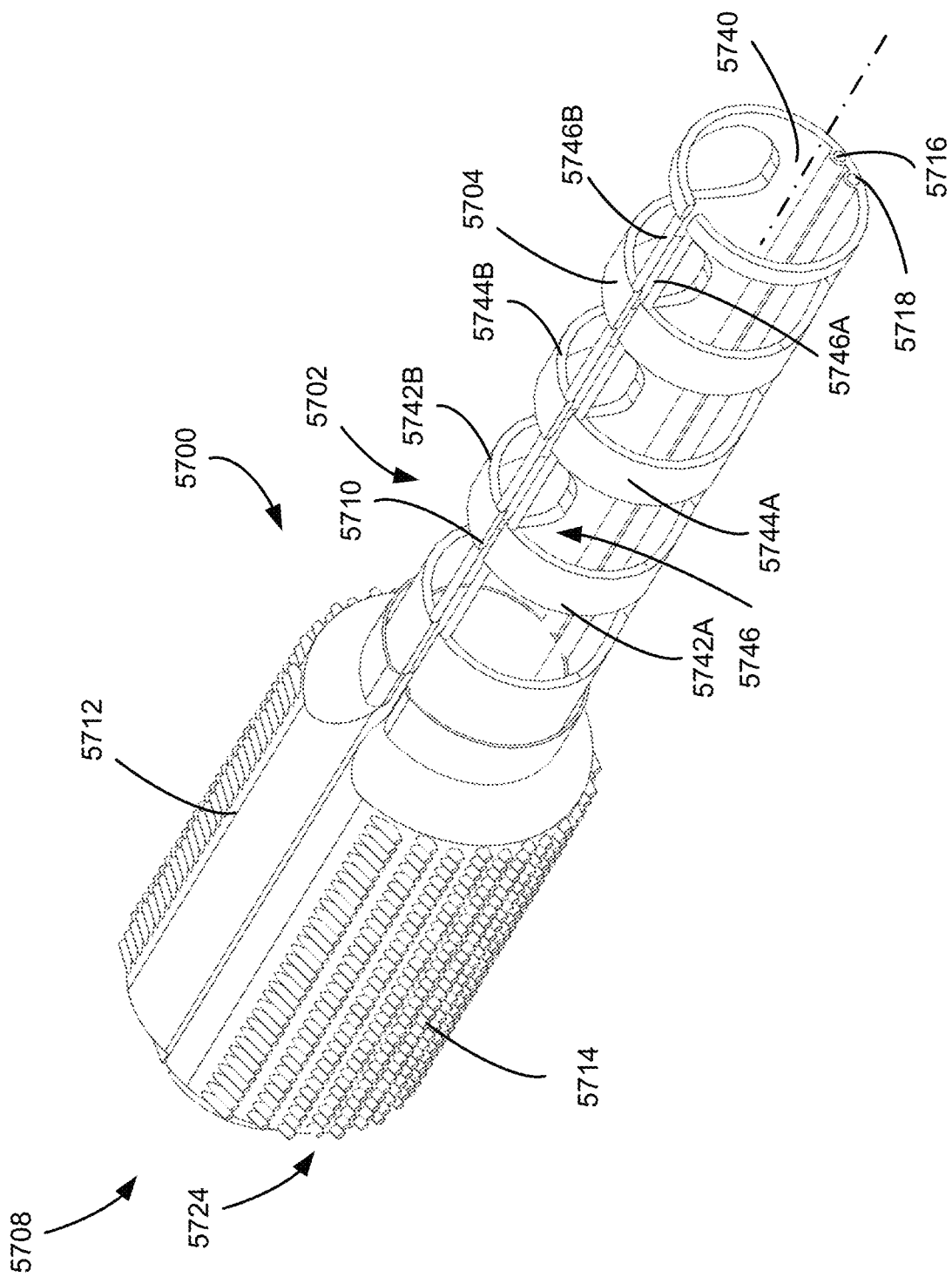
FIG. 57 is an isometric view of a distal portion of an overtube assembly according to the present disclosure.
Figure 58:
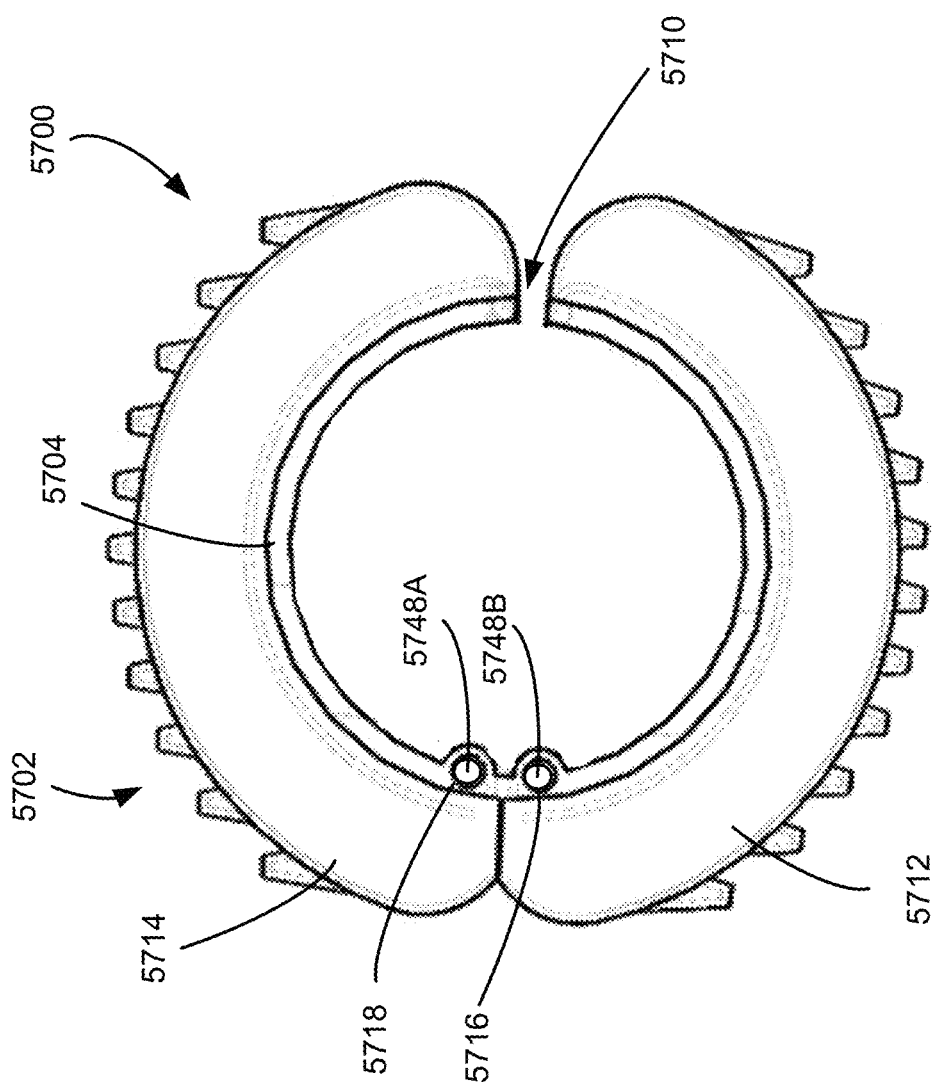
FIG. 58 is a distal end view of the overtube assembly of FIG. 57.

For example, FIGS. 57 and 58 are an isometric view and a distal end view, respectively, of an alternative overtube assembly 5700 in accordance with the present disclosure and which includes flexibility modifying features as discussed above. More specifically, FIG. 57 illustrates a distal portion of the overtube assembly 5700. The overtube assembly 5700 includes an overtube 5702 having a flexible tubular body 5704 that extends from a proximal end (not shown) of the overtube 5702 to a distal end 5708 of the overtube 5702. Similar to the tubular body 4704 of the overtube assembly 4700, the tubular body 5704 defines a split 4710 extending from its proximal end to the distal end 4708 to facilitate coupling of the overtube assembly 5700 to an endoscope or similar elongate tool. The overtube assembly 5700 further includes one or more inflatable balloons, such as inflatable balloon 5712 and 5714, which are illustrated as being disposed on opposite sides of the tubular body 5704 on a distal portion 5724 of the tubular body 5704.

As illustrated in FIG. 57, the tubular body 5704 of the overtube assembly 5700 includes a solid/continuous portion, referred to herein as a strip or backbone 5740, from which multiple ribs or bands (e.g., bands 5742A, 5742B and bands 5744A, 5744B) extend. As a result, voids or gaps (e.g., gap 5746 between band 5742A and 5744A) are formed between adjacent bands. As a result of the gaps, the overall flexibility of the tubular body 5704 is significantly increased as compared to the flexibility of a substantially continuous tubular body, such as the tubular body 4704 of the overtube assembly 4700 of FIG. 47.

In certain implementations, the tubular body 5704 may further include a pair of flexible rods 5746A, 5746B to which the bands are coupled and that extend along opposite sides of the split 5710. For example, each of bands 5742A and 5744A are coupled to rod 5746A while each of bands 5742B and 5744B are coupled to rod 5746B. Among other things, the rods 5746A, 5746B provide additional structural stability for the tubular body 5704.

While illustrated in FIG. 57 as being paired along the length of the tubular body 5704, implementations of the present disclosure may include bands that are offset relative to each other.

Air may be provided to or removed from each of the inflatable balloons 5712, 5714 via respective air supply lumens 5716, 5718 extending along the tubular body 5704. As shown in FIG. 57, the air supply lumens 5716, 5718 of the example overtube assembly 5700 extend inwardly from the backbone 5740, opposite the split 5710. In certain implementations, the air supply lumens 5716, 5718 may be integrally formed with the backbone 5740. Alternatively, the air supply lumens 5716, 5718 may be separately formed tubules that are coupled to the backbone 5740 using any suitable method. As yet another alternative, the air supply lumens 5716, 5718 may be defined by and extend through the rods 5746A, 5746B.

Other than their placement opposite the split 5710, the air supply lumens 5716, 5718 are structurally and functionally similar to those included in the overtube assembly 4700 discussed above. More specifically, during assembly, the air supply lumens 5716, 5718 are made to be in communication with internal volumes of the inflatable balloons 5712, 5714 (e.g., by using ports defined in the tubular body and balloons and/or suitable conduits extending between the internal volume of the balloons and the air supply lumens). A proximal end (not shown) of the air supply lumens 5716, 5718 is also configured to be coupled to a pump or other air supply device (not shown) to supply air to and/or remove air from the internal volumes of the inflatable balloons 5712, 5714 via the air supply lumens 5716, 5718. In certain implementations, the air supply lumens 5716, 5718 may extend along the full length of the tubular body 5704. In such implementations, the distal ends of the air supply lumens 5716, 5718 may also be capped, plugged, or otherwise sealed (e.g., using plugs 5748A, 5748B, shown in FIG. 58).

In alternative implementations of the backbone-style overtube, the rods 5746A, 5746B may be omitted and the tubular body 5704 may be configured similar to a comb-style binding spine. For example, the bands may extend from the backbone 5740, extend circumferentially about the tubular body 5704, and come into contact with either the internal or external surface of the backbone 5740. In such implementations, the bands may extend from only one side of the backbone 5740 or may extend from both sides of the backbone 5740 in an interdigitated manner. In at least some implementations, the bands may be configured to extend circumferentially past the backbone.

Figure 59:
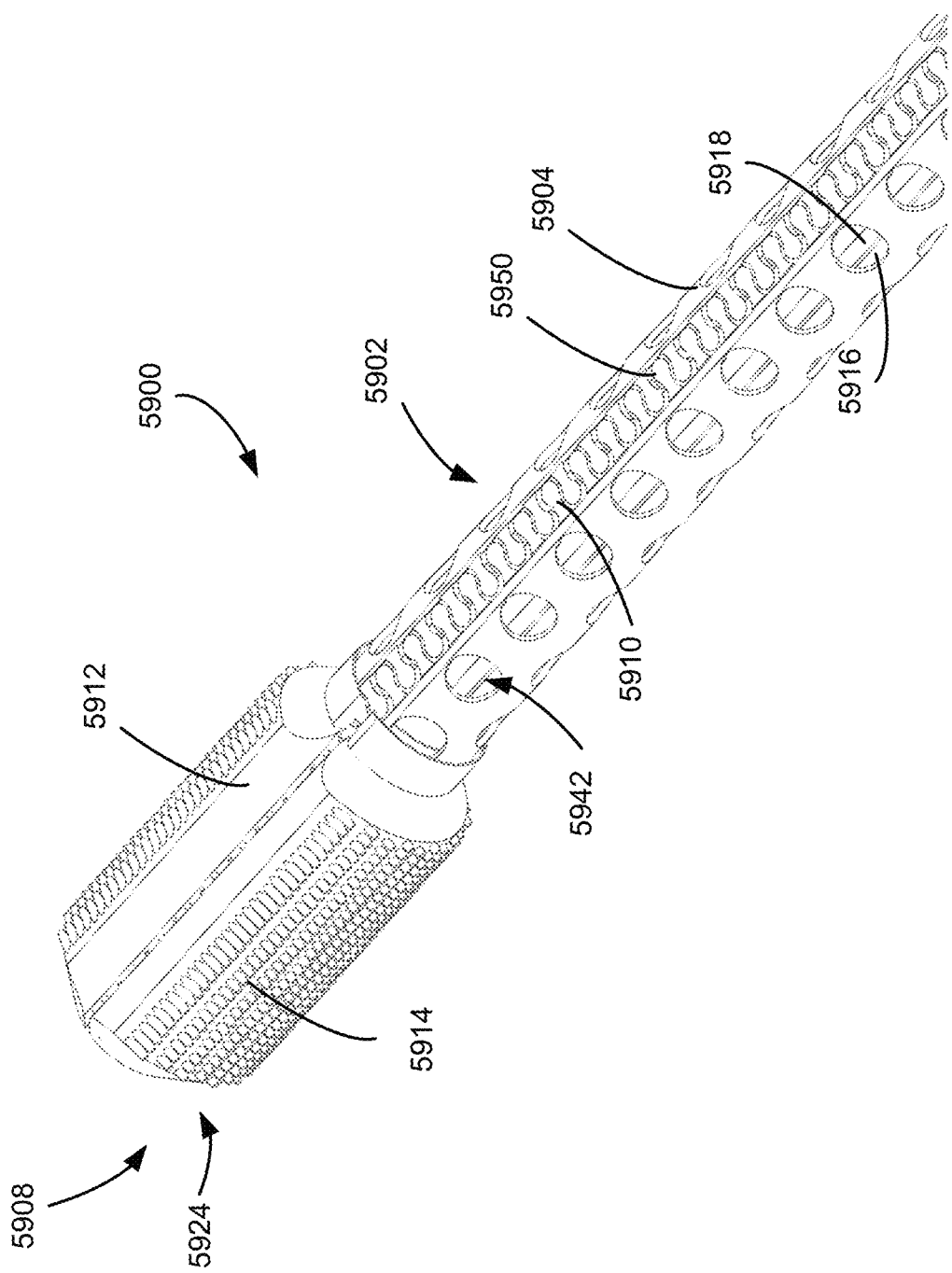
FIG. 59 is an isometric view of another overtube assembly according to the present disclosure.
Figure 60:
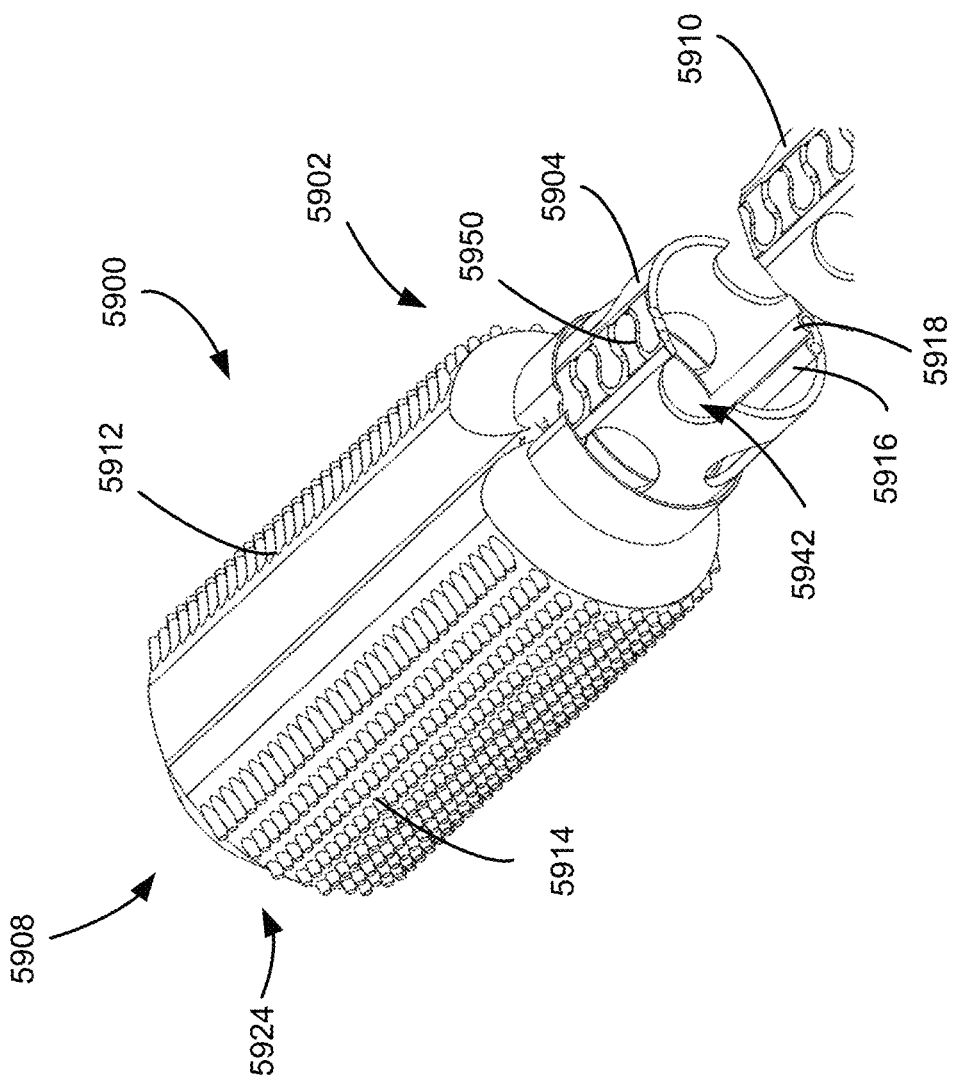
FIG. 60 is a detailed isometric view of a distal portion of the overtube assembly of FIG. 59.

FIG. 59 is a partial isometric view of yet another overtube assembly 5900 in accordance with the present disclosure. FIG. 60 is a more detailed isometric view of a distal end of the overtube assembly 5900. The overtube assembly 5900 includes an overtube 5902 having a flexible tubular body 5904 that extends from a proximal end (not shown) of the overtube 5902 to a distal end 5908 of the overtube 5902. Similar to the tubular bodies of previously discussed implementations, the tubular body 5904 defines a split 5910 extending from its proximal end to the distal end 5908 to facilitate coupling of the overtube assembly 5900 to an endoscope or similar elongate tool. The split 5910 is shown in a closed configuration using a zipper-style closure 5950, which is discussed below in further detail. The overtube assembly 5900 further includes one or more inflatable balloons, such as inflatable balloon 5912 and 5914, which are illustrated as being disposed on opposite sides of the tubular body 5904 on a distal portion 5924 of the tubular body 5904.

Similar to the tubular body 5704 of the overtube assembly 5700, the tubular body 5904 includes features configured to modify the flexibility of the tubular body 5904 as compared to a substantially solid tubular body. In particular, the tubular body 5904 defines a plurality of voids or holes (e.g., void 5942) distributed along its length and around its circumference. Similar to the gaps between the bands of the tubular body 5704 illustrated in FIG. 57, the voids or holes of the tubular body 5904 similarly reduce the rigidity of the tubular body 5904.

Although illustrated in FIGS. 59 and 60 as being uniformly distributed along the tubular body 5904, such holes may instead be concentrated at particular locations to locally modify the flexibility of the tubular body 5704. Moreover, implementations of the present disclosure are not limited to holes or voids or any particular shape or size.

Air may be provided to or removed from each of the inflatable balloons 5912, 5914 via respective air supply lumens 5916, 5918. Similar to the air supply lumens 5716, 5718 of the overtube assembly 5700, the air supply lumens 5916, 5918 of the overtube assembly 5900 extend inwardly from a side of the tubular body 5904 opposite the split 5910, however, they may be disposed or otherwise routed in any suitable manner along the tubular body 5904 provided they enable air to be supplied/removed from the inflatable balloons 5912, 5914.

As noted above, the overtube assembly 5900 includes a closure mechanism and, in particular, a zipper-style closure 5950 to facilitate closing the split 5910. Although not necessary in all implementations of the present disclosure, closure mechanisms, such as the zipper-style closure 5950, can provide additional reinforcement and retention of the overtube assembly on the endoscope or other elongate tool in addition to any biasing of the tubular body into a closed shape resulting from its shape and material.

Mechanical closures in accordance with the present disclosure may include closures that are integrated into the tubular body and extend along at least a portion of the split. The zipper-style closure 5950, for example, is coupled to or otherwise integrated with the tubular body 5904 and extends along a substantial portion of the split 5910. Another example of an integrated closure is provided in FIG. 45. As discussed above, the overtube 4500 illustrated in FIG. 45 overlapping portions 4506A, 4506B that form an interface. The overlapping portions of the overtube further include corresponding ridges 4510 and grooves 4512 shaped to positively engage each other when the overtube 4500 is disposed on an endoscope or similar tool.

In other implementations, the tubular body of the overtube assembly may include interlocking tabs, snaps, clasps, or other similar closure mechanisms disposed along the length of the split.

Alternatively, closures may be separate components that are disposed along the tubular body and that provide retentive force onto the tubular body. For example, one or more of clips, bands, split rings, or similar elements may be disposed along the length of the tubular body after insertion of an elongate tool into the tubular body to provide additional retention of the tubular body onto the tool.

Figure 61:
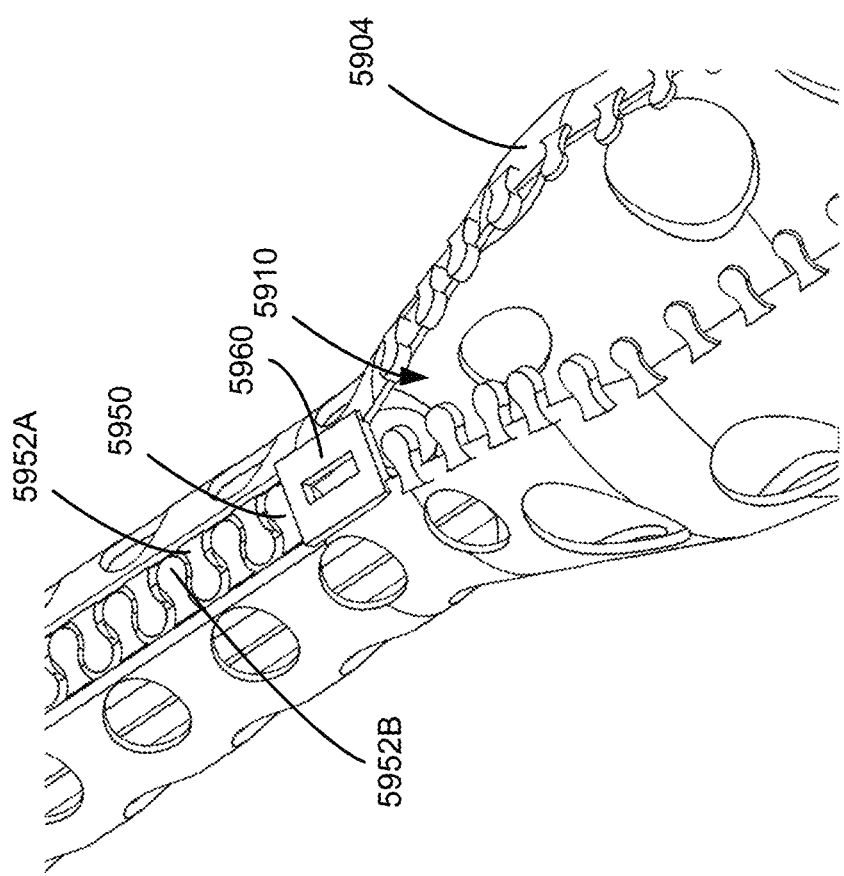
FIG. 61 is a detailed view of a portion of the overtube assembly of FIG. 59 illustrating a closure mechanism.

In certain implementations, the closures mechanisms may require additional tools or components to facilitate their use. For example, FIG. 61 illustrates a pull tab tool 5960 that may be used to open and close the zipper-style closure 5950 of the overtube assembly 5900. Similar to a conventional zipper, when the zipper-style closure 5950 is open/disengaged, distal ends of each half 5952A, 5952B of the zipper-style closure 5950 may be inserted into a proximal end of the pull tab tool 5960. The pull tab tool 5960 may then be translated proximally along the zipper-style closure 5950, engaging the interdigitating teeth of the closure halves 5952A, 5952B. In at least some implementations, the zipper-style closure 5950 may be configured such that the pull tab tool 5960 may be disengaged after closing the zipper-style closure 5950. For example, the pull tab tool 5960 may be disengaged by continuing to slide the pull tab tool 5960 beyond a proximal extent of the zipper-style closure 5950. It should also be noted that in alternative implementations, the zipper-style closure 5950 may be configured such that to close the zipper-style closure 5950, proximal ends of the halves 5952A, 5952B may be inserted into a distal end of the pull tab tool 5960 and the pull tab tool 5960 may be translated distally.

Figure 62:
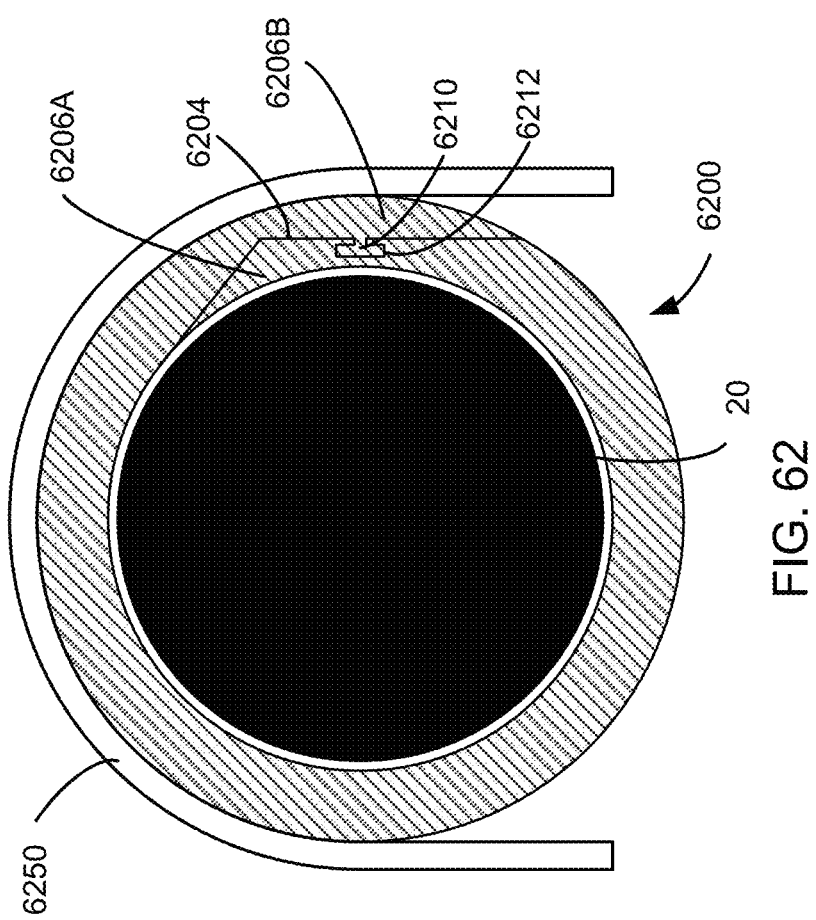
FIG. 62 is a cross-sectional view of a split overtube assembly including a closure tool.

FIG. 62 is a cross-sectional view of another overtube 6200 and corresponding closure tool 6250. As illustrated, the overtube 6200 is disposed on an endoscope 20. As illustrated and similar to the overtubes 4400 of FIG. 44 and 4500 of FIG. 45, the overtube 6200 includes a split 6204 formed between overlapping portions of the overtube 6200. More specifically, when disposed about the endoscope 20 a first portion 6206A of the overtube 6200 is disposed inwardly of a second portion 6206B of the overtube 6200, forming an interface between the inward surface of the first portion 6206A and the outward surface of the second portion 6206B. In addition to the overlap at the interface, the first portion 6206A and the second portion 6206B may include mating or engaging structures. In particular, the first portion 6206A includes a T-shaped ridge 6210 shaped to be received by a corresponding T-shaped groove 6212 defined in the second portion 6206B.

In certain implementations, engagement of mating structures, such as those illustrated in FIGS. 45 and 62 may be facilitated by a tool that may be disposed on, applied to, or moved along the overtube. Such tools may be particularly beneficial in implementation in which closing the split by engaging the mating structures strictly may be For example, the tool 6250 illustrated in FIG. 62 is substantially rigid and shaped to be fit over and slid longitudinally along the length of the overtube. As the tool is slid along the overtube, it forces the ridge 6210 into the groove 6212, thereby closing the split 6204 of the overtube. More generally, however, the tool 6250 may be any device suitable to apply pressure onto the overtube 6200 to engage the mating structures of the overtube.

Figure 63:
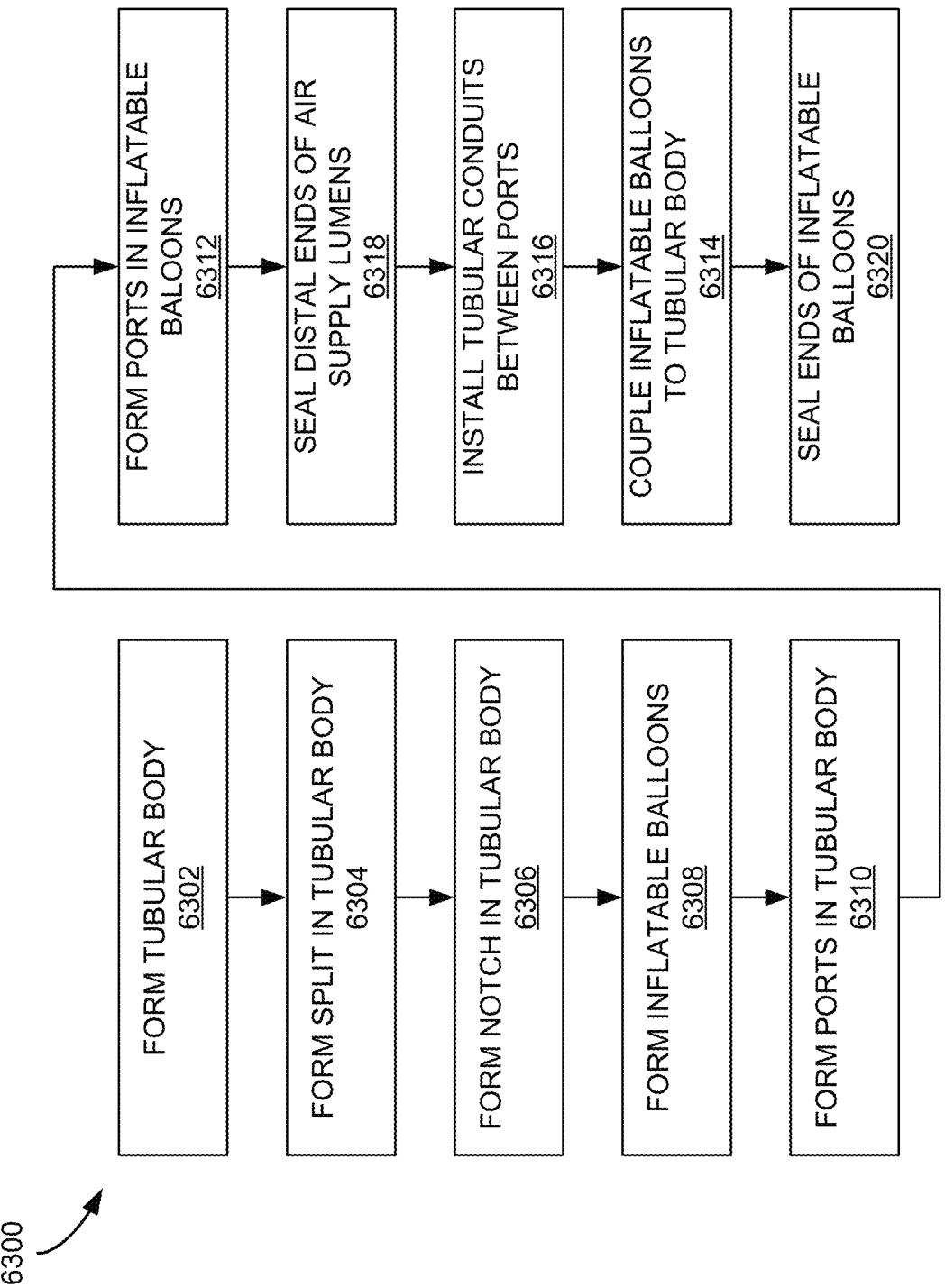
FIG. 63 is a flow chart describing an example method of manufacturing an overtube assembly, such as the overtube assembly of FIG. 47.

FIG. 63 is a method 6300 for manufacturing an overtube assembly, such as the overtube assembly 4700 of FIGS. 50-53. For explanatory purposes only, reference is made to the overtube assembly 4700 and its components. However, implementations of the method 6300 are not limited to the overtube assembly 4700 as illustrated in FIGS. 50-53.

In general, the method of manufacturing includes forming each of the tubular body 4704 of the overtube 4702 and each of the inflatable balloons 4712, 4714. Forming the tubular body 4704 generally includes forming the split 4710 extending along the tubular body 4704. The inflatable balloons 4712, 4714 are then coupled to the tubular body 4704 such that the internal volumes of the inflatable balloons 4712, 4714 are in communication with the air supply lumens 4716, 4718 of the overtube 4702. Accordingly, in certain implementations, manufacturing the overtube assembly 4700 may further include forming ports in the balloons 4712, 4714 and/or the tubular body 4704 and disposing the inflatable balloons 4712, 4714 onto the tubular body 4704 such that each of the ports of the tubular body 4704 are in communication with a respective port of an inflatable balloon 4712, 4714.

In light of the foregoing, operation 6302 includes forming the tubular body 4704. Although any suitable process may be used to form the tubular body 4704, in at least one implementation of the present disclosure, the tubular body 4704 is formed using an extrusion process. In such implementations, the tubular body 4704 may be formed using an extrusion machine having a die shaped to form each of the tubular cavity 4726 and the air supply lumens 4716, 4718 of the tubular body 4704.

In at least certain implementations, the tubular body 4704 is formed from at least one of Nylon, PFA, PET, PTFE, FEP, HDPE, and TPPE. The material of the tubular body 4704 may also include additives to reduce surface friction of the tubular body 4704. For example, in one specific implementation, the tubular body may be formed from Hytrel Thermoplastic Polyester Elastomer with Everglide. In certain implementations, the tubular body 4704 may have a wall thickness from and including about 0.25 mm to and including about 1.0 mm. Although not limited to such implementations, thinner walled tubular bodies according to the present disclosure may generally be formed from a more rigid polymer than thicker-walled tubular bodies such that the thin-walled tubular bodies have sufficient rigidity to advance within the physiological lumen of the patient (e.g., the GI tract). In one specific implementation, the wall thickness of the tubular body 4704 may be about 0.75 mm. Although not limited to specific dimensions, in at least certain implementations, the air supply lumens 4716, 4718 may have a diameter of approximately 0.8 mm and a wall thickness of approximately 0.33 mm. In general, however, this air supply lumen diameter and wall may be made as small and thin as possible in order to minimize the size of the tubular body and, as a result, minimize the volume invaded within the physiological lumen. Similarly, other features of the tubular body may be formed to be as thin and small as possible as thinner and smaller features generally result in the tubular body being more flexible and better able to move through any turns of the physiological lumen within which it is deployed. Nevertheless, for certain materials (e.g., silastic polymers), minimum wall thickness and other dimensions may be limited by manufacturing. Also, if the lumen is intended to deliver/remove fluids other than air, the lumen diameter may need to be larger compared to air to account for the increased viscosity of the fluid.

Formation of the tubular body may include surface treating a portion of either the interior or exterior surface of the tubular body 4704 to provide increased friction. For example and as discussed in the context of FIGS. 41 and 42, the internal surface of overtubes in accordance with the present disclosure may be coated or have integrally formed texturing at selective locations to increase friction with the medical tool disposed within the overtube. Similarly, and as discussed below in the context of FIGS. 59-66, the exterior surface of devices in accordance with the present disclosure, including the overtube 4702 of the overtube assembly 4700, may similarly have exterior surfaces adapted to increase friction with the interior wall of a physiological lumen. For example, such exterior surfaces may be coated or include integrally formed texturing similar to the interior surfaces previously noted.

In operation 6304, the split 4710 of the tubular body 4704 is formed. In at least certain implementations, formation of the split 4710 occurs during the extrusion process, e.g., by using an extrusion die where the wall of the tubular body 4704 is not continuous. Accordingly, the process of forming the tubular body 4704 (e.g., operation 6302) and forming the split 4710 along the tubular body 4704 (e.g., operation 6304) may occur simultaneously.

Alternatively, the wall 4730 of the tubular body 4704 may be extruded or otherwise formed to have a continuous circumference. In such cases, an additional cutting/splitting process may be required. In certain cases, splitting of the tubular body 4704 may be achieved using a knife or similar cutting tool disposed adjacent the extrusion machine such that the tubular body 4704 is split as it is extruded. Alternatively, a knife or similar cutting implement may be used to split the tubular body 4704 after the tubular body 4704 has been fully extruded. In at least certain implementations, the tubular body 4704 may be formed in operation 6302 with a seam or similar thin-walled portion to guide splitting. In such implementations, the seam may be designed such that splitting of the tubular body 4704 may be achieved by hand, e.g., by pulling apart the tubular body 4704 at the seam.

In operation 6306, a notch 4750 is formed in the distal end 4708 of the tubular body 4704. As previously discussed in the context of FIG. 52, a notch 4750 may be formed in the distal end 4708 of the tubular body 4704 to facilitate insertion of an endoscope 20 or similar elongate medical tube into the overtube 4702. More specifically, when disposing the overtube assembly 4700 on an endoscope 20, the endoscope 20 is first inserted into the distal extent of the notch 4750. Formation of the notch 4750 may include, among other things, trimming or otherwise cutting away the tubular body 4704 either by hand or using an automated machine.

Operations 6302-6306 generally correspond to manufacturing and forming of the tubular body 4704. As discussed above, other implementations of the present disclosure may include additional features and structures not included in the overtube assembly 4700. To the extent such features are not specifically included in the method 6300, formation of such features are nevertheless contemplated to be included in manufacturing methods according to the present disclosure. For example and among other things, manufacturing methods according to the present disclosure may include operations directed to modifying the flexibility of the tubular body. For example and referring to the overtube assembly 5700 of FIG. 57, manufacturing methods according to the present disclosure may include may include forming the bands (e.g., bands 5742A, 5742B and bands 5744A, 5744B) (and, as result the gaps/voids between the bands) and coupling the bands to the rods 5746A, 5746B. As another example and referring to the overtube assembly 5900 of FIG. 59, forming the tubular body may include forming the voids (e.g. void 5942). Manufacturing methods according to the present disclosure may also include the formation or inclusion of additional features to the tubular body. For example and again referring to the overtube assembly 5900 of FIG. 59, manufacturing methods of the present disclosure may include adding a closure mechanism, such as the zipper-style closure 5950, to the tubular body.

In operation 6308, the balloons 4712, 4714 are formed. Non-limiting examples of balloon manufacturing methods are discussed above in the context of FIGS. 8 and 9. In general, however, forming the balloons 4712, 4714 generally includes molding or otherwise producing an initial shape of the balloons 4712, 4714. In certain implementations, the balloons 4712, 4714 may have integrally formed texturing, however, in other cases, texturing may be applied to the balloons 4712, 4714 after an initial molding process. To the extent the balloons 4712, 4714 are not produced having a shape that conforms to the overtube 4702, forming the balloons 4712, 4714 may further include manipulating or shaping the balloons 4712, 4714 to conform to the overtube 4702.

In operation 6310 ports are formed in the tubular body 4704. As described above, the overtube ports (e.g., overtube port 4717, illustrated in FIG. 51), are in communication with a respective one of the air supply lumens 4716, 4718. Forming each air overtube port generally includes forming a passage through the wall 4730 of the tubular body 4704 such that the passage extends from an exterior surface of the tubular body 4704 and terminates at one of the air supply lumens 4716, 4718. Accordingly, forming the overtube ports may include, among other things, cutting, puncturing, or similarly altering the tubular body 4704.

In operation 6312, balloon ports are formed in the inflatable balloons 4712, 4714. As previously discussed, each inflatable balloon generally includes a balloon port that enables air to be passed into or removed from an internal volume of the inflatable balloon, thereby inflating or deflating the balloon. Similar to the overtube ports, a balloon port for each inflatable balloon may be formed by cutting, puncturing or similarly altering the wall of the inflatable balloon.

In operation 6314 the inflatable balloons 4712, 4714 are coupled to tubular body 4704. Coupling of the inflatable balloons 4712, 4714 to the tubular body 4704 generally includes disposing the inflatable balloons 4712, 4714 onto the tubular body 4704 such each of the balloon ports of the inflatable balloons 4712, 4714 is in communication with one of the overtube ports of the tubular body 4704. The inflatable balloons 4712, 4714 may then be attached to the tubular body 4704, such as by using an adhesive, fusing the inflatable balloons 4712, 4714 to the tubular body 4704, or by any other suitable process.

In operation 6316, a tubular conduit 4734 is inserted through each pair of balloon ports and overtube ports to reinforce the pathway between the ports. In other implementations, the tubular conduit 4734 may be omitted.

Figure 56:
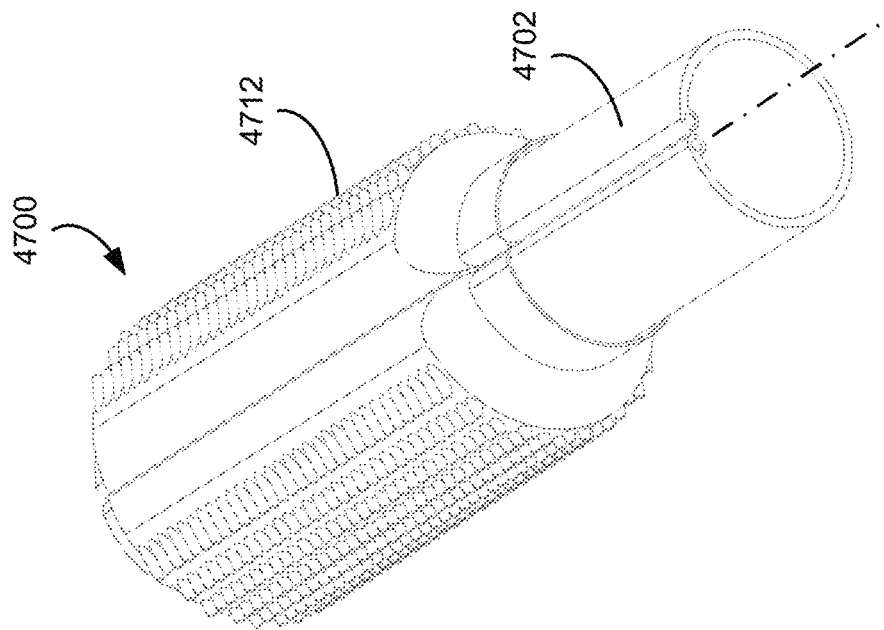
FIGS. 55 and 56 are isometric views of the distal portion of the split overtube assembly illustrating the inflatable balloons in an unsealed and sealed state, respectively.
Figure 55:
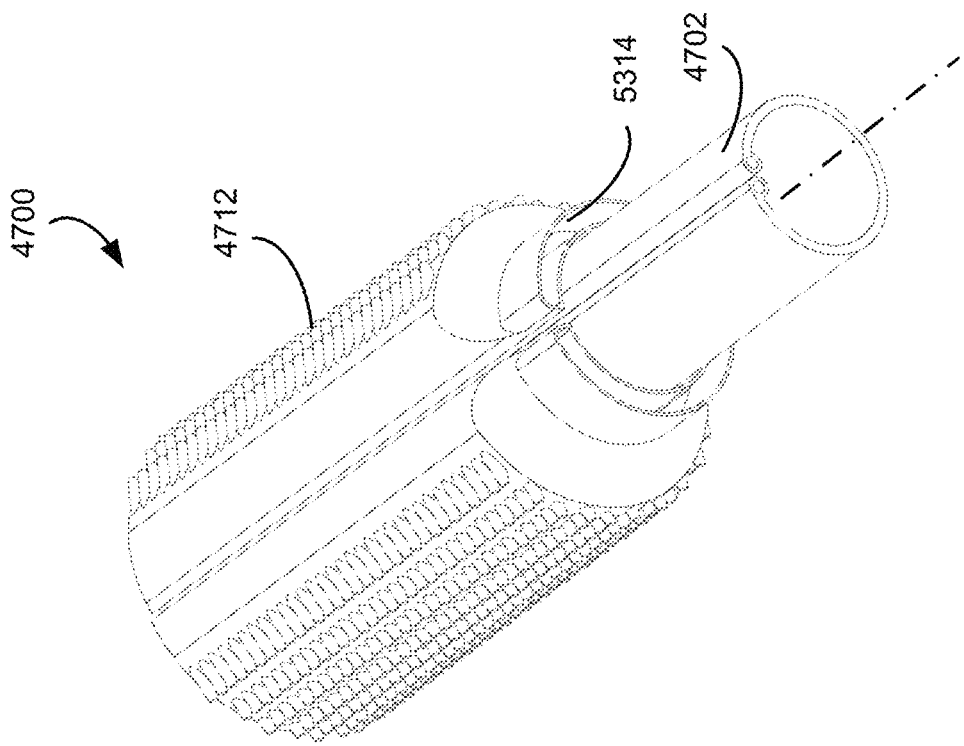

In certain implementations, the inflatable balloons 4712, 4714 may be coupled to the tubular body 4704 prior to formation of either of the balloon ports or overtube ports. For example, in certain implementations, the balloons 4712, 4714 may be coupled to the tubular body 4704 and the balloon and overtube ports may then be formed in a substantially simultaneous manner by cutting, puncturing, etc. the tubular body 4704 and the balloons 4712, 4714 after coupling. In other implementations, the step of inserting the tubular conduit 4734 may also occur In operation 6318 and if the air supply lumen extends along the full length of the overtube 4702, the distal end of the air supply lumens 4716, 4718 may be sealed. For example, caps or similar inserts may be disposed in the distal end of the air supply lumens. In other implementations, a filler or adhesive may be injected into the distal ends of the air supply lumens. Similarly and as illustrated in FIGS. 55-56, the balloons 4712, 4714 may be sealed (operation 6320).

The forgoing example implementations are intended merely to illustrate various concepts of split overtubes in accordance with the present disclosure and should be regarded as non-limiting.

Expandable Overtubes

In certain use cases and with certain patients, only relatively small endoscopes may be advanced through a given physiological lumen. In other words, a gastroenterologist or similar physician or technician may be prevented from inserting larger diameter scopes and advancing such scopes as far as needed to perform a procedure. One specific example is with patients with altered anatomy resulting from bariatric or other similar procedures.

In other cases, a side-facing endoscope may ultimately be needed for the procedure, but advancing a larger, side-facing scope may be challenging due to the patient's anatomy, among other things. In such cases, the ability to use a forward facing endoscope to reach the desired location is valuable only if an overtube can then be placed so that the overtube may be used to guide a larger scope (e.g., a side facing scope) to the desired location.

To address the foregoing issues, among others, the current disclosure includes an expandable overtube. In a first configuration, such as may be used during insertion of first, smaller endoscope (or similar tool) the expandable overtube is compressed to a first, smaller diameter. Upon removal of the first endoscope, a second, larger endoscope (or similar tool) may be inserted into the overtube which expands to accommodate the larger tool. In certain implementations, for example, in the first configuration the overtube may have an inner diameter of approximately 10 mm but may be configured to expand to 15 mm or more in response to insertion of a larger tool. To facilitate the forgoing expansion and contraction, the overtube may include an embedded mesh that provides structural rigidity to the overtube in each of the compressed and expanded configurations.

FIGS. 64A-64C illustrate an example procedure using an expandable overtube in accordance with the present disclosure. Referring first to FIG. 64A, a physiological lumen 30 is shown within which an endoscope assembly 6400 is disposed, the endoscope assembly 6400 including a first endoscope 6402 disposed within an expandable overtube 6404.

The first endoscope 6402 may have a first diameter for use in intubating the patient with the expandable overtube 6404. Once intubated, the first endoscope 6402 may be removed and a second endoscope or tool 6406 may be inserted into the overtube 6404, as illustrated in FIG. 64B. As the second endoscope or tool 6406 is advanced through the overtube 6404, an outward force is applied to the overtube 6404 causing it to expand. In certain implementations, such expansion may be facilitate, in part, by an embedded mesh within the overtube 6404 configured to retain its shape when expanded outwardly.

As shown in FIG. 64C, the second endoscope or tool 6406 may be advanced to extend beyond the now-expanded overtube 6404 to the original position of the first endoscope 6402 illustrated in FIG. 64A.

Any surface of the overtube 6404 may include texturing in accordance with the present disclosure. For example and without limitation, the outer surface of the overtube 6404 may include texturing configured to facilitate frictional engagement of the overtube 6404 with the inner surface of the physiological lumen within which the overtube 6404 is disposed. Such frictional engagement may prevent slippage or shifting of the overtube 6404 during expansion of the overtube 6404 in response to insertion of the second, larger tool 6406 into the overtube 6404. In implementations in which the overtube 6404 is textured, such texturing may be applied to substantially the entire length of the overtube 6404 or may be applied to one or more segments of the overtube 6404. In certain implementations, the texturing may be configured to have a first engagement level when the overtube 6404 is in a first (e.g., the compressed) configuration, but to have a second engagement level when the overtube is in a second (e.g., the expanded) configuration, the second engagement level resulting from a difference in strain applied to the textured portions of the overtube 6404.

The forgoing example implementations are intended merely to illustrate various concepts and applications of an expandable overtube in accordance with the present disclosure and should be regarded as non-limiting.

Textured Endoscopic Tools

Endoscopic procedures may include a biopsy or similar removal of a portion of tissue. When a snare or a biopsy catheter is used, the location of the scope and the tissue of interest may be located such that holding the snare steady relative to the tissue and the scope may be extremely challenging, particularly because the snare/biopsy catheter is generally unsupported within the physiological lumen within which the biopsy is to be taken.

To address the foregoing issues, among others, textured endoscopic tools are provided herein. In one implementation, texturing is applied to a snare, biopsy forceps, or other endoscope gastroenterology tools. Such texturing may be used to frictionally engage or adhere the tool to an inner wall of a physiological lumen and to help steady the tool relative to the tissue being removed. In certain implementations, texturing is disposed on the snare, biopsy tool, etc., itself. Alternatively or in addition to texturing of the tool itself, texturing may also be applied to a catheter through which the tool is delivered. In the latter case, the catheter adheres to the wall of the physiological lumen and is steadied by such adherence.

Texturing on the tool and/or catheter may also be used to pull tissue (e.g., a polyp or the wall of the physiological lumen) to facilitate tissue removal or to improve a physician's view of the physiological lumen. Notably, such tissue manipulation relies on relatively minimal engagement with the tissue, particularly when compared to conventional approaches in which a snare or similar tool is used to grasp the tissue.

Figure 65:
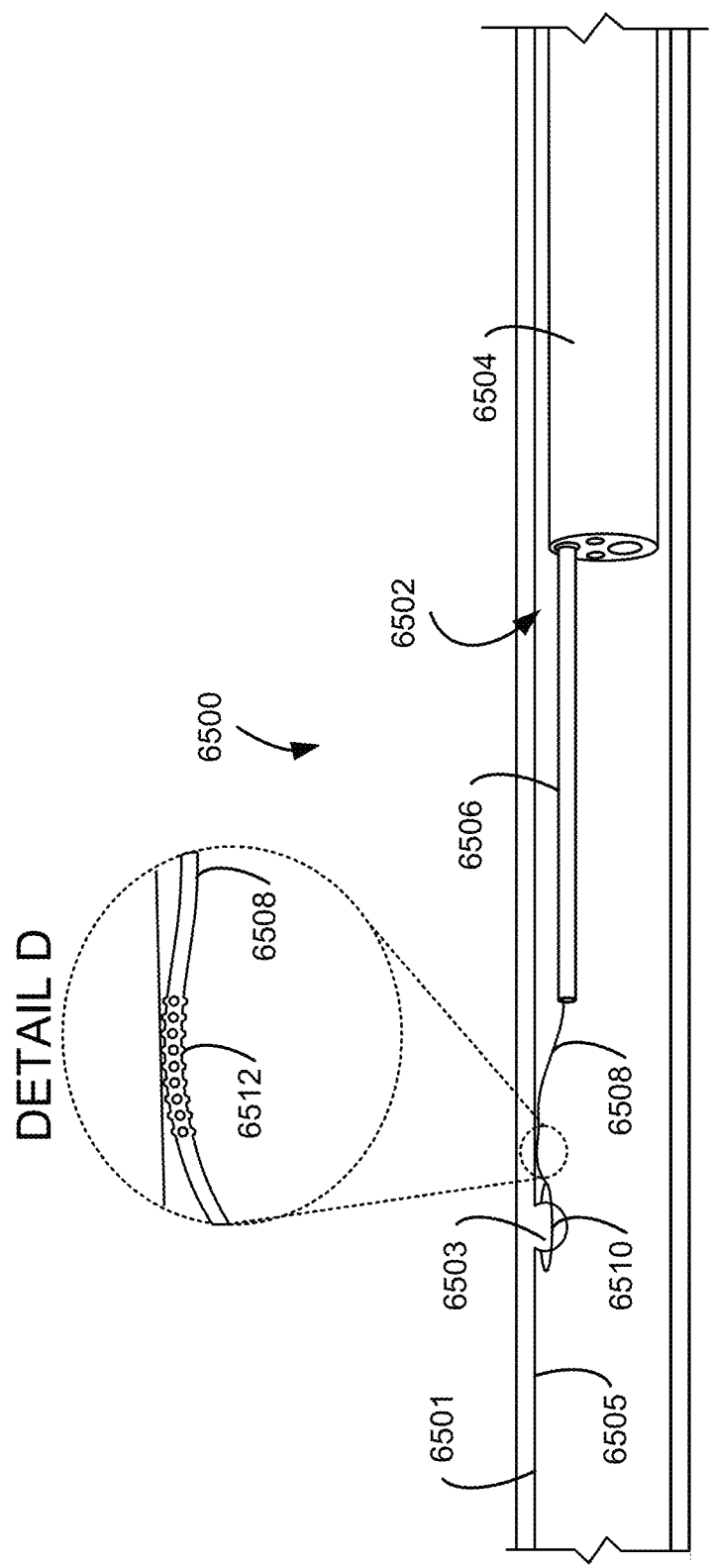
FIG. 65 is a schematic illustration of an endoscope disposed within a physiological lumen, the endoscope including a textured endoscopic tool.

FIG. 65 is a schematic illustration of an operational environment 6500 including a physiological lumen 6501 in which an endoscopic tool 6502 is disposed. For purposes of the current example, the physiological lumen 6501 is assumed to include a polyp 6503 which is to be removed; however, it should be appreciated that implementations of the current disclosure are not limited to such applications.

As illustrated the endoscopic tool 6502 includes an endoscope body 6504 from which a catheter 6506 may be extended. The endoscopic tool 6502 further includes a snare 6508 disposed within and extending from the catheter 6506. As illustrated, the snare 6508 includes a loop 6510 which may be used to encircle and capture the polyp 6503 for subsequent removal. The snare 6508 of FIG. 65 is provided merely as a non-limiting example of an endoscopic tool. It should be understood that the present disclosure is equally applicable to other tools including, without limitation, biopsy forceps, brushes, rods, guidewires, or any other tool that may be delivered via the endoscopic tool 6502 for any purpose.

As illustrated in Detail D, at least a portion of the snare 6508 includes texturing 6512 configured to increase frictional engagement between the snare 6508 and an inner wall 6505 of the physiological lumen 6501. In the specific example illustrated, the texturing 6512 is in the form of a series of protrusions extending from the snare 6508 and disposed proximal to the loop 6510; however, it should be understood that any suitable texturing applied at any location along an endoscopic tool may be used instead.

During use, a physician or technician may extend the snare 6508 from the catheter 6506 and position the snare 6508 such that the texturing 6512 contacts the inner wall 6505 of the physiological lumen 6501. Such contact between the texturing 6512 and the inner wall 6505 adheres the snare 6508 to the inner wall 6505, thereby stabilizing the snare 6508. In certain implementations, the physician or technician may advance, retract, or otherwise manipulate the snare 6508 once adhered to the inner wall 6505 to manipulate the physiological lumen (e.g., to improve visibility of an area of interest or to move tissue to make biopsy or tissue removal easier).

Figure 66:
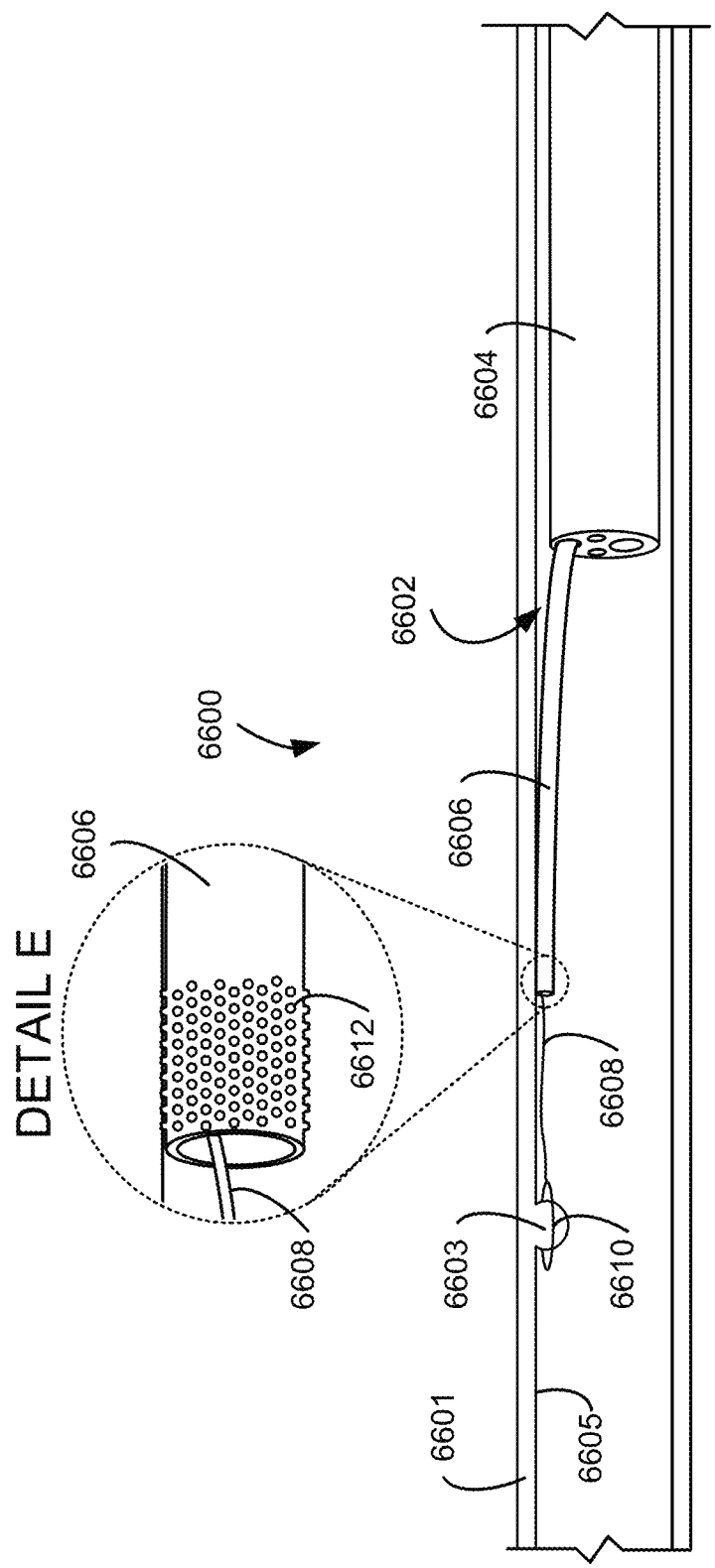
FIG. 66 is a schematic illustration of an endoscope disposed within a physiological lumen, the endoscope including a textured catheter.

FIG. 66 is a schematic illustration of an operational environment 6600 including a physiological lumen 6601 in which an endoscopic tool 6602 is disposed. For purposes of the current example, the physiological lumen 6601 is assumed to include a polyp 6603 which is to be removed; however, it should be appreciated that implementations of the current disclosure are not limited to such applications.

As illustrated the endoscopic tool 6602 includes an endoscope body 6604 from which a catheter 6606 may be extended. The endoscopic tool 6602 further includes a snare 6608 disposed within and extending from the catheter 6606. As illustrated, the snare 6608 includes a loop 6610 which may be used to encircle and capture the polyp 6603 for subsequent removal. Similar to the previous discussion, the snare 6608 is provided merely as a non-limiting example of an endoscopic tool.

As illustrated in Detail E, at least a portion of the catheter 6606 includes texturing 6612 configured to increase frictional engagement between the catheter 6606 and an inner wall 6605 of the physiological lumen 6601. In the specific example illustrated, the texturing 6612 is in the form of a series of protrusions extending from a distal portion of the catheter 6606; however, it should be understood that any suitable texturing applied at any location along the catheter 6606 may be used instead.

During use, a physician or technician may extend the catheter 6606 from the endoscopic tool 6602 and position the catheter 6606 such that the texturing 6612 contacts the inner wall 6605 of the physiological lumen 6601. Such contact between the texturing 6612 and the inner wall 6605 adheres the catheter 6606 to the inner wall 6605, thereby stabilizing the catheter 6606. The snare 6608 may then be advanced, retracted, or otherwise manipulated relative to the catheter 6606 to perform a given procedure.

The foregoing implementations are intended merely as examples and, as a result, should be viewed as non-limiting. More generally, the present disclosure is directed to catheters and endoscopic tools including texturing adapted to adhere the catheter and/or tool to tissue. In certain implementations, the texturing may be in accordance with specific examples of texturing discussed herein; however, implementations of the present disclosure are not necessarily limited to such specific examples. Moreover, texturing may be applied to the tool/catheter using any suitable technique. For example and without limitation, texturing may be integrally formed on the tool/catheter, may be applied as an outer layer or coating, or may be formed onto the tool/catheter (e.g., by overmolding or spray deposition).

Textured Stents

In yet another aspect of the present disclosure, textured stents are provided that improve anchoring of such stents, reducing potential for migration and additional interventions associated with repositioning or otherwise adjusting a stent.

In one specific implementation, a stent is provided for use in ducts, such as the biliary and pancreatic duct. In biliary and pancreatic duct applications, stents may be temporarily or permanently anchored to force open the duct to facilitate proper drainage into the gastrointestinal tract. For a variety of reasons, biliary and pancreatic ducts can become inflamed and be forced shut due to such inflammation. Accordingly, stents are commonly placed to allow the ducts to drain while the inflamed tissue is healed. However, as previously noted, stent migration can present a significant challenge.

Figure 67:
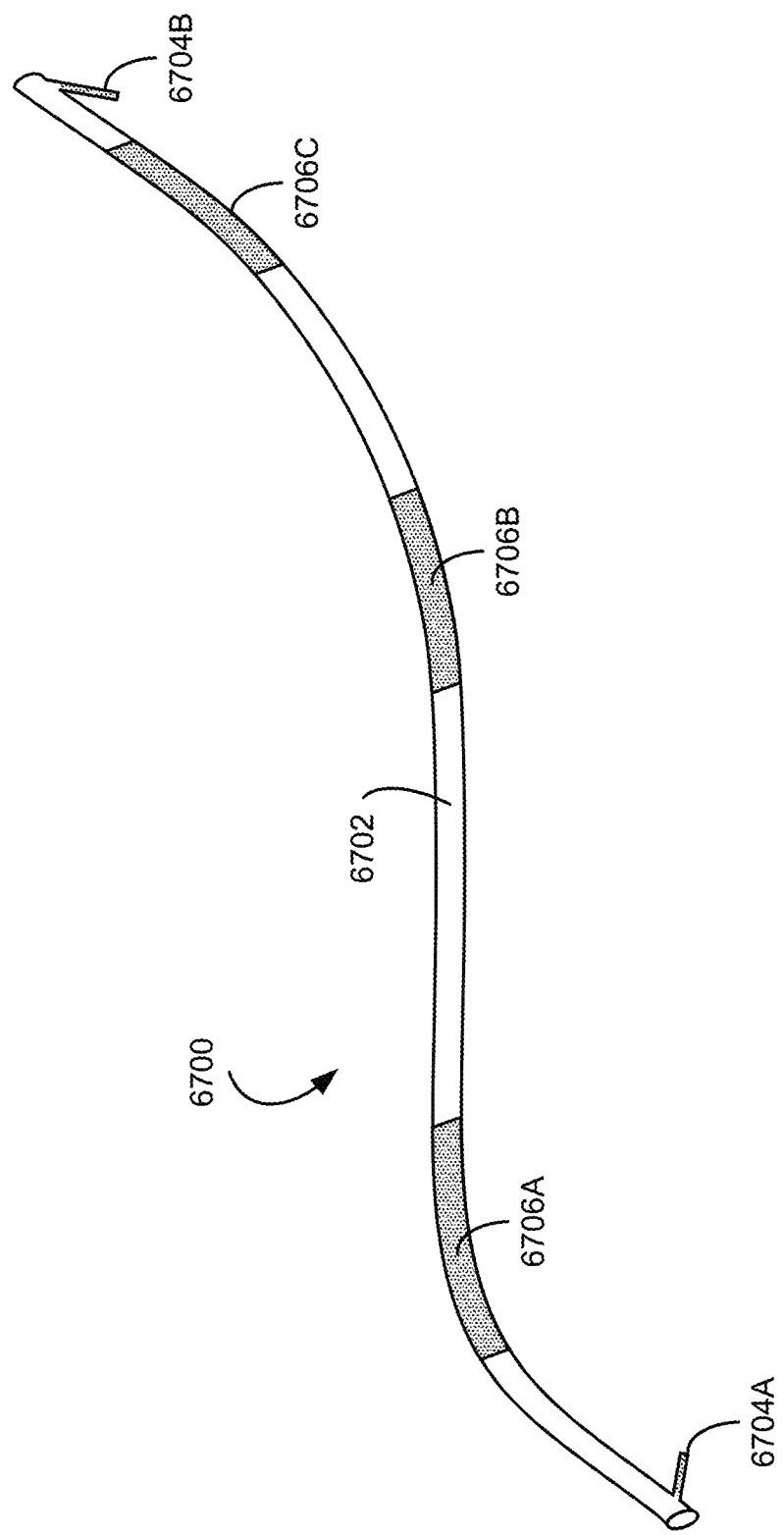
FIG. 67 is a schematic illustration of a textured biliary/pancreatic stent according to the present disclosure.

FIG. 67 is an example stent 6700 for use in duct-related applications with various features for improving anchoring relative to the duct. As shown in FIG. 67, the stent 6700 includes a tubular body 6702 which may optionally terminate in flared ends, hooks, barbs, or similar retention structures 6704A, 6704B. However, in certain implementations, the retention structures 6704A, 6704B may be omitted in favor of the other retention features discussed below.

As illustrated, the stent body 6702 may include texturing along its length. Such texturing may be applied along substantially the entire length of the body 6702 or along certain segments of the body 6702. For example, the stent 6700 illustrated in FIG. 67 includes three separate textured segments 6706A-C. Texturing is also applied to each of the end retention structures 6704A, 6704B. In use, the texturing on the stent 6700 improves anchoring by increasing friction/adhesion between the stent 6700 and a physiological lumen or structure within which the stent 6700 is inserted.

In certain implementations, the texturing may be integral to the stent body 6702. For example, the stent 6700 may be molded using silicone or other polymer materials with the texturing included on the surface as part of the molding process. In other implementations, the body 6702 may be initially formed without texturing and the texturing may be applied afterwards. For example, texturing may be applied by applying a layer or coating to the body 6702 including the texturing, overmolding the texturing onto the body 6702, or spraying the texturing onto the body 6702, among other manufacturing approaches.

The stent 6700 may be fabricated from various materials, each of which may have a durometer suitable for one or more specific applications. The stent 6700 may also be formed from multiple materials. For example, certain sections of the stent 6700 may be formed from relatively a low durometer material to facilitate bending of the stent 6700 while other sections may be formed from a relatively high durometer material to provide localized structural integrity. In another example implementation, the stent 6700 may include multiple layers with an interior layer of the stent 6700 having a higher durometer than exterior layers. In still another example implementation, the stent body 6702 may be formed from a first material having a first durometer while the textured portions or texturing applied to the body 6702 may have a second durometer.

The texturing of the stent 6700 may take various forms including, but not limited to, the various example texturing patterns discussed herein.

In another implementation of the present disclosure, a textured stent for implantation within a physiological lumen is provided. Such stents may be used, for example, within the gastrointestinal tract or vasculature of a patient.

Similar to the previously discussed stents, conventional gastrointestinal and vascular stents may migrate after being placed. Accordingly, placement and anchoring of such stents typically includes the use of sutures to hold the stents in place and/or mechanisms that apply outwardly radial loading to the stent such that it is maintained against the vascular or GI wall. In either case, placement of the stent and prevention of migration results in additional steps and procedures that may increase surgery time and/or raise the possibility of additional complications during implantation of the stent.

To address the foregoing issues, among others, the present disclosure includes a textured stent for implantation within a physiological lumen. The stents include an expandable body (e.g., an expandable mesh) that may be covered (entirely or in part) with a textured surface for increasing frictional engagement/adhesion between the stent and the inner wall of the physiological lumen.

Figure 68A:
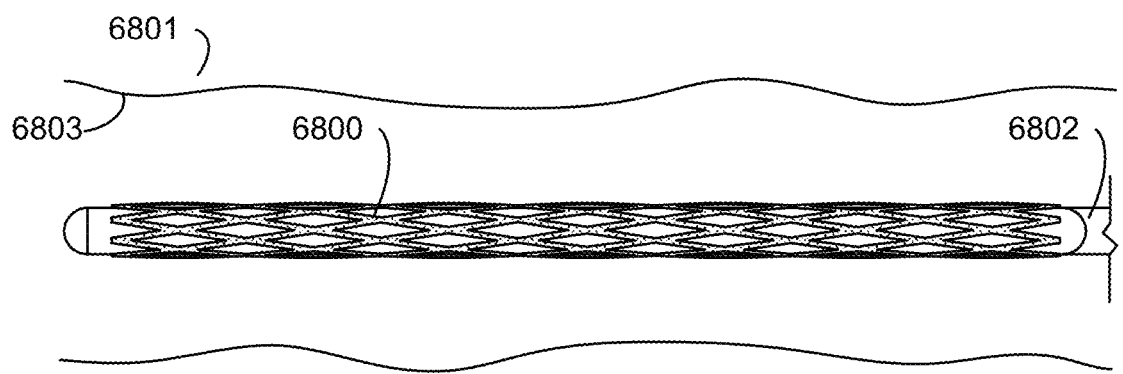
FIGS. 68A-68C are schematic illustrations of a physiological lumen illustrating deployment of a tubular mesh stent according to the present disclosure.
Figure 68B:
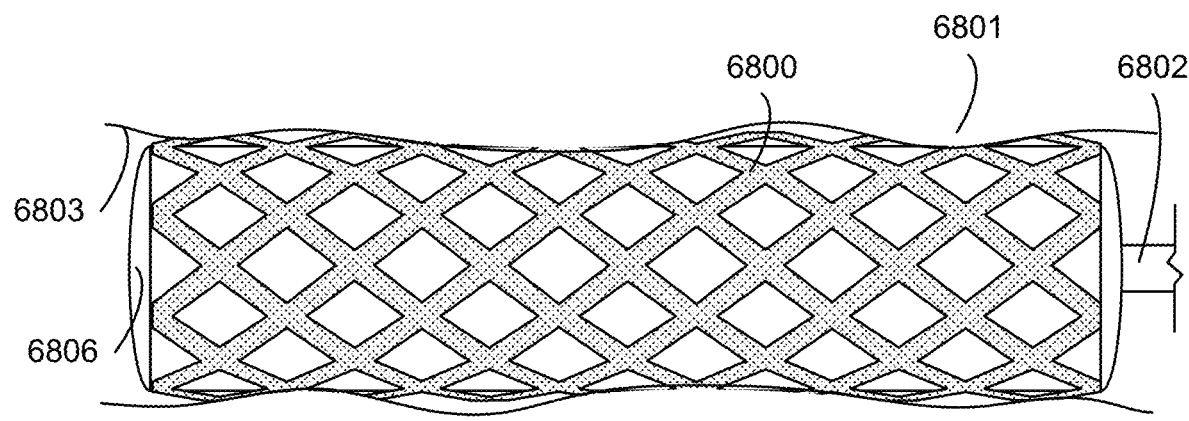
Figure 68C:
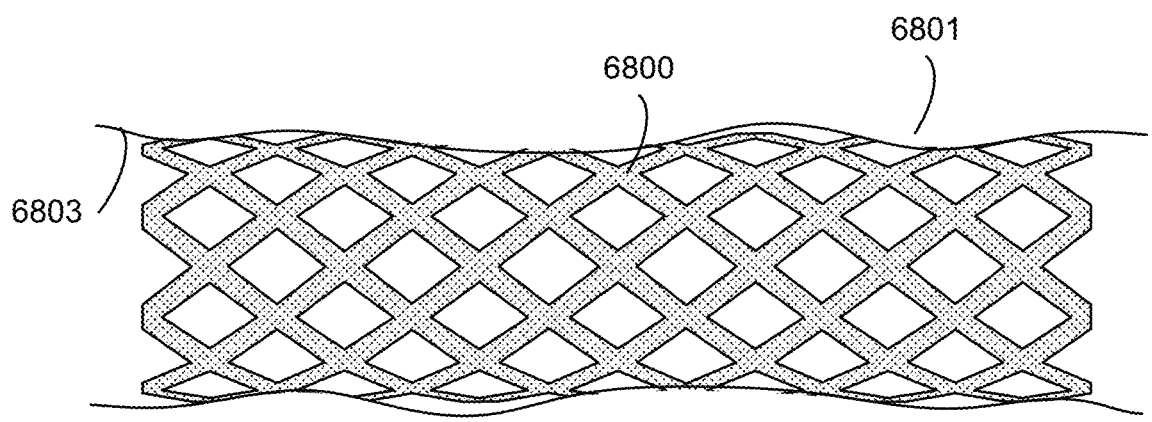

FIGS. 68A-68C illustrate an example process of implanting a textured stent 6800. Referring first to FIG. 68A, the textured stent 6800 may be disposed on a deployment tool 6802 in a first, compressed configuration. The deployment tool 6802 may then be advanced within the physiological lumen 6801 to position the stent 6800 at an implantation location.

When located, the stent 6800 may be deployed by expanding the stent 6800 such that its surface contacts an inner surface 6803 of the physiological lumen 6801. Although other deployment methods may be implanted, in the illustrated example, the deployment tool 6802 includes an expandable balloon 6806 that is inflated to expand the stent 6800 to contact the inner surface 6803 (as shown in FIG. 68B). When expanded, the textured surface of the stent 6800 abuts the inner surface 6803, with the texturing providing increased friction and adhesion as compared to conventional, smooth stents.

Following deployment of the stent 6800, the balloon 6806 may be deflated and removed from within the physiological lumen 6801, leaving the stent 6800 in place (as shown in FIG. 68C).

As previously noted, the texturing may be applied to some or the entire exterior surface of the stent 6800. For example, in certain implementations, texturing may be applied in one or more circumferential bands that extend about the stent 6800. In another implementation, texturing may be applied to discrete sections or blocks distributed about the exterior surface of the stent 6800.

Similar to the previous stent, the texturing may be integrally formed with the body of the stent 6800 or may be added in a subsequent process (e.g., by applying a layer or coating, overmolding, etc.).

As discussed in the context of the balloons, above, the texturing of the stent 6800 may be configured to have different frictional/adhesion properties in different configurations. For example, when in the compressed configuration illustrated in FIG. 68A, the texturing may have a relatively low friction coefficient to prevent or minimize adhesion to the physiological lumen during deliver of the stent 6800. However, in response to the strain applied during deployment of the stent 6800, the friction coefficient of the texturing may increase to facilitate anchoring of the stent 6800 within the physiological lumen.

Figure 69:
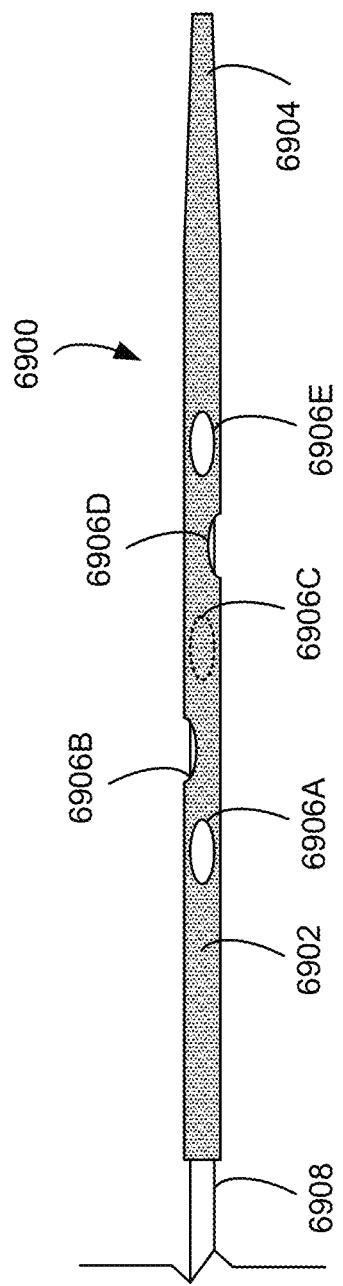
FIG. 69 is a schematic illustration of a tapered stent according to the present disclosure.

FIG. 69 is a schematic illustration of another stent 6900 according to the present disclosure. As illustrated, the stent 6900 includes a body 6902 having a tapered tip 6904. Such stents may be used to facilitate fluid in the bile duct. Similar to the previously discussed stents, the stent body 6902 may be at least partially textured such that when implanted, the texturing of the stent body 6902 frictionally engages/adheres to the wall of a physiological lumen or other tissue, thereby resisting migration of the stent 6900 following implantation. Although the diameter of the stent body 6902 may vary, in at least one implementation the stent body 6902 tapers from a first diameter of approximately 10 Fr down to a second diameter of approximately 8.5 Fr. In certain implementations, the tapered tip 6904 may be reduced to allow use of a pusher catheter 6908 (as described below) but may include a hole or lumen through which a guidewire may be passed.

In certain implementations, the body 6902 may define one or more ports or openings, along its length to permit fluid. For example, in the implementation at least one implementation, multiple ports 6906A-6906E may be distributed along the length of the body 6902 in a spiral/helical arrangement. In one specific implementation, the spacing of the ports 6906A-6906E may be approximately 1 cm.

Although stent 6900 may be advanced/implanted using various techniques, in at least one approach, a pusher catheter 6908 is inserted into the stent body 6902 and made to abut the inside of the tapered tip 6904. The stent 6900 may then be pushed from the proximal end using the pusher catheter 6908.

Laparoscopic and Similar Surgical Tools

As another example application, texturing in accordance with the present disclosure may be applied in the context of laparoscopic tools. For example, FIG. 70 illustrates an operational environment 7000 and, in particular a cross-sectional view of a patient abdomen 7002 including an abdominal wall 7004 and abdominal organs 7006.

Figure 70:
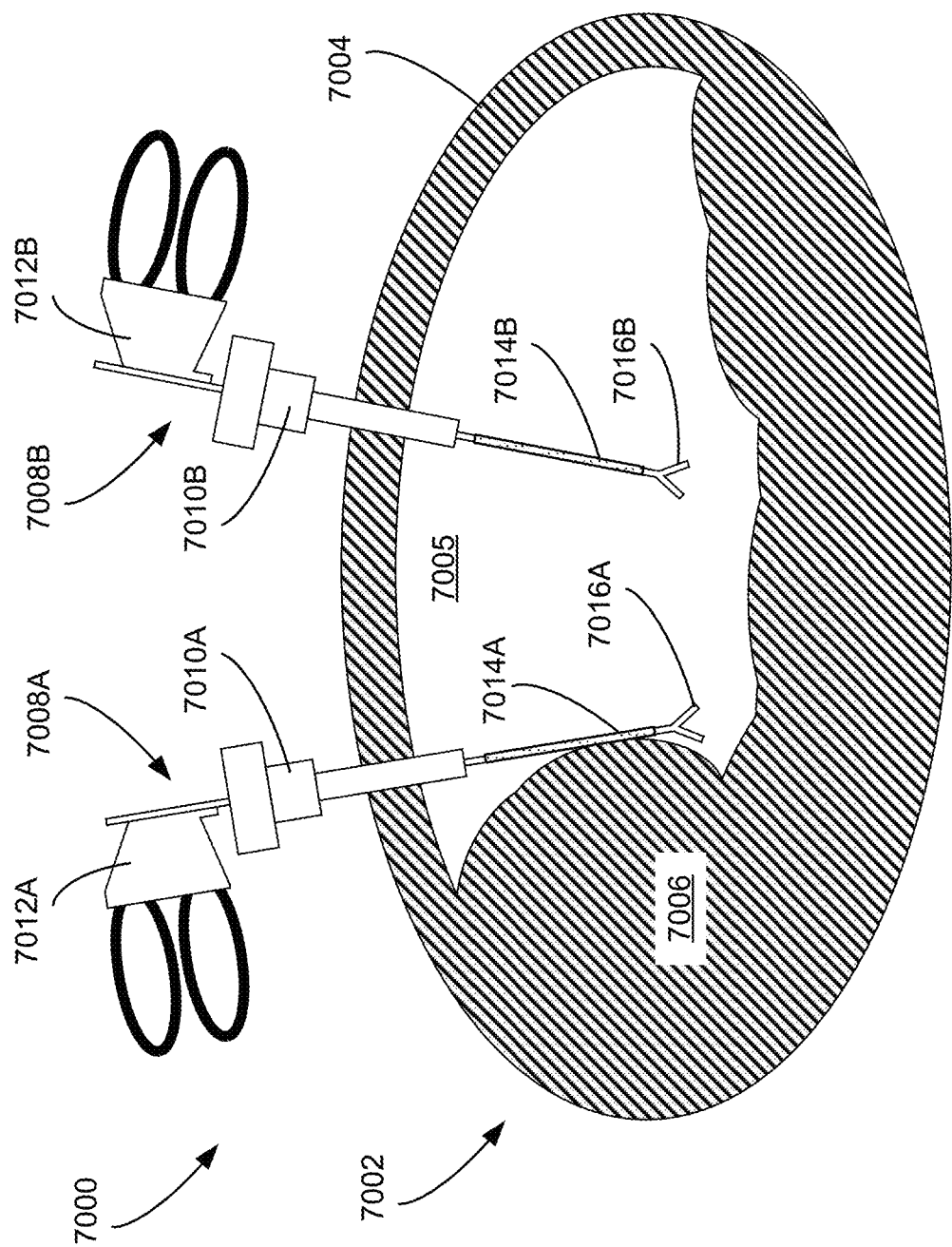
FIG. 70 is an operational environment and, in particular, a cross-sectional view of a patient abdominal cavity including textured surgical tools in accordance with the present disclosure.

The operational environment 7000 further includes a pair of surgical tool assemblies 7008A, 7008B, which in the particular example of FIG. 70, are manually operated laparoscopic tool assemblies. The surgical tool assembly 7008A includes a trocar/port assembly 7010A, which may extend through the abdominal wall 7004 to provide access to the internal abdominal cavity 7005, which, in the case of laparoscopic procedures, may be insufflated during surgery. The surgical tool assembly 7008A further includes a surgical tool 7012A including a tool shaft 7014A terminating in a tool end effector 7016A. The surgical tool assembly 7008B similarly includes a surgical tool 7012B including a tool shaft 7014B terminating in a tool end effector 7016B. For clarity and simplicity, the following discussion refers only to surgical tool assembly 7008A, however, the description of surgical tool assembly 7008A is generally applicable to surgical tool assembly 7008B.

As discussed below in further detail, at least a portion of the surgical tool 7012A may include a textured surface in accordance with the present disclosure. For example, one or both of the tool shaft 7014A and the tool end effector 7016A may be at least partially textured as described herein. Among other things, such texturing may facilitate manipulation and/or retention of tissue and organs of the abdomen. For example and as illustrated in FIG. 70, during surgery, the tool shaft 7014A may be made to move aside or hold an internal organ. Texturing applied to the tool shaft 7014A may generally increase grip/adhesion between the tool shaft 7014A and the tissue/organ, thereby improving the degree of control over the tissue/organ and reducing the likelihood that the tissue/organ will slip from the tool shaft 7014A. As previously noted, texturing may also or alternatively be applied to the tool end effector 7016A to similarly increase adhesion and retention of the tool end effector 7016A.

Figure 71:
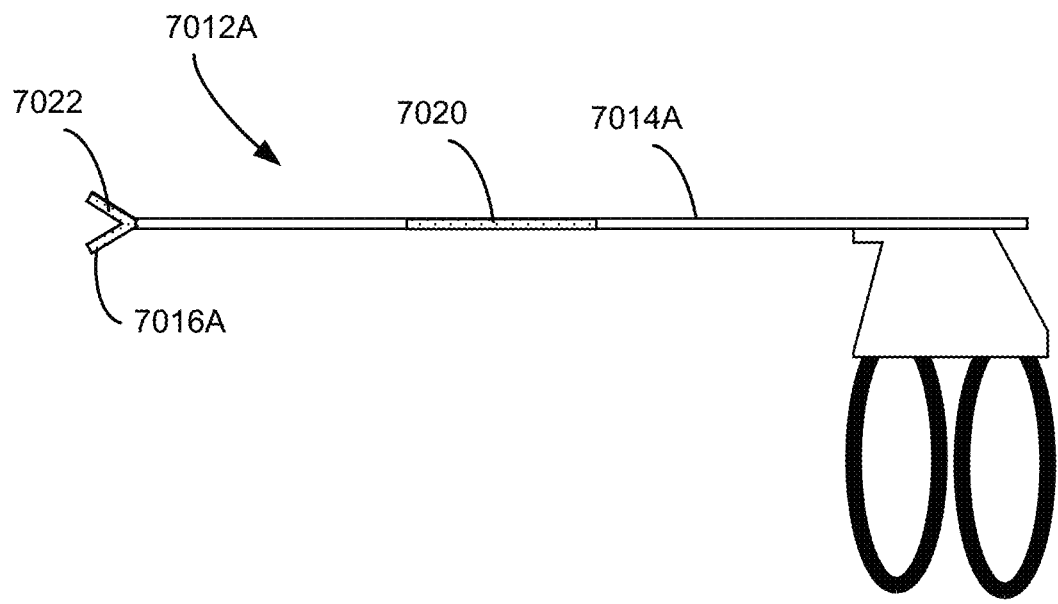
FIG. 71 is a side elevation view of a surgical tool of FIG. 64 in which the texturing is integrated with a shaft of the surgical tool.
Figure 72:
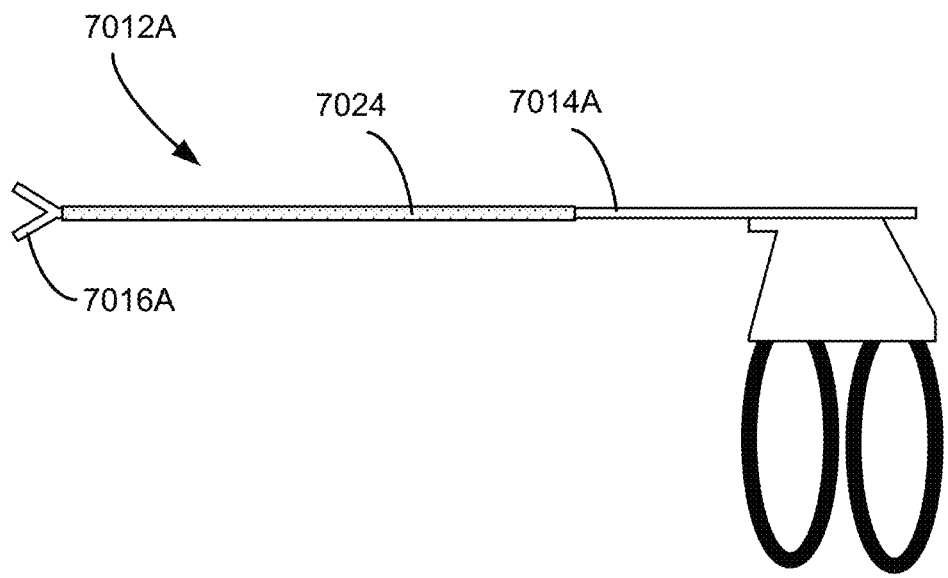
FIG. 72 is a side elevation view of the surgical tool of FIG. 64 in which the texturing is provided by a sheath or wrap applied to the shaft of the surgical tool.

FIGS. 71 and 72 illustrate different implementations of the surgical tool 7012A and, in particular, different approaches to texturing the surgical tool 7012A. Referring first to FIG. 65, the surgical tool 7012A is shown as having a first textured portion 7020 disposed along the tool shaft 7014A and a second textured portion 7022 corresponding to the tool end effector 7016A.

The first textured portion 7020 may be formed in various ways. For example and without limitation, in at least certain implementations, the textured portion 7020 may be integrally formed with the tool shaft 7014A. In other examples, the textured portion 7020 may be overmolded onto the tool shaft 7014A. In still other implementations, the textured portion 7020 may be a separate segment of the tool shaft 7014A that is inserted between and coupled to a proximal and/or distal segment of the tool shaft 7014A. In yet other implementations, the textured portion 7020 may be formed by applying a coating or similar treatment onto the tool shaft 7014A.

The second texture portion 7022 corresponding to the tool end effector 7016A may similarly be integrally formed with the tool end effector 7016A or formed onto the tool end effector 7016A, such as by overmolding or coating of the tool end effector 7016A. Although illustrated in FIG. 70 as being applied to the entire tool end effector 7016A, texturing may alternatively be applied to only a portion of the tool end effector 7016A. For example and without limitation, in one application, texturing may only be applied to a proximal surface of the tool end effector 7016A. In another example implementation in which the tool end effector 7016A is a grasper-type tool including jaws, texturing may be applied only to the inner surface of the jaws.

FIG. 72 is an alternative implementation of the surgical tool 7012A in which a textured cover 7024 is disposed on the tool shaft 7014A. In certain implementations, the textured cover 7024 may be a sheath through which the tool shaft 7014A is inserted, the exterior surface of the sheath having texturing as described herein. The sheath may then be adhered to, shrunk onto, or otherwise retained on the tool shaft 7014A. In an alternative implementation, the textured cover 7024 may be in the form of a wrap, tape, etc. that is wrapped around the tool shaft 7014A. To retain the wrap/tape, an adhesive may be applied to the tool shaft 7014A or the wrap/tape prior to wrapping. Alternatively, the wrap/tape may have an adhesive backing.

Although illustrated in FIGS. 70-72 as manually-operated laparoscopic tools, implementations of the present disclosure may include actuated tools including robotically controlled tools. The various aspects of FIGS. 70-72 are also not limited to the grasper-type tools illustrated and application of the described texturing to other tools, including other laparoscopic tools and other non-laparoscopic tools, is contemplated.

In certain stent applications, texturing of stents according to the present disclosure may include protrusions, ridges, or similar structures that extend outwardly from the exterior surface of the stent. In certain implementations, such protrusions extend in a substantially radial direction. However, in other implementations, at least a portion of the texturing may be swept or otherwise biased toward an end of the stent. By doing so, the texturing may provide additional resistance to movement in the direction of the bias while providing reduced resistance in the opposite direction. So, for example, a stent may include texturing that is backswept in a direction opposite a direction of advancement such that the friction provided by the texturing is reduced during insertion and advancement but increased in a direction opposite that of advancement following deployment (e.g., to counter potential movement caused by blood flow, peristalsis, etc.). Biased texturing and control of such biasing (e.g., by selectively expanding or compressing the stent to vary the angle of the texturing) may also facilitate removal of the stent as it allows physicians and technicians to dynamically modify the resistance/adhesion provided by the texturing.

In at least some implementations of stents according to the present disclosure, texturing of the stent may include applying texturing to a metallic or similar substrate. For example texturing of a tubular or expandable metallic stent may be applied by coating the substrate, applying an adhesive layer including the texturing to the substrate, spraying texturing onto the substrate, overmolding texturing onto the substrate, or any other suitable method of applying the texturing to the substrate.

It should be understood that the principles discussed in the foregoing disclosure may be combined in ways not explicitly identified above. For example, the various aspects of textures (e.g., dimensions, material, spacing, strain-response, etc.) discussed in the context of endoscopic balloons may be applied to any of the other components discussed herein (e.g., endoscopes, overtubes, endoscopic tools, stents, etc.). As a result, to the extent a given feature, such as texturing, is described with respect to a particular application or component, any such description should be considered to be equally applicable to any other similar feature discussed herein.

The present disclosure is further directed to kits including medical devices in accordance with the present disclosure. In certain implementations, the kit includes an endoscope or similar medical device including at least one inflatable balloon having protrusions as described herein. In other implementations, the kit further includes a catheter including a balloon having protrusions as described herein. In yet other implementations, the kit includes instructional materials detailing methods of using medical devices in accordance with the present disclosure. In still another implementation, the kit includes each of an endoscope and a catheter, each of which includes a balloon as described herein. In still other implementations, the kit includes instructional materials detailing methods of using the endoscope and the catheter.

As used herein, each of the following terms has the meaning associated with it in this section.

As used herein, unless defined otherwise, all technical and scientific terms generally have the same meaning as commonly understood by one of ordinary skill in the art to which this disclosure belongs. Generally, the nomenclature used herein is those well-known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein, "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "instructional material" includes a publication, a recording, a diagram, or any other medium of expression that may be used to communicate the usefulness of the compositions and/or methods of the present disclosure. The instructional material of the kit may, for example, be affixed to a container that contains the compositions of the present disclosure or be shipped together with a container that contains the compositions. Alternatively, the instructional material may be shipped separately from the container with the intention that the recipient uses the instructional material and the compositions cooperatively. For example, the instructional material is for use of a kit; and/or instructions for use of the compositions.

Throughout this disclosure, various aspects of the present disclosure may be presented in a range format. It should be understood that the description in range format is merely for convenience and brevity and should not be construed as an inflexible limitation on the scope of the present disclosure. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Every formulation or combination of components described or exemplified can be used to practice implementations of the current disclosure, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination.

Although the description herein contains many example implementations, these should not be construed as limiting the scope of the current disclosure but as merely providing illustrative examples.

All references throughout this disclosure (for example, patent documents including issued or granted patents or equivalents; patent application publications; and non-patent literature documents or other source material) are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. In general the terms and phrases used herein have their art-recognized meaning, which can be found by reference to standard texts, journal references, and contexts known to those skilled in the art. Any preceding definitions are provided to clarify their specific use in the context of the present disclosure.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present disclosure.

The disclosures of each and every patent, patent application, and publication cited herein are hereby incorporated herein by reference in their entirety.

While this disclosure includes reference to specific embodiments, it is apparent that other embodiments and variations of this disclosure may be devised by others skilled in the art without departing from the true spirit and scope of the disclosure. The appended claims are intended to be construed to include all such embodiments and equivalent variations.

What is claimed is:

1. An overtube assembly for use with an elongate medical tool, the overtube assembly comprising:
   an overtube comprising a flexible tubular body having a proximal end and a distal end, the flexible tubular body including:
      a split extending from the proximal end to the distal end; and
      circumferentially extending bands distributed along the flexible tubular body, the circumferentially extending bands reinforcing portions of the flexible tubular body;
      a longitudinally extending strip; and
      a rod adjacent the split and extending along the split, wherein each of the circumferentially extending bands extends from the longitudinally extending strip and each of the circumferentially extending bands is coupled to the rod; and
   an inflatable balloon coupled to a distal portion of the flexible tubular body,
   wherein the flexible tubular body is disposable over a section of the elongate medical tool by inserting the elongate medical tool through the split.

2. The overtube assembly of claim 1, further comprising an air supply lumen extending from the distal end, the air supply lumen in communication with an internal volume of the inflatable balloon.

3. The overtube assembly of claim 1, wherein:
the inflatable balloon is one of a plurality of inflatable balloons coupled to the distal portion of the flexible tubular body, and
the overtube assembly further comprises a plurality of air supply lumens, each air supply lumen of the plurality of air supply lumens in communication with an internal volume of a respective inflatable balloon of the plurality of inflatable balloons.

4. The overtube assembly of claim 1, wherein the split includes a proximal split portion having a first width and a distal split portion having a second width, the second width being greater than the first width.

5. The overtube assembly of claim 1, wherein:
the flexible tubular body comprises a first overlapping portion and a second overlapping portion,
the first overlapping portion and the second overlapping portion are configured to overlap when the flexible tubular body is disposed over the section of the elongate medical tool.

6. The overtube assembly of claim 5, wherein:
when overlapping, an interface is formed between an inner surface of the first overlapping portion and an outer surface of the second overlapping portion,
the inner surface of the first overlapping portion comprises a first surface structure,
the outer surface of the second overlapping portion comprises a second surface structure, and
the first surface structure is configured to engage the second surface structure when the first overlapping portion overlaps the second overlapping portion.

7. The overtube assembly of claim 1, wherein the flexible tubular body comprises one or more high flexibility regions disposed along the flexible tubular body, each of the high flexibility regions comprising a hole through the flexible tubular body or a local thinning of the flexible tubular body.

8. The overtube assembly of claim 1 further comprising a zipper closure extending along the split.

9. An overtube for use with an elongate medical tool, the overtube comprising:
a flexible tubular body having a proximal end and a distal end, the flexible tubular body including:
a split extending from the proximal end to the distal end; and
circumferentially extending bands distributed along the flexible tubular body, the circumferentially extending bands reinforcing portions of the flexible tubular body;
a longitudinally extending strip; and
a rod adjacent the split and extending along the split, wherein each of the circumferentially extending bands extends from the longitudinally extending strip and each of the circumferentially extending bands is coupled to the rod,
wherein the flexible tubular body is disposable over a section of the elongate medical tool by inserting the elongate medical tool through the split.

10. The overtube of claim 9, wherein the split includes a proximal split portion having a first width and a distal split portion having a second width, the second width being greater than the first width.

11. The overtube of claim 9, wherein:
the flexible tubular body comprises a first overlapping portion and a second overlapping portion,
the first overlapping portion and the second overlapping portion are configured to overlap when the flexible tubular body is disposed over the section of the elongate medical tool.

12. The overtube of claim 11, wherein:
when overlapping, an interface is formed between an inner surface of the first overlapping portion and an outer surface of the second overlapping portion,
the inner surface of the first overlapping portion comprises a first surface structure,
the outer surface of the second overlapping portion comprises a second surface structure, and
the first surface structure is configured to engage the second surface structure when the first overlapping portion overlaps the second overlapping portion.

13. The overtube of claim 9, wherein the flexible tubular body comprises one or more high flexibility regions disposed along the flexible tubular body, each of the high flexibility regions comprising a hole through the flexible tubular body or a local thinning of the flexible tubular body.

14. The overtube of claim 9 further comprising a zipper closure extending along the split.

15. An overtube assembly for use with an elongate medical tool, the overtube assembly comprising:
an overtube comprising a flexible tubular body having a proximal end and a distal end, the flexible tubular body defining a first air supply lumen extending from the proximal end to a first overtube port and a second air supply lumen extending from the proximal end to a second overtube port, the flexible tubular body further including:
a split extending from the proximal end to the distal end;
circumferentially extending bands distributed along the flexible tubular body, the circumferentially extending bands reinforcing portions of the flexible tubular body;
a longitudinally extending strip; and
a rod adjacent the split and extending along the split, wherein each of the circumferentially extending bands extends from the longitudinally extending strip and each of the circumferentially extending bands is coupled to the rod;
a first inflatable balloon coupled to an exterior surface of the flexible tubular body on a first side of a distal portion of the flexible tubular body, the first inflatable balloon having a first internal volume and defining a first balloon port, the first balloon port in communication with the first overtube port; and
a second inflatable balloon coupled to the exterior surface of the flexible tubular body on a second side of the distal portion of the flexible tubular body, the second inflatable balloon having a second internal volume and defining a second balloon port, the second balloon port in communication with the second overtube port,
wherein the flexible tubular body is disposable over a section of the elongate medical tool by inserting the elongate medical tool through the split.

16. The overtube assembly of claim 15, wherein each of the first inflatable balloon comprises a first textured exterior surface and the second inflatable balloon comprises a second textured exterior surface, each of the first textured exterior surface and the second textured exterior surface comprising a plurality of outwardly extending protrusions.

17. The overtube assembly of claim 15, wherein the split includes a proximal split portion having a first width and a distal split portion having a second width, the second width being greater than the first width.

18. The overtube assembly of claim 15, wherein the second inflatable balloon is coupled to the second side of the distal portion of the flexible tubular body opposite the first inflatable balloon.

\* \* \* \* \*

UNITED STATES PATENT AND TRADEMARK OFFICE
CERTIFICATE OF CORRECTION

PATENT NO. : 11,730,928 B2  
APPLICATION NO. : 16/875793  
DATED : August 22, 2023  
INVENTOR(S) : Mark E. Rentschler et al.

Page 1 of 1

It is certified that error appears in the above-identified patent and that said Letters Patent is hereby corrected as shown below:

On the Title Page

Item (63) Related U.S. Application Data (continued on page 2)
Line 3, delete 1,108,994 and replace with 11,089,944.

Signed and Sealed this
Second Day of January, 2024

Katherine Kelly Vidal
*Director of the United States Patent and Trademark Office*